United States Patent [19]
Tankovich et al.

[11] Patent Number: 6,162,211
[45] Date of Patent: Dec. 19, 2000

[54] SKIN ENHANCEMENT USING LASER LIGHT

[75] Inventors: Nikolai I. Tankovich, San Diego, Calif.; Kurt A. Dasse, Needham, Mass.; Paul W. Fairchild, San Diego, Calif.; Zhong- Quan Zhao, San Diego, Calif.; Vladimir G. Kolinko, San Diego, Calif.

[73] Assignee: ThermoLase Corporation, San Diego, Calif.

[21] Appl. No.: 08/985,856

[22] Filed: Dec. 4, 1997

Related U.S. Application Data

[60] Provisional application No. 60/052,718, Jul. 16, 1997, and provisional application No. 60/033,238, Dec. 5, 1996.

[51] Int. Cl.[7] .................................................. A61B 18/18
[52] U.S. Cl. ................................................. 606/9; 607/89
[58] Field of Search .............................. 128/898; 607/88; 600/89, 1; 606/228, 9, 10, 17

[56] References Cited

U.S. PATENT DOCUMENTS

| | | |
|---|---|---|
| 3,538,919 | 11/1970 | Mayer . |
| 3,693,623 | 9/1972 | Harte et al. . |

(List continued on next page.)

FOREIGN PATENT DOCUMENTS

| | | |
|---|---|---|
| B-57576/86 | 11/1986 | Australia . |
| 1208702 | 7/1986 | Canada . |

(List continued on next page.)

OTHER PUBLICATIONS

PCT Search Report, Nov. 11, 1998, PCT/US97/22347.
Andreoni, Porphyrins in Tumor Phototherapy, 143–155 (1984).
Anders et al., Conf. Laser 77 Optics Electronics 20–24 (Jun. 1997).
Coleman, A Visit to the Office of Dr. John Yarborough, J. Dermatol. Surg. Oncol., 20: 332–335, (1994).
Finkelstein et al., Epilation of Hair–Bearing Urethral Grafts Utilizing the Neodymium: YAG Surgical Laser, Lasers in Surgery and Medicine, 10: 189–193, (1990).
Kaufmann et al., Cutting and Skin Ablative Properties of Pulsed Mid–Infrared Laser Surgery, J. Dermatol. Surg. Oncol., 20: 112–118, (1994).

(List continued on next page.)

*Primary Examiner*—Linda C. M. Dvorak
*Assistant Examiner*—Roy Gibson
*Attorney, Agent, or Firm*—Fish & Richardson P.C.

[57] ABSTRACT

Methods of applying laser light to the skin, and apparatus therefor, include methods for removing hair, for bleaching hair, for transdermal drug delivery, for sensing a body function, for skin tightening, and for imaging subsurface structures are described. The hair removal methods and the hair bleaching methods include infiltrating a transparent fluid with an index of refraction greater than that of skin tissue into hair ducts to help transmit the laser light down the hair ducts. The transdermal drug delivery and body function sensing methods include exfoliating layers of the stratum corneum from a section of skin with laser light. A transdermal drug delivery patch can be placed over the exfoliated skin section, or an electrical sensor can be placed over the exfoliated skin section. The skin tightening method includes implanting a light absorbing material in the dermis of a section of skin and illuminating the skin section to disturb the dermis in such a way as to cause a healing reaction that forms more collagen fibers. The imaging system includes a confocal microscope that has been adapted to view only a time-gated portion of laser light reflected from the skin.

14 Claims, 34 Drawing Sheets

U.S. PATENT DOCUMENTS

| | | |
|---|---|---|
| 3,769,963 | 11/1973 | Goldman et al. . |
| 3,794,028 | 2/1974 | Mueller et al. . |
| 3,821,510 | 6/1974 | Muncheryan . |
| 3,834,391 | 9/1974 | Block . |
| 3,900,034 | 8/1975 | Katz et al. . |
| 4,336,809 | 6/1982 | Clark . |
| 4,388,924 | 6/1983 | Weissman et al. . |
| 4,461,294 | 7/1984 | Baron . |
| 4,608,978 | 9/1986 | Rohr . |
| 4,617,926 | 10/1986 | Sutton . |
| 4,619,672 | 10/1986 | Robertson . |
| 4,642,128 | 2/1987 | Solorzano . |
| 4,701,193 | 10/1987 | Robertson et al. . |
| 4,712,543 | 12/1987 | Baron . |
| 4,792,341 | 12/1988 | Kozikowski . |
| 4,813,412 | 3/1989 | Yamazaki . |
| 5,057,104 | 10/1991 | Chess . |
| 5,059,192 | 10/1991 | Zaias . |
| 5,217,455 | 6/1993 | Tan . |
| 5,226,907 | 7/1993 | Tankovich . |
| 5,236,950 | 8/1993 | Aoyama et al. . |
| 5,282,797 | 2/1994 | Chess . |
| 5,290,273 | 3/1994 | Tan . |
| 5,304,170 | 4/1994 | Green . |
| 5,360,447 | 11/1994 | Koop . |
| 5,401,503 | 3/1995 | Murayama . |
| 5,423,803 | 6/1995 | Tankovich . |
| 5,425,728 | 6/1995 | Tankovich ................................ 606/9 |
| 5,445,634 | 8/1995 | Keller . |
| 5,464,436 | 11/1995 | Smith . |
| 5,486,172 | 1/1996 | Chess . |
| 5,595,568 | 1/1997 | Anderson et al. . |
| 5,630,811 | 5/1997 | Miller . |
| 5,647,866 | 7/1997 | Zaias et al. ............................... 606/9 |
| 5,752,948 | 5/1998 | Tankovich et al. ........................ 606/9 |
| 5,752,949 | 5/1998 | Tankovich et al. ........................ 606/9 |
| 5,766,214 | 6/1998 | Mehl, Sr. et al. ........................ 606/9 |
| 5,871,480 | 2/1999 | Tankovich ................................ 606/9 |

FOREIGN PATENT DOCUMENTS

| | | |
|---|---|---|
| 1041610 | 6/1994 | Canada . |
| 2148559 | 11/1995 | Canada . |
| 064967 | 4/1995 | European Pat. Off. . |
| 0 827 716 A2 | 3/1998 | European Pat. Off. ........ A61B 17/36 |
| 2267122 | 11/1975 | France . |
| 2590791 | 6/1987 | France . |
| 2595239 | 9/1987 | France . |
| 2515697 | 10/1975 | Germany . |
| 3220962 | 12/1983 | Germany . |
| 63-249577 | 10/1988 | Japan . |
| 2157176 | 10/1985 | United Kingdom . |
| WO 80/02640 | 12/1980 | WIPO . |
| WO 86/02783 | 5/1986 | WIPO . |
| WO 9011653 | 10/1990 | WIPO . |
| WO 91/04073 | 4/1991 | WIPO . |
| WO 91/13652 | 9/1991 | WIPO . |
| WO 91/13653 | 9/1991 | WIPO . |
| WO 93/21841 | 11/1993 | WIPO . |
| WO 93/21992 | 11/1993 | WIPO . |
| WO 96/23447 | 8/1996 | WIPO ............................ A61B 17/36 |
| WO 97/22384 | 6/1997 | WIPO ............................ A61N 5/06 |

OTHER PUBLICATIONS

Dreno et al., The Benefit of Chilling In Argon–Laser Treatment of Port–Wine Stains, Plastic Reconstr. Surg. 75.1: 42–45, (1985).

NelsoN et al., Dynamic Epidural Cooling in Conjunction with Laser–Induced Photothermolysis of Port Wine Stain Blood Vessels, Lasers in Surgery and Medicine 19: 224–229, (1986).

Finkel et al., Pulsed Alexandrite Laser Technology for Noninvasive Hair Removal, J. Clin. Laser Med. & Surg. 15:225–229 (1997).

Nanni et al., Optimizing Treatment Parameters for Hair Removal Using a Topical Carbon—Based Solution and 1064–nm Q–Switched Neodymium: Yag Laser Energy, Arch. Dermatol 133: 1546–1549, (1997).

K. L. Erbium Laser Assists Transdermal Drug Delivery Medical Laser Report, (Feb. 1997).

Chan et al., Effects of Compression on Soft Tissue Optical Properties, IEEE Journal of Special Topics in Quantam Electronics on lasers in Medicine and Biology,2(4):943–950 (Dec. 1996).

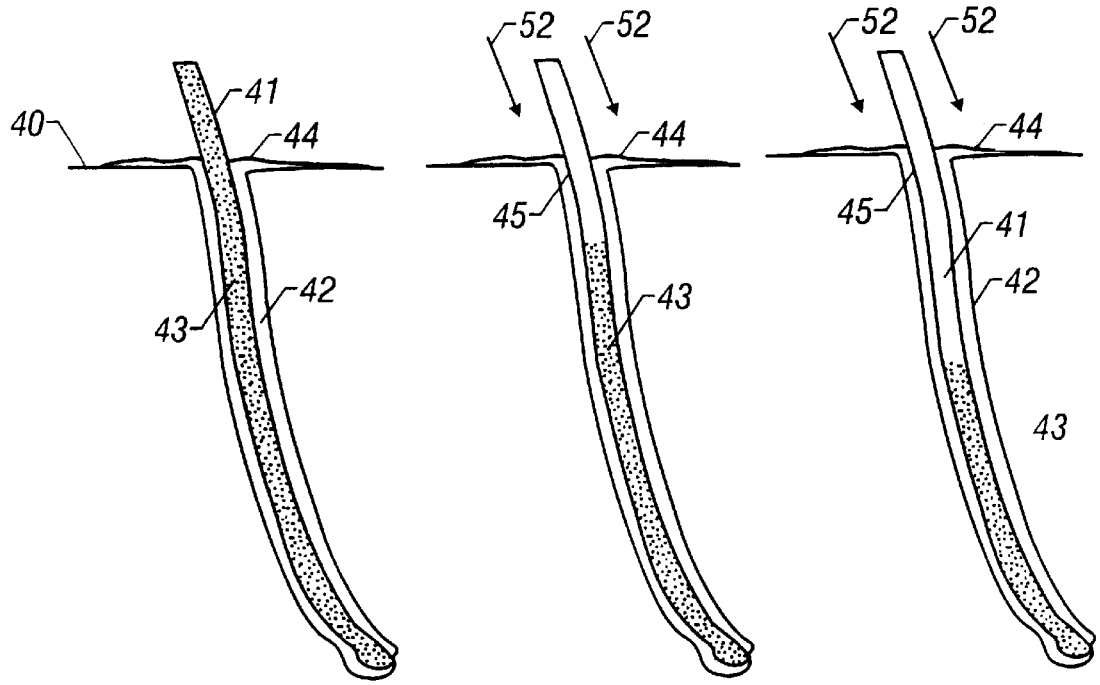
FIG. 2A  FIG. 2B  FIG. 2C
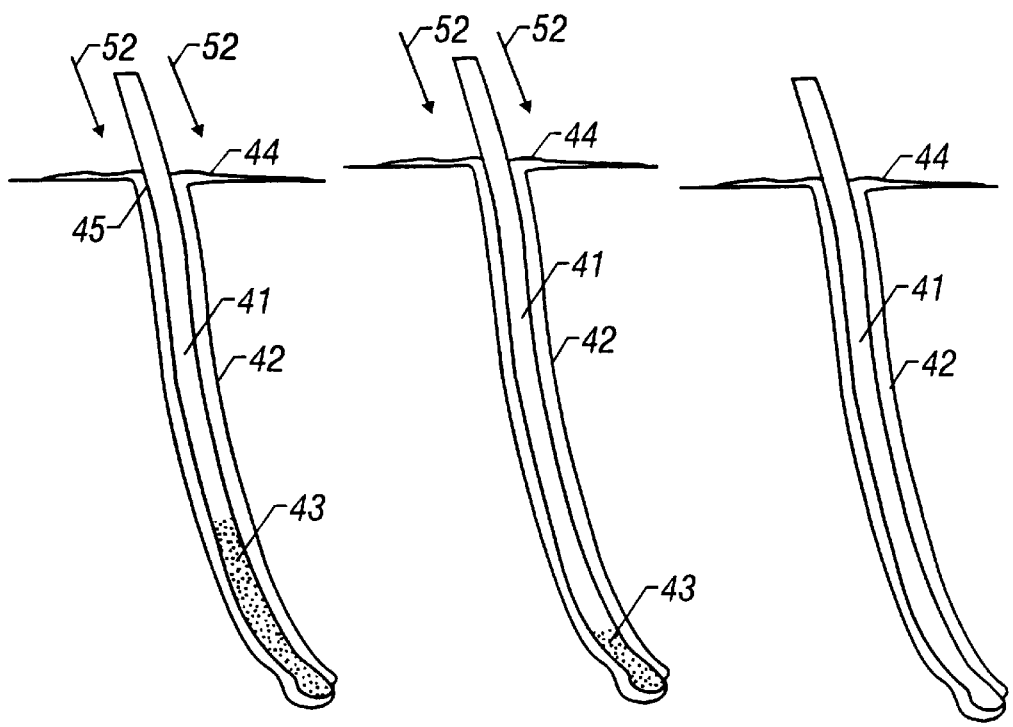
FIG. 2D  FIG. 2E  FIG. 2F

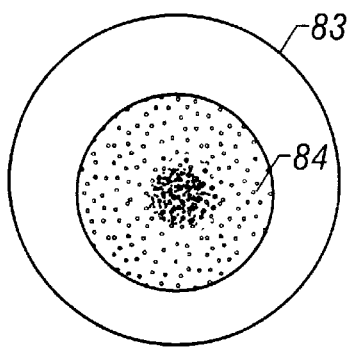
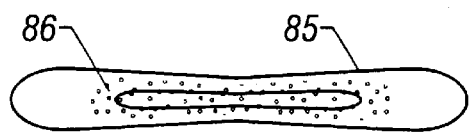
FIG. 22A
FIG. 22B
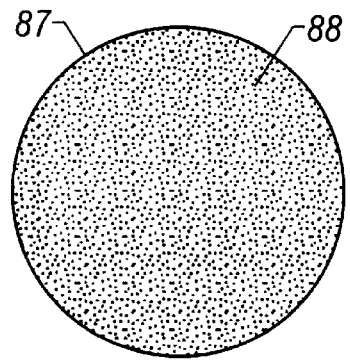
FIG. 22C
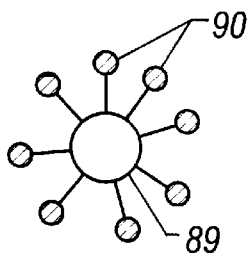
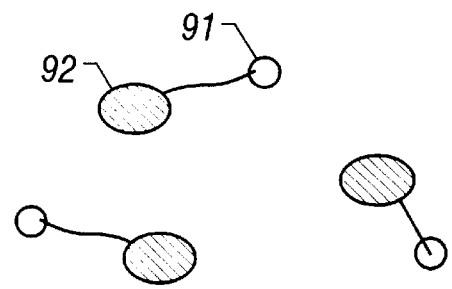
FIG. 22D
FIG. 22E

SKIN ENHANCEMENT USING LASER LIGHT

CROSS-REFERENCE TO RELATED APPLICATIONS

This application is a continuation-in-part application of U.S. provisional application Ser. No. 60/052,718, filed on Jul. 16, 1997, and U.S. provisional application Ser. No. 60/033,238, filed on Dec. 5, 1996.

This application is related to co-pending U.S. patent applications Ser. No. 08/955,390 filed Oct. 21, 1997; Ser. No. 08/777,576, filed Dec. 31, 1996; Ser. No. 08/695,200, filed Aug. 1, 1996; Ser. No. 08/644,231, filed May 13, 1996; Ser. No. 08/492,283, filed Jun. 19, 1995; Ser. No. 08/489,358, filed Jun. 12, 1995; Ser. No. 08/489,352, filed Jun. 12, 1995; and to U.S. application Ser. No. 08/984,892, filed on even date with this application, and which is incorporated herein by reference.

TECHNICAL FIELD

The invention relates to devices and methods of applying light to the skin for cosmetic hair removal, hair bleaching, tightening and strengthening the skin, imaging subsurface skin structures, transdermal drug delivery and measurement of body functions.

BACKGROUND

Unwanted body hair, particularly dark hair on the face, legs, back and chest is a cosmetic concern for many people. Laser light has been used for cosmetic hair removal. To minimize damage to tissue surrounding hairs, some hair removal methods apply narrowly focused beams of light to a single hair or hair follicle. For example, U.S. Pat. No. 3,834,391 to Block discloses using a probe positioned at the top of a single hair duct to direct a narrow, focused beam of light down the hair duct beside the hair shaft, and thence to the papilla to coagulate papillar vessels. The Block patent also discloses that introducing mineral oil into the hair duct, for example, by rubbing it on the skin, helps transmit the light to the papilla. According to the Block patent, light energy is applied until the hair can be pulled out easily with tweezers. U.S. Pat. No. 4,388,924, to Weissman et al. discloses directing a narrow, focused beam of light in short duration, high intensity pulses to the epidermis adjacent a hair such that an extension of the beam intersects a single hair follicle at an angle through the skin.

Another approach, disclosed in U.S. Pat. No. 5,059,192, to Zajas, applies pulsed light having a wavelength of 694 nm, which wavelength is selected for absorption by melanosomes at the base of the hair follicle and papilla. The pulse duration is shorter than the thermal relaxation time of the melanin. The laser beam is directed from a position substantially vertically over a hair duct to the papilla.

U.S. Pat. Nos. 5,226,907 and 5,425,728, to Tankovich, the entire disclosures of which are herein incorporated by reference, disclose applying a light-absorbing contaminant topically to a skin section to be treated so that a portion of the contaminant enters hair follicles. The contaminant can be a water or oil-based suspension or solution containing chromophore particles having a high absorption at or near at least one frequency band of light. The chromophore particles, for example carbon or graphite particles, are generally sized too large to penetrate the barrier layer of the stratum corneum, but small enough to readily infiltrate the hair ducts to the hair follicles. Laser pulses are used to drive the contaminant down hair ducts and deep into hair follicles. The skin section containing the infiltrated hair follicles is then illuminated with a light beam that is highly absorbed by the contaminant, but that passes readily through skin. By this procedure, the hair cells surrounding the follicle that are responsible for hair growth are damaged or destroyed by energy transferred from the irradiated contaminant to the tissue surrounding the hair follicle.

Bleaching can make unwanted hair less noticeable. Chemical bleaching agents typically work only on the portion of the hair shaft above the skin surface. The unbleached portion below the skin surface rises above the skin and becomes visible as the hair continues to grow. U.S. Pat. No. 4,792,341, to Kozikowski et al., discloses using laser light to photobleach locks of hair that have been glued to transparent plates. Kozikowski et al. provide a table of optimal conditions for photobleaching using wavelengths of 530 nm and 1.06 $\mu$m to destroy melanin in hairs that are removed from the body.

U.S. Pat. No. 5,423,803, to Tankovichi et al., the entire disclosure of which is included by reference herein, discloses a cosmetic method of skin resurfacing using laser light to give the skin a smoother appearance. A contaminant that absorbs light is applied to the skin so as to infiltrate the contaminant in gaps and crevices between surface layers of the stratum corneum, which is composed of about 20 layers of dead cells and which helps to provide a barrier to entry of harmful substances into the skin and thence the bloodstream. The skin surface bearing the contaminant is then illuminated so that the contaminant absorbs enough energy to exfoliate the outermost three or so layers of cells in the stratum corneum without significant damage to living cells below the stratum corneum.

Confocal microscopes are capable of providing images of sections of objects in nonscattering or weakly scattering media. A sample is scanned with light at a selected focal depth. The reflected image signal is passed through a small aperture positioned in front of a photodetector. The aperture cuts off portions of the image signal scattered from outside the focal plane. However, if an object is embedded in a highly scattering media, the signal to noise ratio of the image signal becomes vanishingly small very quickly as the focal plane is moved deeper into the scattering media. Schmitt, et al., in "Confocal Microscopy In Turbid Media," J. Opt. Soc. Am. A, Vol. 11, No. 8, pp. 2226–35 (August 1994), report that the scattering imposes fundamental limits on the sectioning capability of the microscope. Confocal microscopes cannot image objects more than about 200–300 $\mu$m deep in tissue, such as skin.

SUMMARY

In one aspect, the invention provides a non-therapeutic, cosmetic method of removing hair from a section of healthy skin. Papillae that are located in hair ducts located in a section of skin include melanosomes, which absorb light. Also associated with the papillae are other naturally occurring light absorbers (chromophores), such as, for example, blood vessels. A fluid that is transparent to light at or near at least one frequency absorbed by at least one of the natural absorbers, e.g., melanosomes, is applied to the section of skin. A portion of the fluid is caused to enter hair ducts in the section of skin. A region of the section of skin is then illuminated with pulses of light at the at least one frequency. The illuminating light is directed so that a portion is conducted through the fluid to papillae in hair ducts located in the region of the section of skin. Another portion of the illuminating light is transmitted through the skin to the papillae in the hair ducts located in the region of the section of skin. At least some of the illuminating light is absorbed by a natural absorber associated with the illuminated papillae, causing heating of the illuminated papillae to a temperature of about 30°–90° C. above ambient skin temperature with each pulse. The method further includes inhibiting vaporizing the absorbers in the papillae, including cooling the region of the section of skin between the pulses.

In a second aspect, the invention provides a method of damaging or destroying papillae at the bottom of hair ducts in a section of skin so as to inhibit the regrowth of hair from the damaged follicles. According to this method, hairs from a section of skin are first removed from their respective follicles, for example, by waxing. A contaminant that has a high absorbance of light at or near at least one frequency is then applied to the skin such that some of the contaminant enters the hair ducts. The contaminant can be, for example, a mixture of carbon particles with an oil that is transparent to the at least one frequency band of light. Pulses of light from a laser at the at least one frequency are then applied to a region of the section of skin. The pulses are applied with an intensity and duration that cause at least some of the contaminant to be driven to the bottom of the hair ducts to the papillae. Additional transparent oil is then applied to the section of skin to fill at least the upper portions of the hair ducts with the oil. The oil at the tops of the ducts acts as a focusing lens for further pulses of the light, and the hollow ducts filled with the clear oil then act as light pipes to transmit the light pulses to the contaminant at the bottoms of the hair shafts. These pulses are absorbed by the contaminant, and are of duration, frequency, number and intensity to cause the contaminant to transfer sufficient energy to the papillae and tissues nourishing the papillae to damage or destroy at least some of the papillae in the region of skin illuminated by the pulses.

In another aspect, the invention provides a cosmetic method of bleaching hairs growing from a section of skin. Accordingly, this method includes applying to the skin section a fluid that is transparent to light at or near at least one frequency absorbed by melanosomes, and causing a portion of the fluid to penetrate hair ducts in the skin section. The method further includes illuminating the skin section containing the hairs with light at the at least one frequency, which light is directed so that a portion of the light is conducted through the fluid in the hair ducts and absorbed by melanosomes in hair shafts located in the hair ducts. The remaining portion of the light contacts the hairs above the skin surface and/or is transmitted through the skin section. Light conducted through the fluid or scattered through the skin or directly impinging on the hair shafts can be absorbed by melanosomes in the hair shafts, causing the melanosomes to explode or otherwise be destroyed so as to bleach the hair shafts, including bleaching at least a portion of one or more hair shafts below the skin surface. The illumination pulse duration, frequency, and intensity are selected such that the melanosomes are destroyed but the hair remains viable.

In addition, the invention provides a method for depositing a medicinal substance into the hair ducts. According to this method, the medicinal substance is encapsulated in or bound to carrier particles by conventional techniques, the carrier particles being formulated to have a slow-release property and being of a size that inhibits migration out of the ducts in between cells that line the ducts. The medicinal substance can include one or more drugs, such as a material that regulates hair growth or activity of sebaceous glands. The carrier particles can be liposomes, coacervate drops, erythrocyte shadow, latex or gelatin spheres, carbon microcrystals, or the like. A suspension of the carrier particles is topically applied to a section of skin that includes hair ducts. The suspension is then caused to infiltrate into the hair ducts, for example, by rubbing, and then excess material is wiped off. This leaves a concentration of the carrier particles around the hair shaft in and around the hair duct entrances. Then, the carrier substance is driven deeper into the hair ducts, for example, by applying mechanical or ultrasonic vibrations to the section of skin. Thus, drug delivery is localized in the hair ducts, the cells of which more readily absorb the drug or active agent than do the cells in the stratum corneum, which provides an outer covering for the skin. By employing carrier particles having different sizes, or release times, drug delivery can be prolonged over a period of time. In one embodiment, the carrier particles include a material that has a high optical absorbance at or near at least one frequency band of light that penetrates skin. After the carrier particles are driven into the hair ducts, the section of skin is illuminated with pulses of laser light at the at least one frequency of sufficient intensity, duration number and frequency to cause at least some of the carrier particles to release the included medicinal substance.

In still another aspect, the invention provides a method of tightening and strengthening a section of skin. According to this method, a material that has a high optical absorbance at or near at least one frequency band of light that will penetrate the skin is imbedded in the dermis. The absorbent material can be, for example, carbon particles, graphite thread, or the like. A region of the section of skin is then illuminated with light at the at least one frequency band, some of which light penetrates the skin and is absorbed by the absorbent material. The absorbent material transfers energy absorbed from the light to adjacent dennal tissue. This stimulates growth of new collagen fibers in the adjacent dermal tissue to add tensile strength and elasticity to the area with new collagen fiber growth.

In yet another aspect, the invention provides a method of enhancing transdermal drug delivery. The method includes applying light to a section of skin to cause removal of stratum corneum cells, and then applying a drug to the section of skin from which the stratum corneum cells have been removed. The stratum corneum cells can be removed a few layers at a time until about 10 to 20 layers are removed. To remove the top few layers, a contaminant is first applied to the section of skin such that the contaminant is worked into spaces between cells in the top few layers of stratum corneum cells. The contaminant has a high absorption at or near at least one frequency band of light. Pulses of light at the at least one frequency band produced by a laser are then applied to a region of the section of skin. The light pulses are of an intensity and duration such that the contaminant absorbs enough energy with each pulse to cause cells from the top few layers to be exfoliated without causing significant harm to the layers of skin cells underneath. A transdermal drug delivery system, such as, for example, a patch, is then applied over the exfoliated region. Removing layers of the stratum corneum enables the drug in the transdermal delivery system to cross the skin barrier more easily.

In a further aspect, the invention provides a method of measuring a body function with an electrical skin sensor. The stratum corneum provides an electrically resistive barrier at the skin surface. In this method, several surface layers of the stratum corneum in a region of skin are first removed by the method described above. An electrical skin sensor is then applied to the region of skin and a body function is measured with the skin sensor. Removing surface layers of the stratum corneum lowers skin resistance and enables better electrical contact between the skin and the sensor.

In yet another aspect, the invention provides a device and method for imaging subsurface structures in a patient's skin. A highly light scattering medium, such as skin tissue, strongly attenuates the component of incident light that carries imaging information from deeply embedded objects. The attenuation results from the impossibility of focusing light in the scattering medium, the short penetration depth of incident radiation, and rapid attenuation with depth of light coming out of the medium without scattering. The device of the invention includes a confocal microscope including a source of coherent light having a wavelength in a range of about 800 to about 1000 nm, and a means of time resolving light backscattered from the skin of a patient. Time resolving the signal from the confocal microscope eliminates noise attributable to light multiply scattered from regions distant from the focal point of the confocal microscope, thereby improving the signal to noise ratio of the confocal microscope signal.

In yet another aspect, this invention provides a skin treatment system and process for increasing the tension and elasticity in a section of human skin. The system includes an energy absorbing material deposited in the dermis portion of the skin, and an illumination source spaced a predetermined distance from the skin for providing energy to be absorbed by the material. The energy absorbing material can be a graphite thread sewn into the skin, or carbon particles implanted by a tattooing technique. A useful energy absorbing material has an optical absorption of at least one frequency band of light emitted from the light source. The skin section can be illuminated with at least one frequency band of light, a significant portion of which penetrates the section of skin and is absorbed in the energy absorbing material. It is believed that this absorbed energy is transferred to adjacent dermal tissue causing small disturbances in the dermal tissue. It is further believed that the disturbances are repaired by a natural immune response of the skin creating new collagen fibers that provide added tension and elasticity to the skin section. In one embodiment, the energy absorbing material is graphite and the source of light is a Nd:YAG laser. The graphite may be deposited in the dermis in the form of a graphite thread, which can be sewn into the dermis. The graphite may also be deposited using tattoo techniques.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A through 2F demonstrate a bleaching process. Each figure shows a successive diagrammatic view of a section of skin with hair immediately prior to being illuminated with a pulse of light energy.

FIGS. 22A–22E illustrate different types of biodegradable carriers for the composition illustrated in FIGS. 20 and 21.

FIGS. 30A and 30C illustrate a pattern of grid lines. FIGS. 30B and 30D illustrate a graphite thread being inserted into the dermis in the pattern of the grid lines.

Like reference numbers and designations in the various drawings indicate like elements.

DETAILED DESCRIPTION

OVERVIEW

Figure 1:
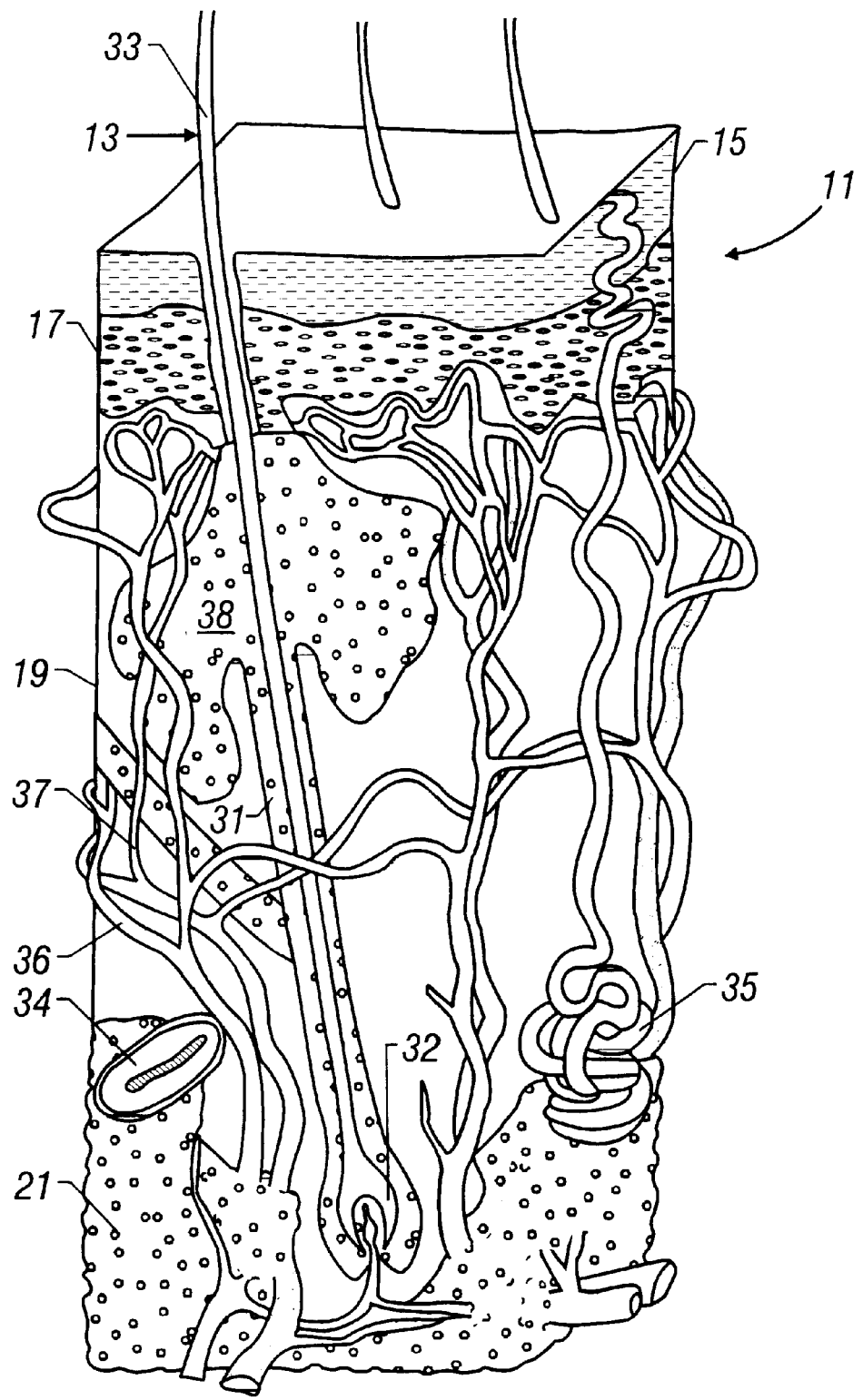
FIG. 1 is a section of human skin with a cross section of one hair.

Referring now to FIG. 1, a section of healthy human skin 11 includes a cross section of single hair 13. The surface of the skin 11 is composed of about 10–20 layers of dead and desiccated cells forming the stratum corneum 15. Below the stratum corneum 15 is the epidermis 17, and under that, the dermis 19 and subcutaneous basal cells 21. Hair 13 is rooted in the dermis 19 near basal cells 21, and includes a hair shaft 33, a hair duct 31, hair bulb 30, a nerve ending 34, a sweat gland 35, a sebaceous gland 38, arteries 36, veins 37 and a papilla 32. Melanocytes, which are interspersed among the basal cells of the hair bulb 30, have processes that extend into the matrix of the hair. Melanosomes containing melanin, a pigment are synthesized and passed on to the hair-forming cells of the hair shaft 33, and so are responsible for hair pigmentation.

In some of the methods described below, such as hair bleaching and hair removal processes, it is important to apply laser energy very preferentially to the regions of the skin in and around the hair follicles and to avoid causing general damage to the skin tissue. For example in hair bleaching processes, the follicles produce color in the hairs, i.e., the melanin in the melanosomes. In general, skin tissue other than the papillae should not be damaged to any significant extent. To avoid unwanted thermal damage to skin tissue it is necessary that the light used to illuminate the skin be absorbed in a body that has a much greater absorption coefficient than that of skin at the wavelength used.

Absorption coefficients for melanin and for various tissue components have been measured and reported in the literature. In determining the wavelength of light to be used for processes of the invention, such as hair bleaching and for hair removal as described below, a second useful parameter to consider is the "photon path length," which is the inverse of the absorption coefficient. For each combination of absorbent (i.e., melanin or other tissue component) and wavelength, there is a unique photon path length value. This value can be used to estimate the average distance a photon of a particular wavelength will travel through melanin or a skin component before being absorbed. In general, the shorter the photon path length, the greater the heat generated.

For comparison, estimates of the photon path length in melanin and various other skin components are given in Table 1 for photons from ruby, alexandrite, and Nd:YAG lasers, which produce a wavelengths in the range from about 0.694 to about 1.06 microns, respectively. The photon path length in the dermis for all three lasers is estimated to be in a range from about 3 to about 5 centimeters (30,000 to 50,000 microns). In the epidermis, however, photons of all three lasers are very readily scattered. Because of the scattering, the depth reached by a photon in the epidermis before its energy is absorbed is much smaller, typically only a few millimeters. As a result, most of the light beam energy is deposited in the skin in the form of heat between the surface and a depth of about 3 to 4 mm. For example, for photons having a wavelength in the range from about 0.6 to about 1.2 microns, the flux from laser illumination incident on the skin surface (the "incident flux") builds up at and just below the surface of the skin due to scattering of the photons by the skin tissue, but generally decreases with increasing depth. At depths in the range of 1 to 3 mm where most hair roots are located, the flux is about one half the incident flux.

TABLE 1

| | PHOTON PATH LENGTH | | |
|---|---|---|---|
| MEDIUM | Nd:YAG ($\lambda = 1.06\mu$) (microns) | Alexandrite ($\lambda = 0.755\mu$) (microns) | Ruby ($\lambda = 0.694\mu$) (microns) |
| Epidermis | 3,000 | 1,700 | 1,400 |
| Dermis | 30,000 | 50,000 | 50,000 |
| Blood | 500 | 2,500 | 1,400 |
| Melanin | 100 | 70 | 50 |
| Graphite | 0.1 | 0.098 | 0.097 |

Melanin has a large absorption coefficient compared to the absorption coefficients of epidermis and dermis at wavelengths of light between about 500 nm and about 1500 nm. Accordingly, the estimated photon path length in melanin, as shown in Table 1, is between about 50 and 100 microns for photons of wavelength of about 0.694 to about 1.06 microns. Because it so readily absorbs light, the energy absorbed by melanin from light in this wavelength range is many times greater than that absorbed by skin tissue. For comparison it is useful to note that the photon path length in graphite is only about 0.1 micron. Thus, in general, the heat generated by illuminating a skin section having hair ducts containing melanin with light beams in this range of wavelengths is substantially less than that generated by the same light beam if the hair ducts contain carbon particles, but substantially greater than that generated in skin by passage of an incident light beam there through.

Skin tissue can be devitalized or damaged if heated to a temperature of about 70° C. and maintained at that temperature for about 1 second. Higher temperatures can damage tissue in a shorter period, and temperatures between about 55° C. and about 70° C. for periods longer than 1 second can also damage tissue.

Heat energy diffuses relatively rapidly between light pulses, and the effects of each pulse is concentrated in regions of high photon absorption. In a rough estimation, $2 \times 10^{-4}$ J of energy absorbed in a 100 micron diameter sphere of tissue would heat the sphere of tissue by about 90° C. and that in about 0.01 seconds after illumination the heat energy would be dissipated over a 200 micron diameter sphere where the temperature increase would be down to about 10° C. In 0.1 second the heat would dissipate over a 300–400 micron diameter sphere and the temperature increase would drop to about 1°–3° C.

Several uses of laser light applied to the skin will now be described in detail. These include hair bleaching, hair removal, imaging subsurface skin structures, skin tightening, and preparing the skin for transdermal drug delivery and for measurement of body functions with skin sensors. Apparatus employed in these uses will also be described.

No. 1: HAIR BLEACHING

Unwanted body and facial hair is an important cosmetic concern for many people. Many people wish to remove body hair that is dark, either black or dark brown. This has been historically true in modern times for leg hair and facial hair on women, and for body hair generally on certain male athletes, such as competitive body builders. More recently, many men have taken to removing body hair, such as the hair growing from their backs, to obtain a more youthful appearance. Waxing is uncomfortable and not very long-lasting. Electrolysis can be also painful, slow and expensive. Bleaching the hair provides an alternative that makes hair less noticeable, and for many people bleached hair is unobjectionable.

This aspect of the invention provides a process for bleaching hair shafts containing melanosomes below the skin surface, substantially throughout the lengths of the hairs below the skin surface, as well as above the skin surface. Since the hair is bleached below the surface of the skin, in some instances all the way to the root, a period of several weeks or months may pass before hair with darker color appears above the surface of the skin. The method is intended for use on healthy human skin for cosmetic purposes. The process generally does not cause significant or lasting harm to living tissues that surround the hairs.

As will be described in fuller detail below, the hair bleaching method of the invention employs a light source that is highly absorbed in melanin or in melanosomes containing melanin, and which will penetrate the skin reasonably well. In general, light with wave-lengths between about 0.4 microns and about 1.5 microns will penetrate the skin and also be absorbed by melanin. To assist the light in reaching melanin located in portions of the hair shaft below the surface of the skin, the hair ducts are first filled with a fluid which is transparent to light at the wavelength being employed. The light is then directed at the skin in pulses having a pulse duration and fluence sufficient to destroy the melanin without causing significant damage to surrounding tissues. Light is transmitted through the fluid down the hair duct, and also scatters through the skin and thence to the hair duct, where it can penetrate the hair shaft and be absorbed by the melanin in the hair shaft. Light energy absorbed by the melanin causes the melanin to be destroyed, thereby bleaching the hair.

The first few pulses of light directed down the hair shaft into the hair duct and onto the skin surface contact melanosomes in the upper portions of the hair shaft so as to cause bleaching of the upper portions of the hair shaft. The bleaching of the upper portions permits additional photons to travel through the upper part of the hair duct to the lower portions of the duct, thereby bleaching the lower portions of the hair shaft. To obtain the most long-lasting results, the pulses of light are continued until the entire length of the hair shaft is substantially completely bleached.

There are two kinds of melanin in human hair: eumelanin and phaeomelanin. In general, black and brown hairs contain more eumelanin, while lighter colored hairs, such as red and blonde hairs, contain more phaeomelanin. White hairs have inactive melanocytes, which do not contribute melaninibearinig melanosomes to the hair root at all. It is not effective to attempt bleaching of "gray" hair that has become yellowed or otherwise discolored. Similarly, hair that has been artificially colored by a dye that absorbs light at a wavelength(s) other than those that are highly absorbed by melanin cannot be as effectively bleached using a light source that produces light highly absorbed by melanin. However, as one skilled in the art will appreciate, dye colors only the portion of the hair shaft above the skin surface. The method of hair bleaching disclosed herein can be used to bleach hair well below the skin surface, in some cases all the way to the hair root. Therefore, even artificially dyed hair that contains melanin in its natural state can be bleached at least below the skin surface using the method of this invention.

When light having a wavelength in the range between about 0.6 and about 1.2 microns is used to illuminate the skin surface, the light energy incident upon the skin surface is preferentially absorbed in melanin in hair ducts located at a distance of from about 3 to about 5 mm below the skin surface. The melanosomiies containing the melanin are heated to a temperature sufficient to damage, disrupt or vaporize the melanosomes and/or tissue surrounding them without substantial damage to other skin tissue through which the light passes and is scattered. As described above, tissue is devitalized or damaged if heated to a temperature of about 70° C. and maintained at that temperature for about 1 second. Higher temperatures can damage tissue in a shorter period, and temperatures between about 55° C. and about 70° C. for periods longer than 1 second can also damage tissue. Thus, the pulse duration, pulse repetition rate and light flucnice used in the hair bleaching procedure should be selected to avoid raising the temperature of skin tissues surrounding the hairs to these damaging ranges.

Refer now to FIGS. 2A–2F, which diagrammatically depict a section of skin 40 that contains a hairs 41, which are situated in respective hair ducts 42. Hairs 41 include melanosomes 43. FIGS. 2A–2F depict skin section 40 in a time sequence wherein each figure immediately precedes skin section 40 being illuminated by a single light pulse. Although only one hair 41 is shown in FIGS. 2A–2F, it will be understood that several hairs similar to hair 41 Call be growing in skin section 40, and that several hairs growing in a section of skin can be treated at the same time. Therefore, the following description will refer to a plurality of hairs 41 and associated structures rather than to a single hair 41. In addition, similar features as shown in FIGS. 2A–2F will be referred to with the same reference numerals in subsequent figures of the Drawing Skin section 40 can be first washed with soap and water and then rinsed with water, and dried with a cloth towel. Skin section 40 can be further cleaned with isopropyl alcohol or the like and allowed to dry.

To bleach hairs 41, a fluid 44 that is transparent to light, for example one that has an index of refraction substantially greater than that of skin tissue, which is about 1.37, is applied topically to skin section 40 with hairs 41 to be treated so as to cause fluid 44 to infiltrate into hair ducts 42 in skin 40. Fluid 44 should be transparent to light at or near at least one frequency absorbed by melanosomes, but which penetrates skin a few millimeters. Any method can be used to enhance penetration of fluid 44 into hair duets 42, such as, for example, gently rubbing skin 40 or employing ultrasound to work fluid 44 into hair ducts 42, and employing a surface active agent in fluid 44 to encourage penetration of fluid 44 into hair ducts 42 by capillary action. However, care must be taken to avoid any technique that will irritate hair ducts 42. If hair ducts 42 become irritated, the sebaceous glands in the duets will exude a wax-like substance that tends to plug hair ducts 42.

Preferably, transparent fluid 44 infiltrates throughout the entire length of hair ducts 42, but significant bleaching below the skin surface can also be achieved even when transparent fluid 44 does not infiltrate all the way to the bottom of hair ducts 42. If fluid 44 has an index of refraction substantially greater than 1.37, which is the index of refraction of skin tissue, the column of fluid 44 in each hair duct 42 conducts light similarly to an optical fiber. Light mineral oil has an index of refraction of about 1.47, which is significantly larger than the index of refraction of skin tissue. Therefore, a mineral oil-filled hair duct will conduct light as would an optical fiber. Light will reflect off the walls of hair ducts 42, but can penetrate into hair shafts 41, which will typically have an even higher index of refraction than fluid 44. The light penetrating hair shafts 41 can be absorbed by melanin in melanosomes 43 in hair shafts 41.

Fluid 44, such as mineral oil, is generously applied to skin section 40, for example, in a quantity of about one gram per 10 square centimeters. It is important that the oil infiltrate into hair ducts 42, preferably throughout their lengths. The oil can be massaged on the skin surface for a period of about 1 minute for each 10 square centimeters to encourage infiltration of the oil into hair ducts 42 in skin section 40. Skin section 40 can also be covered and allowed to rest for a few minutes after application of the oil before the illumination step commences.

After hair ducts 42 have been infiltrated with transparent fluid 44, skin section 40 containing the infiltrated hair ducts 42 is illuminated with short pulses of light that is well absorbed by melanin in melanosomes. The light must also be of a wavelength that is scattered by skin tissue, but which penetrates at least a few millimeters through skin.

Figure 3:
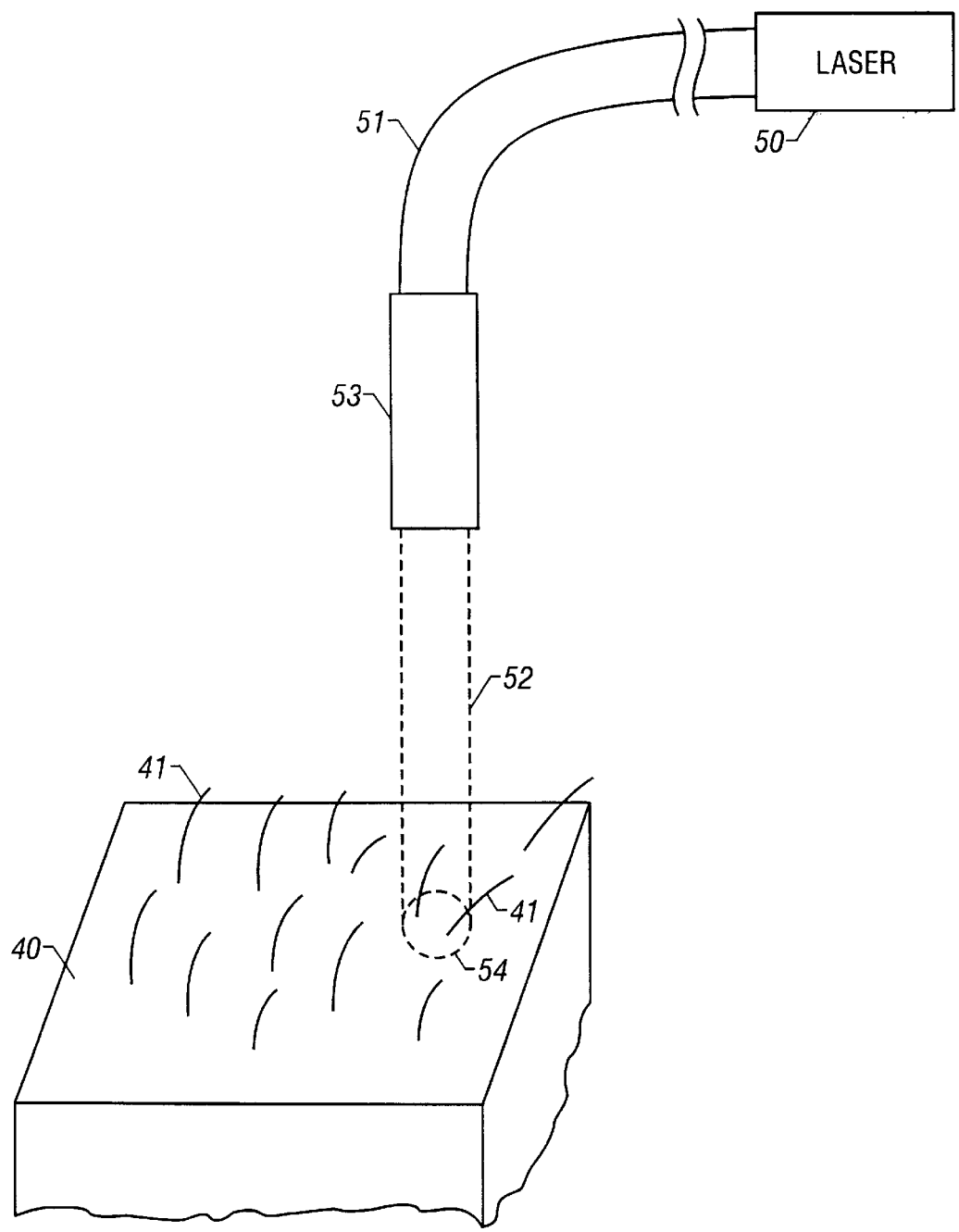
FIG. 3 is a diagram of a laser apparatus for use during different processes according to the invention.

Referring now to FIG. 3, an arrangement for applying pulsed light to skin section 40 is illustrated. A light source, such as a laser 50, provides pulses of light through a movable optic cable 51. The light pulses are emitted in a beam 52 through an endpiece 53, which is adapted to be held by the hand of an operator. Light beam 52 is directed at skin section 40 and covers a spot 54 having a size that is smaller than skin section 40 but large enough to include more than one hair 41. The operator moves endpiece 53 to scan beam 52 over different areas of skin section 40.

Referring again to FIGS. 2A–2F, light beam 52 is directed towards the skin surface so that a portion of beam 52 is conducted through fluid 44 in hair ducts 42, and is absorbed by melanin in melanosomes 43 in hair shafts 41. Aiming the light beam about normal to the skin surface can help to direct the light into hair ducts 42 alongside hair shafts 41 through the transparent fluid 44 that fills ducts 42. These photons are internally reflected by the walls of ducts 42 and transmitted down ducts 42. A portion of these photons eventually are absorbed by melanin 43 in hair shafts 41. Due to scattering of the photons within the skin tissue, another portion of the light, which is transmitted to ducts 42 through the skin tissue, is also absorbed in melanosomes 43 in hair shafts 41. The light absorbed by melanin in hair shafts 41 imparts sufficient energy to melanosomes 43 to damage, disrupt and/or vaporize them, thereby bleaching hair shafts 41.

Although beam 52 is applied in a direction such that portions of the beam enter the surface openings 45 of ducts 42, most of the photons in beam 52 are incident on the skin surface, pass through the epidermis of skin section 40, and scatter. The first pulse is typically absorbed in the upper portions of hair shafts 41. This causes bleaching of the upper portions of hair shafts 41, indicated in FIG. 2B by a decrease in melanosomes 43 in the upper portion of hair shafts 41. It is believed that the bleaching of the upper portions decreases absorption in these regions and permits additional photons to travel to the lower portions of ducts 42. As the hair shafts 42 are bleached near the skin surface, the absorption in the hair shafts 42 is greatly reduced in the bleached regions, permitting photons from subsequent pulses to travel deeper into ducts 42. Fluid-filled ducts 42 conduct light similar to optical fibers. The deeper penetrating photons bleach successively lower portions of hair shafts 41, illustrated in FIGS. 2C–2F. Regions of hair shafts 41 that have been bleached appear to scatter light with greater efficiency. The process is continued until hair shafts 41 are substantially completely bleached (FIG. 2E). The number of pulses needed to completely bleach a hair depends on the fluence and wavelength of the light. The higher the fluence, the fewer pulses are needed.

Clinical tests using mineral oil infiltrated into hair ducts between the outside walls of hair shafts and the inside walls of their respective hair ducts have confirmed the bleaching process as depicted in FIGS. 2A through 2F. These tests have also confirmed that unless oil is infiltrated into the hair ducts, bleaching generally occurs only in a region of the hair shafts above the skin surface.

Transparent fluids that are useful in the practice of this invention include any light mineral oil, NF, Such as DRA-COL™ 5 to 13, or transparent gel lubricants, many of which may contain surface active agents that help the fluid infiltrate the hair duct. Fluids other than mineral oil can also be employed, such as, for example, baby oil, peach oil, and tea tree oil, SO long as the index of refraction of the fluid exceeds that of skin tissue.

Figure 4:
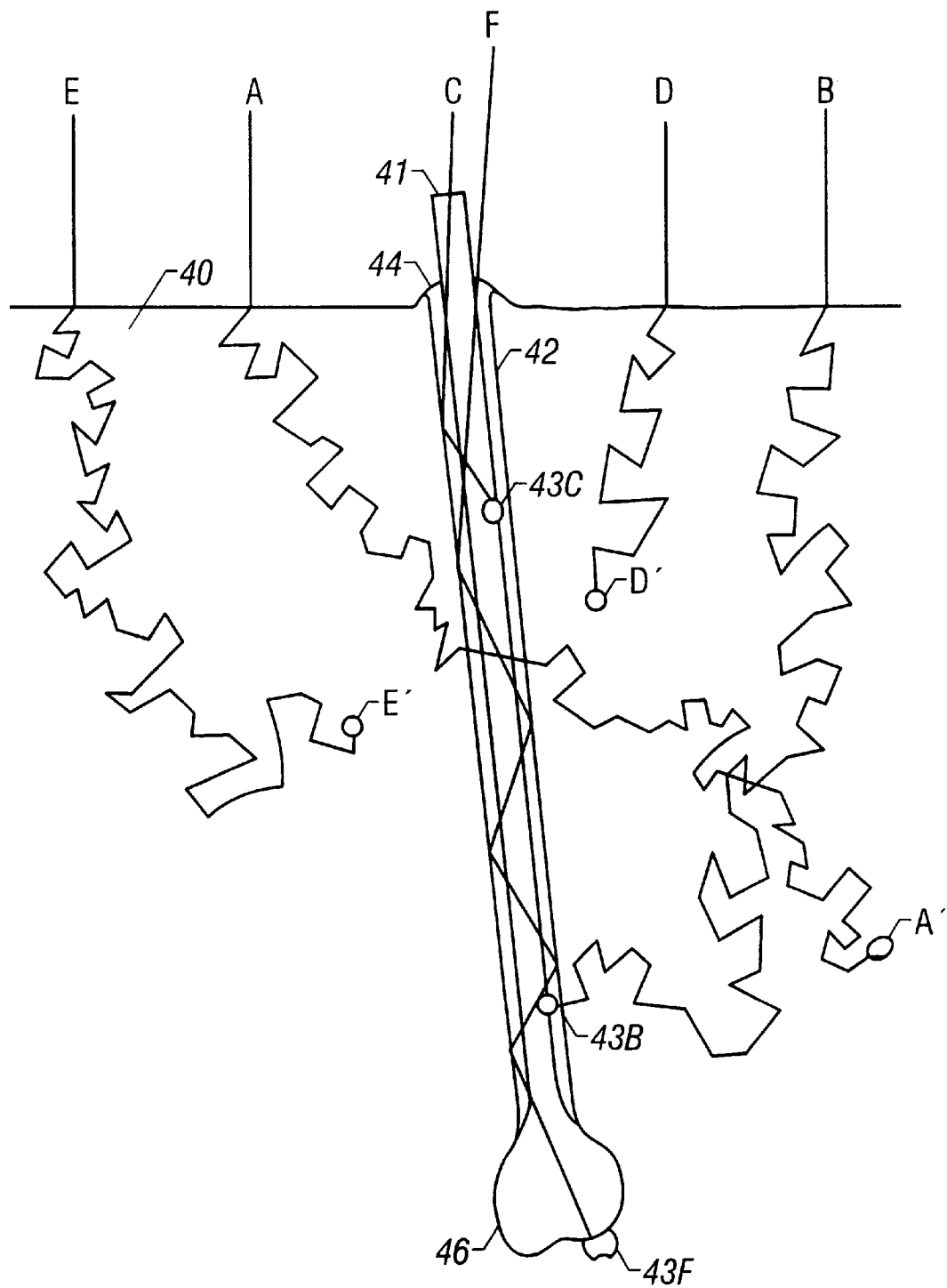
FIG. 4 is a diagram depicting the paths of photons in a skin section during a typical bleaching process of the invention.

FIG. 4 diagrammatically depicts photon absorption in a section of skin 40. Photons A, D and E that are incident on the surface of skin 40 scatter in skin 40, and are ultimately absorbed in skin tissue at respective locations A', D' and E' distant from hair shaft 42. Photon B scatters in skin 40, and is absorbed in a melanin granule 43B in hair shaft 41. Photon C travels partially down hair duct 42 through mineral oil 44, and is absorbed in a melanin granule 43C in hair shaft 41. Photon F travels all the way down hair duct 42, and is absorbed in a melanin granule 43F in the bulbous portion of papilla 46.

Thus, bleaching of hair shafts 41 and papillae 46 is obtained by absorption of photons from two sources—those photons transmitted through fluid 44 in ducts 42 and those photons scattered through the skin which eventually reach the hair shafts 41 and papillae 46. The combination of the two processes enables use of lower beam fluences than would otherwise be necessary were ducts 42 not filled with high index of refraction fluid 44.

In general, the above considerations show that light at a wavelength of between about 0.4 microns and 1.5 microns will penetrate skin tissue reasonably well, and be reasonably well absorbed in melanin in mclanosomes. This frequency band extends into both the visible and near infrared ranges of the electromagnetic spectrum. Especially good transmission in skin is obtained with wavelengths between 0.6 microns and 1.3 microns. Short pulses of light having sufficient energy to disrupt or vaporize the melanosomes are used. The pulse duration should be shorter than the thermal relaxation time of melanin, which is about 1 $\mu$s. The beam fluence should be in a range of about 0.1 $J/cm^2$ to about 10 $J/cm^2$, but this can vary depending on the wavelength of light used.

Figure 5:
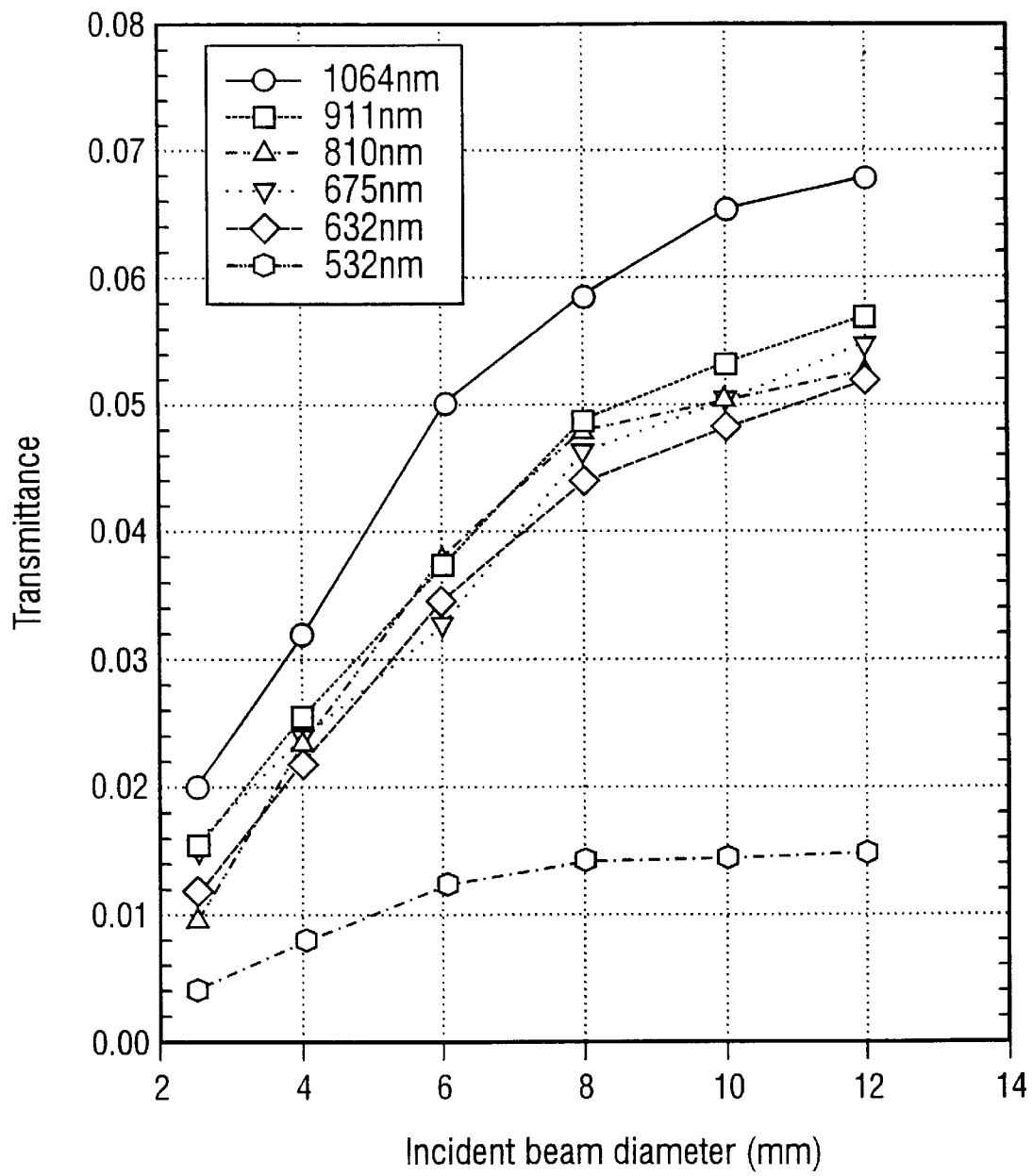
FIG. 5 is a graph of light transmittance plotted against beam diameter for different wavelengths of light.

The beam diameter should be large enough to obtain deep penetration of light into the skin. Refer now to FIG. 5, which graphically plots the transmittances of collimated light at different wavelengths through skin tissue in, vivo as a function of incident beam diameter. The skin type used was Caucasian male, the anatomic site was skin tissue located between fingers, and the tissue thickness was about 3.4 mm. The graph shows that the transmittance generally increases with increasing wavelength, and for each wavelength, increases with increasing incident beam diameter up to about 8–12 mm before beginning to level off. Therefore, the beam diameter should be about 8–12 mm.

Any type of light having a wavelength in the range from about of 0.4 micron to about and 1.2 microns, including that provided by a high intensity lamp, is highly absorbed in melanin, yet is well scattered in skin tissue. Therefore any source that produces light having a wavelength within this range can be used in the practice of this invention. Appropriate filters can be used to select desired wavelengths. Many other wavelengths of light could be utilized so long as the light penetrates skin fairly well and also is reasonably well absorbed in melanin. The preferred sources of light are alexandrite, ruby and Nd:YAG lasers, which provide light having a wavelength in the range from about 0.694 µm to about 1.06 µm. Experiments utilizing each of these three laser light sources are described in the Examples below.

EXAMPLE 1

Alexandrite Laser

In this embodiment, an alexandrite laser 50 operates at a wavelength of 0.755 micron with a beam cross sectional area of about 0.5 cm$^2$. Controls on laser 50 permit adjustment of pulse duration as short as 0.5 ns at low pulse power using a Q switch and a longer pulse duration of greater than 100 µs in a non-Q switch mode. Pulse energy can be adjusted to between 0.01 J and 5 J. Alexandrite lasers meeting these specifications are available from Light Age, Inc. of Somerset, N.J.

As discussed above, the illumination should be sufficient to achieve hair bleaching without significantly damaging surrounding skin tissue. A pulse duration of about 10 ns, pulse energy of 1.2 J, beam cross sectional area of about 0.8 cm$^2$, and repetition rate of about 1–10 Hz provides beam 52 with a pulse intensity, or fluence, of about 1.5 J/cm$^2$. Beam 52 scatters well and is absorbed relatively poorly in skin tissue. However, substantially all of the beam energy is ultimately absorbed in the skin between the surface and a depth of about 0.5 cm. Each section of skin is illuminated for about six or so pulses.

With the illumination parameters given above, about 12 J of energy is delivered to a skin section of 0.8 cm$^2$ in one second, while most of the illumination energy will be absorbed, some will also be reflected from skin 40. There is very little general heating of skin 40. Skin to a depth of about 0.5 cm is heated by about 10° C. above normal skin temperature, or to about 33° C. At this temperature, the skin hardly begins to feel warm, and there is no pain and no significant damage to skin 40.

There are about $2 \times 10^{18}$ photons in a 1 Joule pulse of light at a wavelength of 0.755 micron. If, for example, the cross-sectional area of the beam incident on the skin is 0.5 cm$^2$, and the opening of the hair duct is only about 0.00008 cm$^2$, then about $3 \times 10^{14}$ photons enter directly into the hair duct. Therefore, about $1.5 \times 10^{-4}$ Joule of energy enters the hair duct, and this is sufficient energy to increase the temperature of a 100 micron sphere of tissue (about the size of a papilla) to about 75° C.

EXAMPLE 2

Ruby Laser

Another embodiment of the present invention utilizes a ruby laser, which produces a laser beam having a wavelength of about 0.694 micron. The beam from a ruby laser is absorbed about twice as efficiently in melanin, and about four times more efficiently in the blood of the tiny blood vessels of the papillae, as is the beam from an alexandrite laser. Ruby lasers are commercially available. This embodiment employs a 10 mm diameter beam at a beam pulse energy density, or fluence, of about 1 J/cm$^2$, using a 10 ns pulse at a frequency of 10 pulses per minute. Up to about 20 pulses can be provided to a skin section before allowing the skin to cool down. This is more than sufficient in most cases to effect bleaching of the hair 41.

EXAMPLE 3

Nd:YAG Laser

A Nd:YAG laser can also be used for practicing this invention. Photons produced by a Nd:YAG laser, which has a wavelength of about 1.06 micron, are more readily absorbed in blood, but less readily absorbed in melanin than are those from an alexandrite laser. Absorption in melanin is only about 40 percent that of a ruby laser. Nd:YAG lasers are commercially available from many sources. Effective hair bleaching is obtained employing a pulse duration of about 10 ns, a beam diameter of about 10 mm, and a beam pulse fluence of about 2 J/cm$^2$. Only a few pulses should be necessary to effect bleaching.

Additional pulses may be provided to deliver light energy to the melanin in the papillar region. If there is sufficient melanin or other absorbers in the papillar region, it may be possible to deliver sufficient energy there to damage the hair and inhibit or prevent future hair regrowth. For this purpose it is important to use light at a wavelength that will provide high absorption in the papillar region. In addition, longer pulses of light with higher beam fluences can be used to thermally damage papillae, as described in the following examples. These beams generally do not cause explosion of the melanosomes in the papillae, as the energy is transmitted over a time period greater than the thermal relaxation time of the melanosomes. However, energy from photon scattering through skin tissue proves a sufficient boost to energy absorbed in melanin from photons traveling down the hair duct to damage the papillar region sufficiently to reduce future hair growth.

It is important that the hair ducts remain open and unobstructed during illumination. For some subjects, it may be necessary to stretch the skin in at least 3 directions in order to assure that the hair ducts remain open from the skin surface to the papillae during illumination.

As described above, the photon flux is highest very near the skin surface due to light scattering in the epidermis and dermis. As a result there is preferential heating in the skin at its surface, as compared to deeper layers of the skin. This heating is undesirable, and can be controlled by cooling the skin surface, either prior to or during the illumination, or both. Methods of cooling the skin surface can include, but are not limited to, direct or indirect application of rapidly flowing ambient air, cold air, compressed nitrogen, or ice packs. One method is to use a chilled fluid, such as cold mineral oil, in the process described above and to reapply chilled fluid periodically during the process.

Different types of cooling apparatuses that can be employed in conjunction with this hair bleaching process and other processes that illuminate the skin with laser light are described in greater detail below in Section 7 with reference to FIGS. 23–28. These cooling apparatuses generally include a transparent sapphire window that is placed in contact with the skin during illumination. The window is supported by a structure that includes a heat exchanger, and that provides a passage for light to pass through the window to the skin underneath. Heat from the skin is absorbed by the window and removed from the window by the heat exchanger.

In this aspect of the invention the goal is to bleach hair rather than to remove it or substantially inhibit its growth. One advantage of using the described short-pulse light parameters to bleach hair is that the bleached condition is not permanent. As the treated hairs continue to grow, new melanosomes will be generated, and the new growth of hair will revert to a natural hair color. The natural reversibility of the bleaching process is particularly desirable among males who may wish to bleach their facial hairs to avoid the need to shave daily, but who do not want to permanently lose the ability to grow a beard, should they desire to do so.

Another advantage is that hair is bleached below the surface of the skin, so that a colored portion of the hair will not be visible until new growth emerges from the skin surface. The regrowth can then be bleached to remove its color before it emerges from the skin surface. By repetition of the bleaching process at spaced intervals of a few weeks, the problem of "dark roots" showing at the base of the bleached hairs can be eliminated.

In addition, the laser conditions required to bleach hair are generally milder than those used to hinder hair growth, so there is less risk of damage to skin tissue in laser hair bleaching than in laser hair removal procedures.

No. 2: HAIR REMOVAL USING TRANSPARENT FLUID IN EMPTY HAIR DUCTS

Another way to deal with unwanted hair is to destroy the hair so as to inhibit its regrowth. This aspect of the invention provides a method for the permanent or long term removal and inhibition of regrowth of unwanted human hair. In this method, hair growing in hair ducts in a section of skin is first extracted, for example, by waxing. Then, a fluid is infiltrated into the empty hair ducts in the section of skin. The fluid is substantially transparent at a frequency band of light that will penetrate at least a few millimeters through skin tissue and that is at least reasonably well absorbed in a naturally occurring chromophore, such as, for example, melanin or blood. The fluid should also have an index of refraction that is greater than that of skin tissue. Then, the section of skin is illuminated with a beam of light at the frequency band, the beam being directed such that portions of the beam enter fluid-filled surface openings of hair ducts in the skin section. A small portion of the beam enters the ducts and is transmitted through the transparent fluid to the papillae where a substantial portion of it is absorbed in the naturally-occurring chromophores. The major portion of the beam scatters in the skin tissue. This causes general heating of the skin tissue, including skin tissue in the regions of the papillae.

The illumination is limited so as to avoid general overheating of skin tissue. In this embodiment, the skin is heated generally to temperatures in the range of about 40° C. to 48° C., which is close to but below the pain threshold and also below the damage threshold for skin tissue. The melanin, blood cells or blood vessels, or other naturally occurring chromophores of the papillae preferentially absorb the photons traveling down the hair shafts. The illumination is chosen to raise the temperature of papillae to at least about 70° C. with each pulse of light. This is generally sufficient to devitalize papillar tissue. There is no significant damage to skin tissue other than tissue in the immediate vicinity of the papillae. The skin section can be allowed to cool down before repeating the illumination. By also actively cooling the skin, either during illumination and/or between illumination pulses, a greater amount of light energy can be applied to destroy papillae by absorption of the light in the chromophores without excessively heating the skin. The illuminating and cooling can be repeated several times to devitalize the hair.

In one aspect of this hair removal process, long pulse laser energy is applied in a manner so as not to vaporize the melanin in the melanosomes in the papillar region. Light with wavelengths of between about 400 nm and about 1500 nm can be used. Wavelengths between about 600 nm and about 1300 nm appear to work best. The pulse duration should be longer than the thermal relaxation time of the naturally occurring absorber, such as blood vessel in the papillar region or melanin. The pulse duration can range between about 100 $\mu$s and about 200 ms, and a pulse duration in the range of about 10 ms to about 100 ms is best. The beam diameter should be large enough to obtain beam penetration through the skin that is deep enough to reach the bottoms of the papillae. Such beam diameters can be in the range of about 8 mm to about 12 mm. The pulse energy density, or fluence, is high enough to thermally denature tissue surrounding the natural follicular absorbers, such as the melanin or blood vessels. These fluences can be in a range of about 3 J/cm$^2$ to about 300 J/cm$^2$.

Merely vaporizing the melanin in the hair shaft or papilla nominally does not significantly damage the skin's ability to grow hair. As described above in Section 1, vaporizing the melanin in melanosomes bleaches the hair and the hair can continue to grow. If the bleached hair falls out or is pulled out, it is quickly replaced by another hair from the same papillae. In the presently described method, on the other hand, heat is applied relatively more slowly to the skin. This takes advantage of the naturally occurring absorber's relatively high absorption of skin penetrating photons. Care is taken to not heat the melanin to temperatures high enough to merely cause bleaching.

Alternatively, the illumination can be applied with shorter pulses, with pulse durations in a range between about 5 ns to about 50 ns, but with sufficiently high intensity pulses to vaporize or otherwise utterly destroy or damage the natural absorber, and with enough energy to cause more extensive damage to surrounding tissue than in the bleaching process. These pulses are much shorter than the thermal relaxation time of, for example, melanin. When applying short pulses of light, the flucnice should be in a range of between about 0.1 J/cm$^2$ to about 10 J/cm$^2$, and more preferably between about 1.5 J/cm$^2$ to about 5 J/cm$^2$. The beam diameter should be between about 8 mm and 12 mm. The mechanism of damaging or destroying the viability of hairs is different from the first described method. Instead of generally heating the papillar region, the violent destruction of the absorbers causes damage to nearby regions around the papillae. Because hairs are first removed, the illuminated photons are not absorbed by the hairs before they can reach the papillar region.

These hair removal methods are similar to the above-described hair bleaching method in that a transparent fluid having an index of refraction that is greater than that of skin tissue is used to help conduct light in hair ducts. It is the combination of damage caused by light transmitted down through the fluid and by light scattered by through skin tissue that ultimately devitalizes the hairs. In the long pulse, thermal method, general heating of the skin tissue by light scattered through the tissue is combined with more intense heating of the papillar region by light transmitted down the ducts through the fluid. In the short pulse regime, it is more likely that the papillar regions are damaged by exploding or vaporizing absorbers in the papillar region that absorb photons transmitted through the ducts and scattered through the skin tissue.

Figure 6:
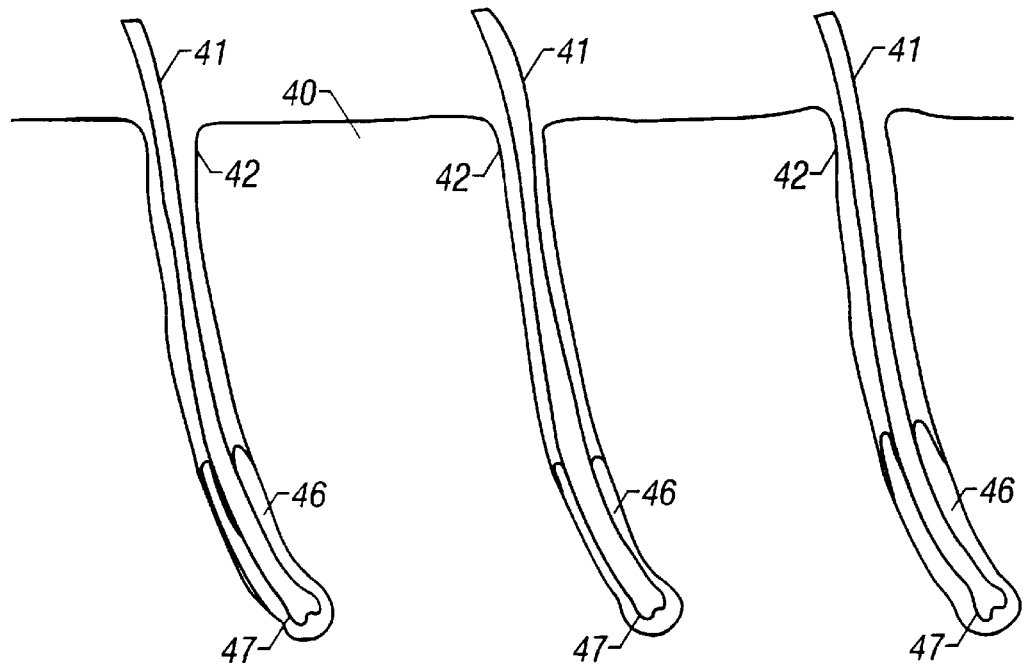
FIG. 6 is a diagram of a section of skin with three hairs.

Referring now to FIG. 6, a section of skin 40 includes three hairs 41 growing in hair ducts 42. Hairs 41 grow from follicles 46, which extend partially up through ducts 42 from respective bulbous regions 47 at the base of hairs 41. Skin section 40 can be first washed with soap and water, then rinsed with water, and dried with a cloth towel. Skin section can be further cleaned with isopropyl alcohol or the like and allowed to dry.

Figure 7:
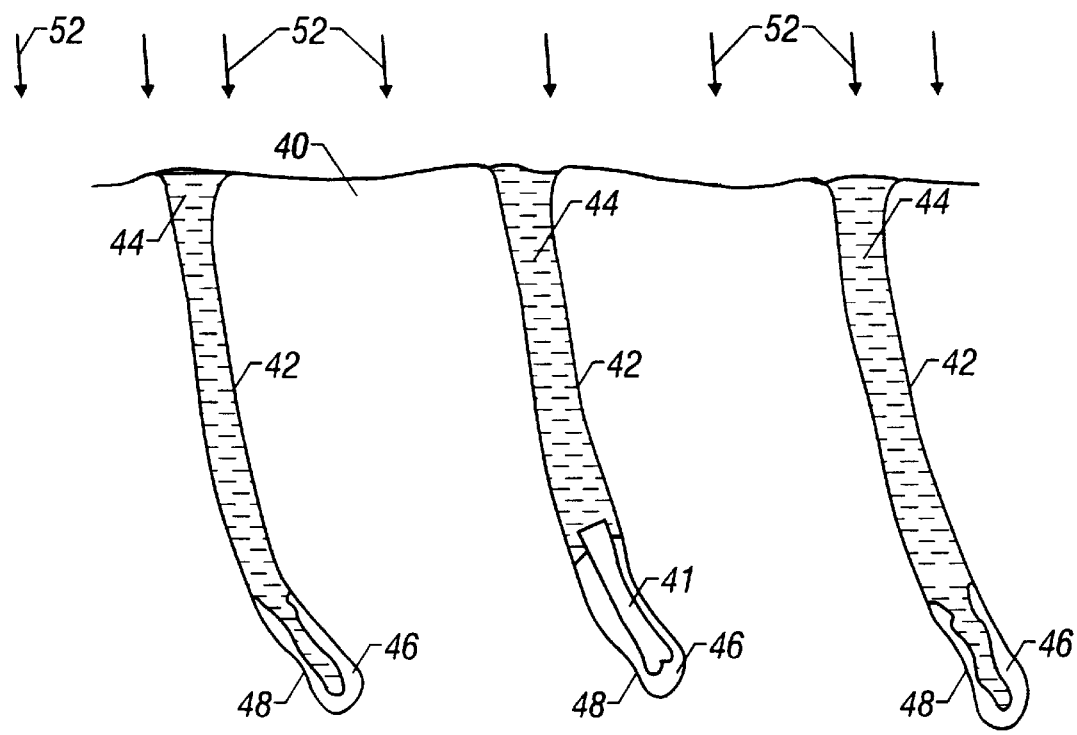
FIG. 7 is a diagram of the section of skin of FIG. 6 with the hairs removed and the hair ducts filled with a clear fluid.

The next step is to physically remove hairs 41 from hair ducts 42 in skin section 40. This can be done by using a commercially available hair removal wax product, for example, NATURE'S OWN PINE WAX™, which is marketed by Select Spa Source of Sausalito, Calif. The waxing procedure recommended by the manufacturer should be followed. Referring now to FIG. 7, waxing removes many hairs 41 completely, however, some of hairs 41 break off above the hair root and are only partially removed, as shown by the middle hair 42. Some hairs, such as hairs which did not extend beyond the surface of skin 40 prior to the waxing step, may remain intact after waxing. The partially removed and intact hairs may require a second treatment at a later date.

Next, mineral oil 44, or another transparent fluid with an index of refraction that is greater than that of skin, is topically applied to skin section 40. Oil 44 is applied in quantities of about 0.1 gram/cm$^2$. Oil 44 is massaged thoroughly on the skin surface for a period of about one minute to cause as much of the oil as possible to infiltrate into hair ducts 42 in skin section 40. It is believed that in most cases oil 44 penetrates to the bottoms of hair ducts 42. FIG. 7 shows hair ducts 42 filled with oil 44.

The next step is to illuminate skin section 40 with pulses of light at a wavelength that is well absorbed by one or more naturally occurring chromophores in follicles 46 or in tissue 48 surrounding and nourishing follicles 46. Such light absorbent chromophores can be melanin or hemoglobin, however, the invention is not limited to these two chromophores. The light used should also penetrate well through skin.

Light can be applied with a beam 52 produced by a laser 50, as shown in an arrangement similar to that illustrated in FIG. 3. The light producing arrangement in this hair removal method differs from that shown in FIG. 3 in that skin section 40 has hairs 42 removed before light is applied. Laser 50 provides pulsed coherent light through movable optical cable 51. Pulsed light beam 52 emerges through endpiece 51, which is held by an operator.

As indicated above, the present invention provides a process of illumination with the objective of achieving maximum destruction of hair growing potential with minimal damage to skin tissue in general. Specific examples of embodiments employing light with different characteristics will now be described in detail.

EXAMPLE 4
Long Pulse Alexandrite Laser

In this example, the illumination is provided by an alexandrite pulsed laser operating at a wavelength of 0.755 micron with a beam diameter of about 10 mm, providing a cross sectional area of about 0.8 cm$^2$. Controls on the laser permit selection of pulses as short as 0.5 ns at low pulse power using a mode-locked Q switch and a long pulse duration of greater than 100 microseconds in a non-Q switch mode. Pulse energy can be adjusted to between 0.01 J and 5 J. Alexandrite lasers meeting these specifications are available from suppliers such as Light Age, Inc. with offices in Somerset, N.J.

The objective is to heat the skin tissue of the papillar area to temperatures high enough to prevent hair growth. We target papillae 46 in skin section 40 and skin tissue 48 within a distance of about 100 to 200 microns immediately surrounding papillae 46. We select pulse duration of 100 ms, a beam cross section of 0.8 cm$^2$, a repetition rate of up to about 5 HZ, and a pulse intensity or fluence of about 80 Joules/cm$^2$. The 0.755 micron beam is scattered very well and absorbed relatively poorly in skin tissue. However, substantially all of the beam energy entering the skin is ultimately absorbed in the skin between the surface and a depth of about 0.5 cm. Each section of skin section 40 is illuminated for about 1 to 5 pulses. About three pulses are typically sufficient to devitalize hairs 41. Beam 52 is aimed to direct the maximum possible portion of beam 52 into the openings at the tops of hair ducts 42, understanding that this is still a very small portion of the total energy in the beam. Most of the beam passes through the epidermis into the dermis of the skin and heats the skin in general. Three pulses, of about 80 Joules/cm$^2$ each, deliver about 240 J/cm$^2$ into the skin.

This energy input is large enough to cause general damage to skin tissue. Therefore, the illuminating should only be done while steps are taken to cool the illuminated section of skin. A cooling apparatus, such as any one of the devices illustrated in FIGS. 23–28, can be used to help cool the skin during illumination. With active cooling, the skin can begin to feel warm but there will be no damage to the skin and normally no pain. If the cooling is insufficient or too much illumination is applied, the subject can experience pain before the illumination causes general damage to the skin tissue. Subjects should be instructed to let the laser operator know if the subject feels pain and in such event the operator should stop the illumination of that skin section immediately.

A portion of pulse laser beam 52 is transmitted down hair ducts 42 through transparent mineral oil 44 that fills ducts 42. For beams 52 directed at skin section 40 in a direction approximately parallel to the axis of hair ducts 42, we estimate that about 50% to about 70% of the light incident on the openings of ducts 42 may be transmitted to papillar areas 46 at the bottom of the duct. Mineral oil has an index of refraction of 1.47 which is larger than that of skin tissue, which is 1.37. The mineral oil 44 filled hair ducts 42 will conduct light somewhat like optical fibers as indicated in FIG. 4, but without scattering or absorption by hairs 41 within ducts 42.

The papillar area 48 of the skin of many people contains an abundance of melanin and small blood vessels which absorb 0.755 micron light substantially better than dermal tissue in general. The combined result of photons transmitted down hair ducts 42 and photons scattering through skin section 40 to the papillar regions 48 is a substantial preferential heating of papillae 46 and surrounding skin tissue 48 in the immediate vicinity of papillae 46. We estimate the total temperature rise in and immediately around the papillae to be in the range of about 30° C. to about 90° C. during each of the 100 ms pulses. Each pulse independently causes damage to the hair. These pulsing temperature increases are in addition to a smaller, more widespread temperature rise due to scattering and absorption of light in skin section 42 and can damage tissue in the papillar region 48 sufficiently to prevent or inhibit hair regrowth.

A very important element to the present invention is the control of energy input to the skin tissue. As indicated above the skin cannot be generally heated above about 65° C. for even one second without risk of general damage of the skin tissue. The tissue in and immediately around papillae 46 should be heated at the proper rate. If heat is applied too slowly, heat will dissipate to other regions and tightly controlled preferential tissue destruction will not be possible. The 100 ms pulses are long enough that the melanin in the melanosomes of papillae 46 can dissipate heat to the surrounding tissue 48 in the region of papillae 46 as the energy is being absorbed so that the temperature of the melanosomes does not reach an explosive temperature. This means that after allowing skin section 40 a few minutes to cool down the process can be repeated with additional damage to the papillar area. The process can be repeated about 6 to 10 times, allowing at least about 3 minutes for each skin section 40 to cool down before repeating the treatment of the same skin section 40. Using a cooling device also helps to keep the temperature of the skin within a safe range.

A single 10 nanosecond pulse above about 2.5 to 4 Joules/cm$^2$ would likely explode the melanosomes which in effect bleaches the tissue containing the melanin so that the absorption of additional energy is greatly reduced. The quick bleaching of the tissue usually does not appreciably damage the tissue. If such short pulses are used they should preferably be used as the last phase of the illumination phase of the process.

Because the photon flux is highest very near the skin surface, there is preferential heating at the surface as compared to deeper layers of the skin. This preferential heating can be countered somewhat by cooling the surface either prior to or during the illumination. Methods of cooling include use of rapidly flowing ambient air, cold air, compressed nitrogen and ice packs. One method is to use cold mineral oil in the process described above and to replace it periodically during the process. Skin section can also be actively cooled by employing a heat exchanger having a light-transmitting window on skin section 40 during illumination. Embodiments of suitable heat exchangers are described in greater detail in Section 7 below. Employing an active heat exchanger can allow more light energy to be applied to skin section 40 without causing general damage to the skin.

EXAMPLE 5
Long Pulse Ruby Laser

Another embodiment of this hair removal method utilizes a laser which produces a 0.694 micron wavelength laser beam 52. This wavelength is absorbed about twice as efficiently in melanin and about four times more efficiently in the blood of the tiny blood vessels of the papillar region as compared to the 755 nm wavelength alexandrite laser beam. Ruby lasers produce light at this wavelength and are commercially available. For this wavelength of light, a pulse fluence of about 60 J/cm$^2$, a pulse duration of about 100 ms, a beam diameter of about 10 mm, it a frequency of about 10 pulses per minute are illumination characteristics that should be effective for removing hair. As with the long pulse alexandrite laser beam, about 1–5 pulses are usually sufficient to devitalize or otherwise damage the hairs.

EXAMPLE 6
Long Pulse Nd:YAG Laser

The Nd:YAG laser can also be used for practicing this invention. The absorption of its 1.06 micron photons in blood is better than that for the alexandrite beam. Nd:YAG lasers are available from many sources. The laser can be operated to provide 120 J/cm$^2$ pulse fluence with a 100 ms pulse duration and a 10 mm beam diameter. These beams should not cause explosion of the melanosomes in the papillae, but energy absorbed in the papillar melanin and blood vessels from photons traveling down the hair duct through the transparent mineral oil, combined with energy absorbed from photons scattering through the skin tissue, is sufficient to cause sufficient damage to the papillar region to satisfactorily reduce future hair growth. About 1 to 5 pulses al-e applied to each region of skin section 40 to cause such damage.

EXAMPLE 7
Short Pulse Alexandrite Laser

In this mode, the alexandrite laser is operated with a beam pulse fluence of about 3 J/cm$^2$, a beam diameter of about 10 mm, and a pulse duration of about 10 ns. About 1–5 pulses are needed to cause sufficient damage to the papillar region to devitalize the hair or otherwise inhibit its regrowth.

EXAMPLE 8
Short Pulse Ruby Laser

The ruby laser is operated with a beam pulse fluence of about 2 J/cm$^2$, a beam diameter of about 10 mm, and a pulse duration of about 10 ns. About 1–5 pulses are needed to cause sufficient damage to the papillar region to devitalize the hair or otherwise inhibit its regrowth.

EXAMPLE 9
Short Pulse Nd:YAG Laser

The Nd:YAG laser is operated with a beam pulse fluence of about 4 J/cm$^2$, a beam diameter of about 10 mm, and a pulse duration of about 10 ns. Again, about 1–5 pulses are needed to cause sufficient damage to the papillar region to devitalize the hair or otherwise inhibit its regrowth.

For some subjects it may be helpful to stretch the surface of the skin in at least 3 directions in order to assure that the hair ducts remain open from the skin surface to the papillae. Instead of removing the hair from the skin section with wax, a depilatory could be used or the hairs could be extracted by plucking. Depilatories normally dissolve the portion of the hair above the skin surface and for about 1 mm below the surface. This would leave a large percentage of the hair shaft intact within the duct. However, for some subjects who object to the pain associated with the wax treatment, this could be a preferred method of practicing the invention. After the depilatory step the remainder of the process is as described above with a mineral oil application and illumination to devitalize the hair.

To improve transmission through the hair duct with portions of the hair remaining in the hair duct, it is suggested that only one or two very short, high energy pulses be used to bleach the melanin in the hair shaft to reduce absorption in the hair shaft. This could permit subsequent long pulse beams to travel down the duct to the papillar region. The challenge is to bleach the melanin in the hair shaft without bleaching the melanin in the papilla.

Many other frequencies of light could be utilized; however, preferably the light used should penetrate skin at least fairly well and also be reasonably well absorbed in the tissue in the papillar region. Any of the frequencies between those frequencies corresponding to wavelengths of 0.4 microns and 1.5 microns should work to some degree, but the 0.6 to 1.2 micron window is preferred. This invention is not restricted to laser beams. For example, high intensity lamps could be used. Appropriate filters could be used to select desired wavelengths. Many fluids other than mineral oil will work. As indicated above, preferred fluids will have an index of refraction greater than that of skin tissue, which is about 1.37. Other preferred fluids specifically include baby oil, peach oil and tea tree oil.

No. 3: HAIR REMOVAL WITH HAIR DUCTS ACTING AS LIGHT PIPES

This method of inhibiting growth of hair from papillae located at the bottoms of hair ducts in a section of skin is similar in most respects to that described above in Section 2. In that method, naturally occurring chromophores were used as light absorbent materials to absorb energy from light applied to the skin. In this method, however, a light-absorbent contaminant is introduced into hair ducts after hairs are removed from section of skin. Methods of hair removal using a contaminant and laser light arc described in U.S. Pat. Nos. 5,226,907 and 5,425,728.

Figure 8:
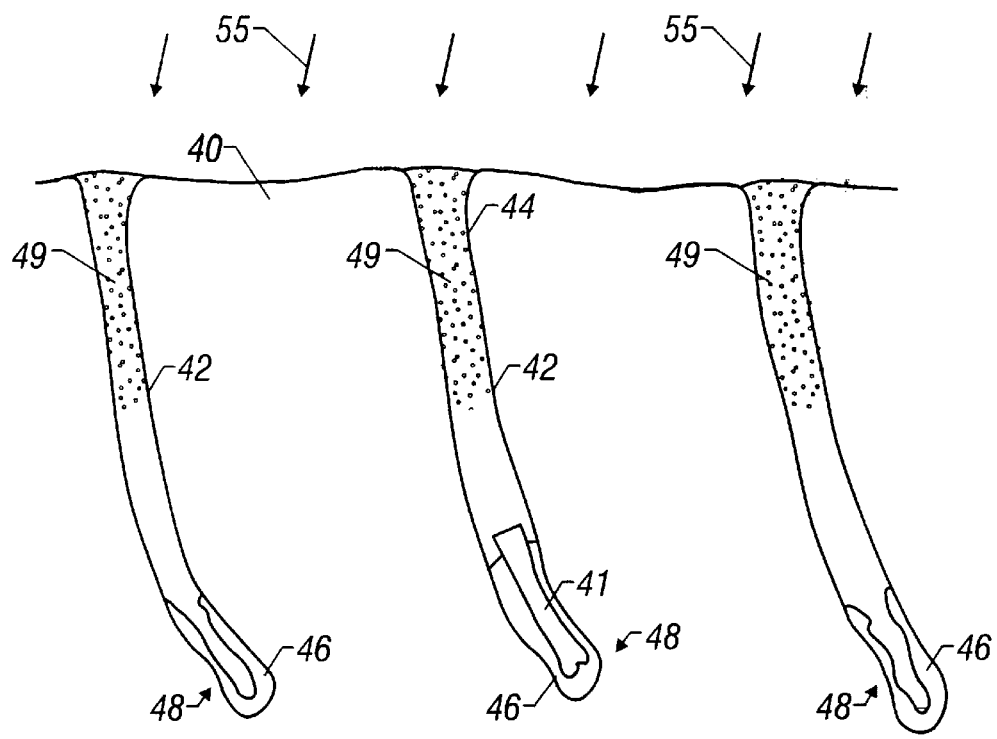
FIG. 8 is a diagram of a section of skin with three hairs removed from hair ducts, the hair ducts being filled with a light absorbing contaminant for a hair removal process according to the invention.

Referring now again to FIG. 6, a section of skin 40 includes hairs 41 growing in hair ducts 42. The method first includes the step of removing hairs 41 from respective hair ducts 42 in section of skin 40, for example, by waxing. FIG. 8 shows section of skin 40 with hairs 41 substantially removed. At this stage, a contaminant 49 is applied to skin section 40.

Figure 9:
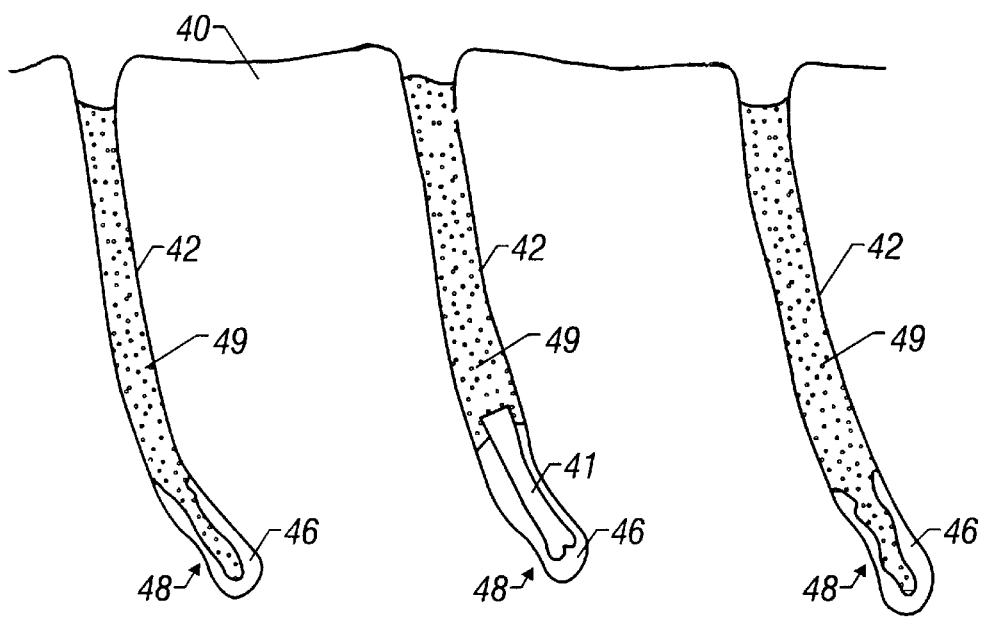
FIG. 9. is a diagram of the section of skin of FIG. 8 after the contaminant has been caused to move to the bottoms of the hair ducts.

Contaminant 49 has a high absorption at or near at least one frequency band, or wavelength, of light. Contaminant 49 can include carbon particles mixed with a liquid, such as mineral oil, peach oil or the like. As shown in FIG. 8, contaminant 49 is initially confined to the upper reaches of ducts 42. At least a portion of contaminant 49 is then caused to move to the bottoms of ducts 42, as shown in FIG. 9. Contaminant 49 can be moved downwards with a variety of methods, which can include gentle massaging and applying ultrasound to the skin. Contaminant 49 can also be caused to move toward the bottoms of ducts 42 by applying a few pulses of laser light to skin section 40, wherein the laser pulses are of a duration, frequency and fluence to drive contaminant 49 farther into ducts 42. If contaminant 49 is carbon particles mixed with oil, forcing pulses 55 of light at 1064 nm wavelength produced by a ND:YAG laser, having a pulse duration of about 10 ns and a fluence of about 3 J/cm$^2$, will be absorbed by the carbon particles. The light energy absorbed from forcing pulses 55 causes the carbon particles to fracture into smaller fragments with a force sufficient to drive some of the fragments deeper into ducts 42. Only a few forcing pulses 55 are typically needed to drive the carbon particles farther into the bottoms of ducts 42, as shown in FIG. 9.

An arrangement for applying a pulsed beam of laser light to skin section 40 is illustrated in FIG. 3 and described in Sections 1 and 2. In this method, however, hairs 41 are first removed from skin section 40.

Figure 10:
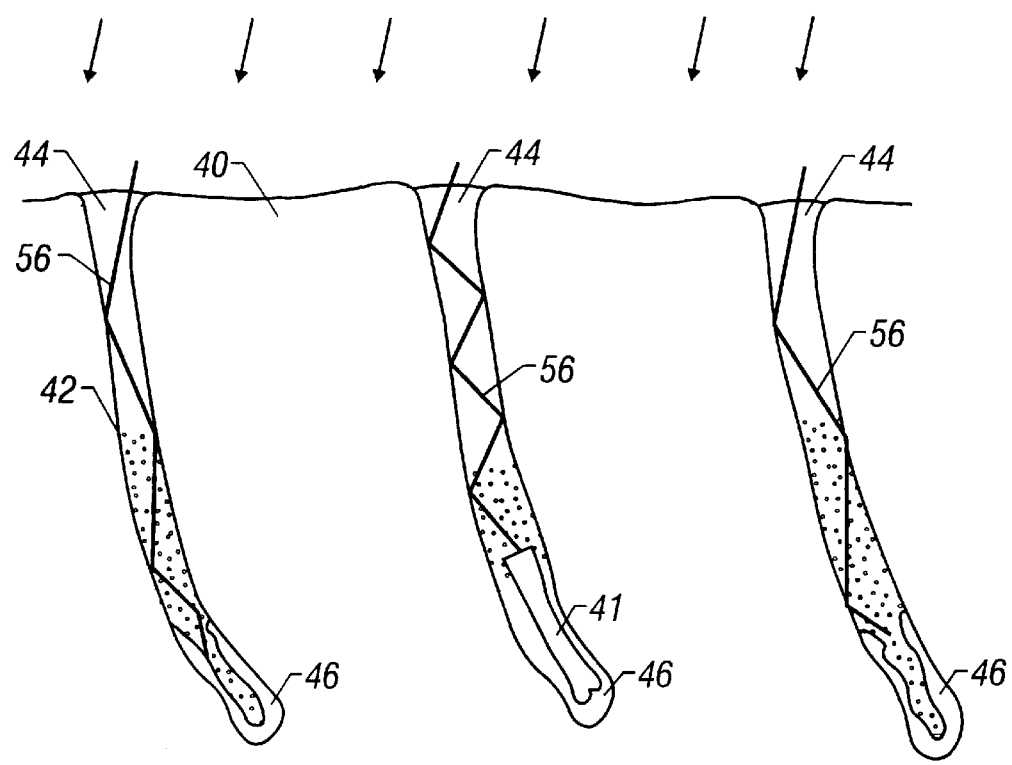
FIG. 10 is a diagram of the section of skin of FIG. 9 during illumination with laser light according to the hair removal process.

Now referring to FIG. 10, hair ducts 42 are then filled with a light guiding fluid 44 having an index of refraction that is greater than that of skin tissue. A region of skin section 40 is then illuminated with a light beam 52 at the wavelength which is absorbed by contaminant 49. In the case where contaminant 49 includes carbon particles, the Nd:YAG laser can be used again. Fluid 44 conducts light down hair ducts 42 to contaminant 49. The paths of photons in ducts 42 are indicated with lines 56. Contaminant 49 absorbs energy from the illuminating light and transmits at least a portion of the absorbed energy to papillae 46 at the bottoms of respective hair ducts 42, thereby damaging or destroying papillae 46 with the transmitted energy. Where carbon particles are the contaminant, several more short light pulses similar to driving pulses 55 can be applied at the end of the process to further fragment any remaining particles into insignificant sizes.

The opening of a hair follicle has the shape of a convex lens. Therefore hair follicles 46 will focus light once they are filled with high refractive index fluid 44, such as mineral oil. By this means, a complete "fiber optic" light guiding system is formed naturally. Hair-removal can be achieved employing both long pulse duration light and short pulse duration light, as will be described in the examples below. Since the light from beam 52 is guided to papillae 46 through hair ducts 42, rather than propagated through tissue, the light source can be of any wavelength that is highly absorbed by contaminant 49.

In the case in which contaminant 49 is carbon particles, the following illumination parameters have been found to be useful in destroying papillae 46 after the carbon particles are driven to the bottoms of ducts 42. The illuminating wavelength should be in a range of about 400 nm to about 1500 nm, however, wavelengths in a range between about 600 nm and about 1300 nm are more effective. The diameter of beam 52 should be large enough to obtain deep penetration of the skin, for example, in a range of about 8–12 mm diameter. Although contaminant 49 does not need to absorb photons scattered through the skin for this method to be effective, using an illuminating wavelength having good penetration through skin will help avoid excessively heating near the surface of skin section 40. Damage can be caused to papillae 46 by either heating the carbon particles with long pulse illumination or by fragmenting the carbon particles by exploding them with short duration pulses, as described in the examples below.

EXAMPLE 10

Short Pulse

The pulse duration should be shorter than the thermal relaxation time of the contaminant. The contaminant in this embodiment includes carbon particles that have a thermal relaxation time on the order of a microsecond. Therefore, a pulse duration of about 5 ns to about 50 ns can be used, and a duration of about 10 ns is very effective. We use a Nd:YAG laser that produces pulsed light at a wavelength of 1064 nm. The beam fluence for each pulse should be enough to explode or fragment the carbon particles. A fluence in a range between about 0.1 J/cm$^2$ and about 10 J/cm$^2$ will work, and a fluence of about 3 J/cm$^2$ works well. Using these pulse parameters and a beam diameter of about 10 mm, about 5–10 such pulses are enough to damage or destroy the papillae so as to inhibit the regrowth of the hair.

EXAMPLE 11

Long Pulse

This embodiment employs illumination pulses with a duration that is longer than the thermal relaxation time of the contaminant so that the contaminant heats up sufficiently to denature papillar tissue. In this example, where the contaminant includes carbon particles and the light source is a Nd:YAG laser producing pulsed light at a wavelength of 1064 nm, the pulse duration is in a range of about 100 $\mu$s to about 100 ms, and the beam fluence can be in a range of about 3 J/cm$^2$ to about 60 J/cm$^2$. In a specific embodiment, the beam diameter is about 10 mm, the fluence is about 40 J/cm$^2$, and the pulse duration is about 100 ms. With these parameters, about one to five pulses are sufficient to effect hair removal.

No. 4: REMOVAL OF THE STRATUM CORNEUM TO CREATE A BIOLOGIC WINDOW FOR TRANSDERMAL DRUG DELIVERY AND MEASUREMENT OF BODY FUNCTIONS

A method is described for selectively removing the stratum corneum of the skin to create a portal for transdermal drug delivery and for measurement of body functions. The stratum corneum is widely recognized as the key barrier against effective drug delivery across the intact skin. Removing the cellular layers of the stratum corneum before applying a transdermal drug delivery system would enhance the ability of a drug to diffuse across the remaining layers of the skin. The stratum corneum also acts as a resistive barrier to electronic sensors that are placed on the skin for measuring body functions, such as sensors used for taking electrocardiograms. Removing the stratum corneum would enable more sensitive and accurate electronic sensing of a medical patient's body functions.

Figure 11:
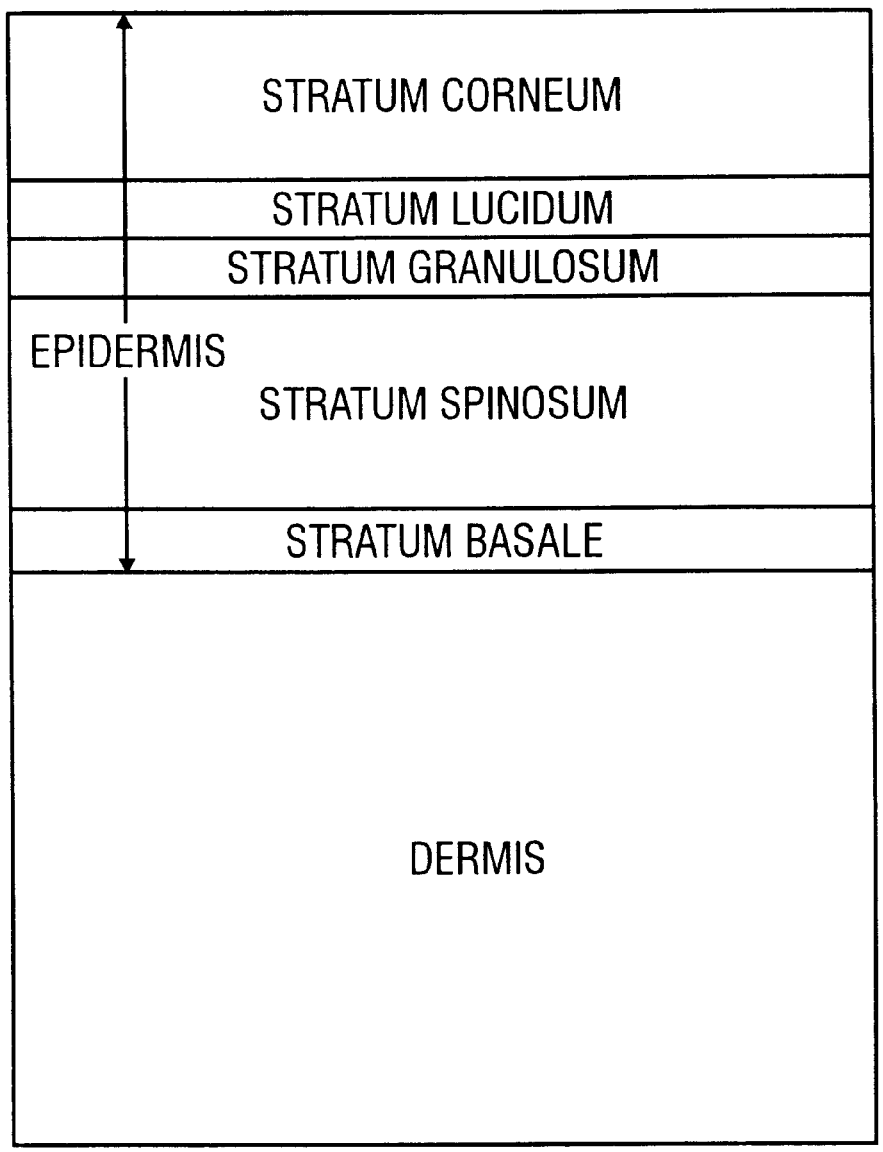
FIG. 11 is a block diagram illustrating the arrangement of different layers of skin.

The epidermis of the human skin includes several distinct layers of skin tissue. These layers are shown in block diagram form in FIG. 11. The deepest layer is the stratum basale, which consists of columnar cells. The next layer up is the stratum spinosum, which is composed of polyhedral cells. Cells that are pushed lip from the stratum spinosum are flattened and synthesize keratohyalin granules to form the stratum granulosum layer. As these cells move upward they loose their nuclei and the keratohyalin granules fuse and mingle with tonofibrils. This forms a clear layer called the stratum lucidum, which is composed of closely packed cells. These cells are further compressed as they move up, forming opaque squama. Squama are all flattened remnants of cells that have become completely filled with keratin and have lost all other internal structure, including nuclei. These squama constitute the outer layer of the epidermis, the stratum corneum.

At the bottom of the stratum corneum the cells are closely compacted and adhere to one another strongly, but closer to the surface they become loosely packed and eventually flake away at the surface. In the cheek skin of a 50 year old person, the outer portion of the stratum corneum typically consists of about 15 layers, which flake away at a rate of about one or two layers per month.

The stratum corneum cells are lifeless. Nerve endings and blood vessels do not extend into the stratum corneum. The purpose of the stratum corneum is to provide the skin an outer barrier to environmental hazards. The stratum corneum also serves as a barrier to transdermal drug delivery systems, such as, for example, nicotine patches.

This aspect of the invention uses laser light to remove some or all of the stratum corneum. Stripping the external 10–20 layers of the stratum corneum off the skin can expose the underlying basal surface of the epithelium. Application of a transdermal drug delivery system directly to the denuded skin decreases the distance across the epithelium and bypasses the key barrier to passive diffusion.

The procedure for removing the stratum corneum includes treating the skin with carbon particles such that the particles infiltrate into spaced between the cells in the upper few exposed layers of the stratum corneum, and irradiating with laser light at a wavelength that is readily absorbed by the carbon particles. When short duration pulses of light are used, the particles quickly absorb sufficient energy to cause them make tiny explosions that exfoliate about 1–6 surface layers stratum corneum cells. This process of exfoliating the outer layers of the stratum corneum is described in U.S. Pat. No. 5,423,802. The process can be repeated to remove additional layers of the stratum corneum. This creates a "denuded window" in the treated section of skin through which a drug or other active agent can be transdermally delivered. The size of the denuded window may be tailored to the dimensions of a transdermal dressing or patch.

Figure 12:
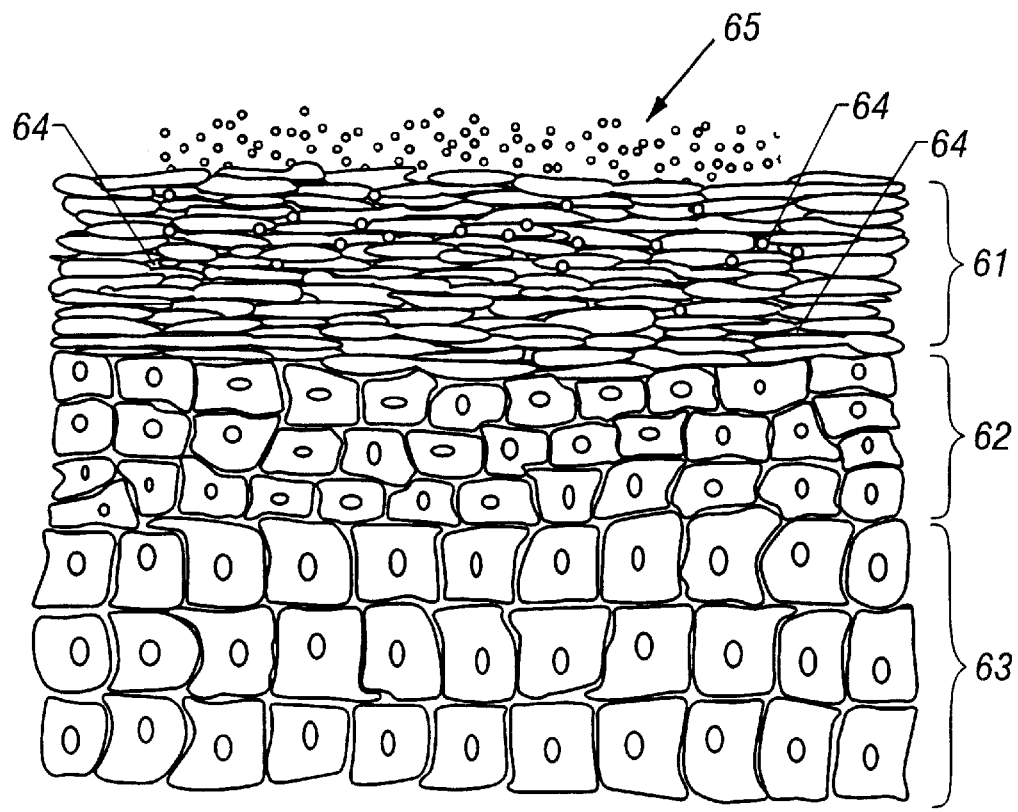
FIG. 12 is a diagram of the upper three layers of the epidermis of a section of skin during an initial step of a process to remove the stratum corneum.
Figure 13:
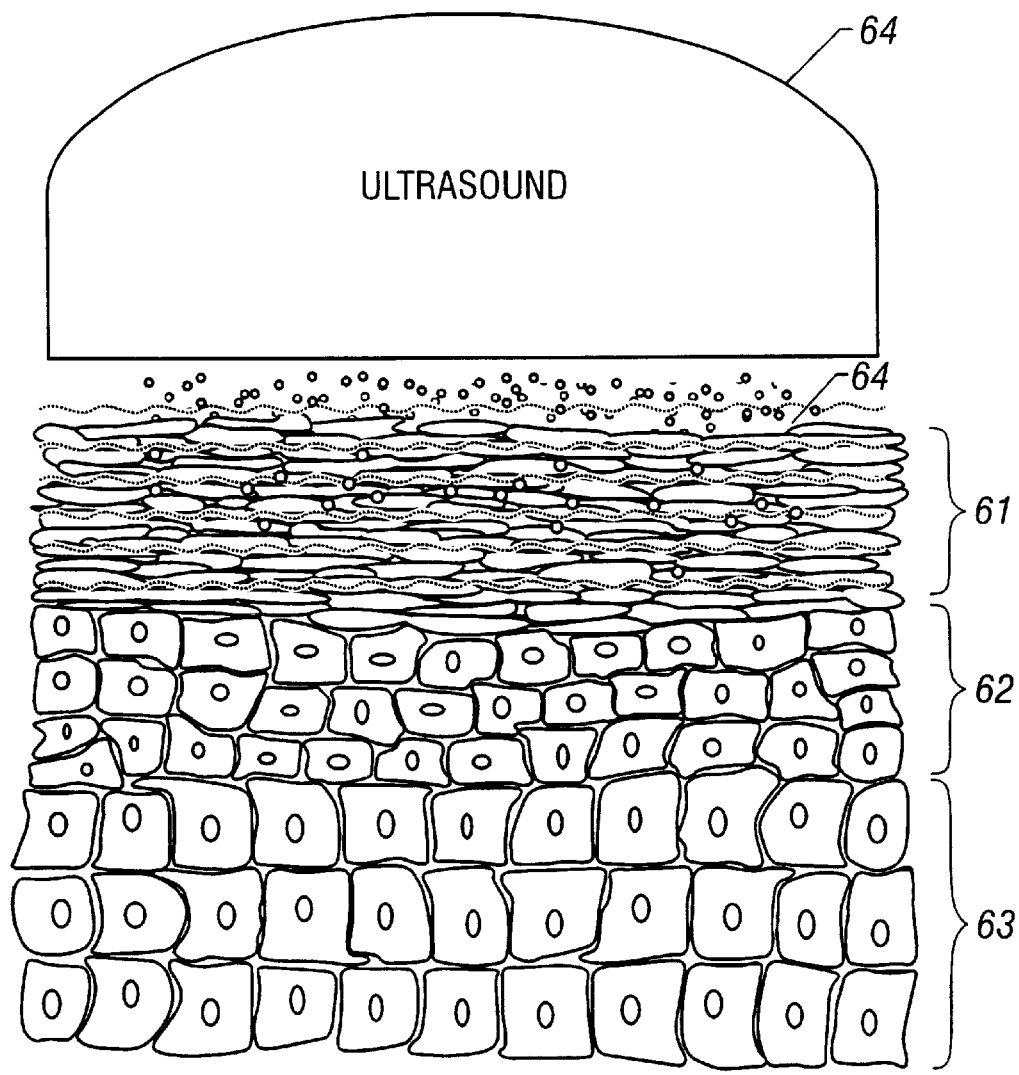
FIG. 13 is a diagram of the section of skin of FIG. 12 during a process step in which ultrasound is applied to the section of skin to work a chromophore into spaces in the stratum corneum.

Referring now to FIG. 12, a section of the outer three layers of the epidermis, the stratum corneum 61, the stratum lucidum 62 and the stratum granulosum 63, is diagramed in sectional view. There are spaces between some of the cells in the stratum corneum. A mixture of carbon particles 65 and an oil or lotion is applied to the surface of the stratum corneum. Carbon particles 65 can be approximately 1 micron graphite particles suspended in baby oil in a 20–50% carbon to oil weight ratio The next step is to force carbon particles 65 into spaces 64 located between stratum corneum cells. This step is shown in FIG. 13, in which an ultrasound unit 66 operating at about 0.2 W/cm$^2$ and about 10 MHz is employed to infiltrate carbon particles 65 into spaces 64. Approximately five minutes of ultrasound treatment at this frequency and power level will force a significant number of carbon particles 65 down through several layers of the stratum corneum 61.

The next step is to provide pulses of laser light to the treated section of skin. An arrangement for scanning pulsed laser light to a section of skin is illustrated in FIG. 3. In that system, laser 50 provides pulses of light through movable optical cable 51. A pulsed beam 52 is emitted through end piece 53, which can be held by an operator. The operator moves endpiece 53 while aiming beam 50 at a subject's skin 40 to scan beam 53 over a selected area.

In the described embodiment, the laser system can be a SOFTLIGHT® system, supplied by ThermoLase Corporation of San Diego, Calif. Laser 50 in this system is a Q-switched Nd:YAG laser providing pulsed light at a wavelength of 1064 nm. Beam 50 should be large enough to provide good penetration of skin, with a diameter of between about 8–12 mm. In the described embodiment, a beam diameter of about 8 mm is employed. The fluence of beam 50 should be in a range of about 0.1 J/cm$^2$ to about 10 J/cm$^2$. A fluence of about 3 J/cm$^2$ works very well. The pulse duration is in a range of about 5 ns to about 50 ns, with a duration of about 10 ns providing good results.

Figure 14:
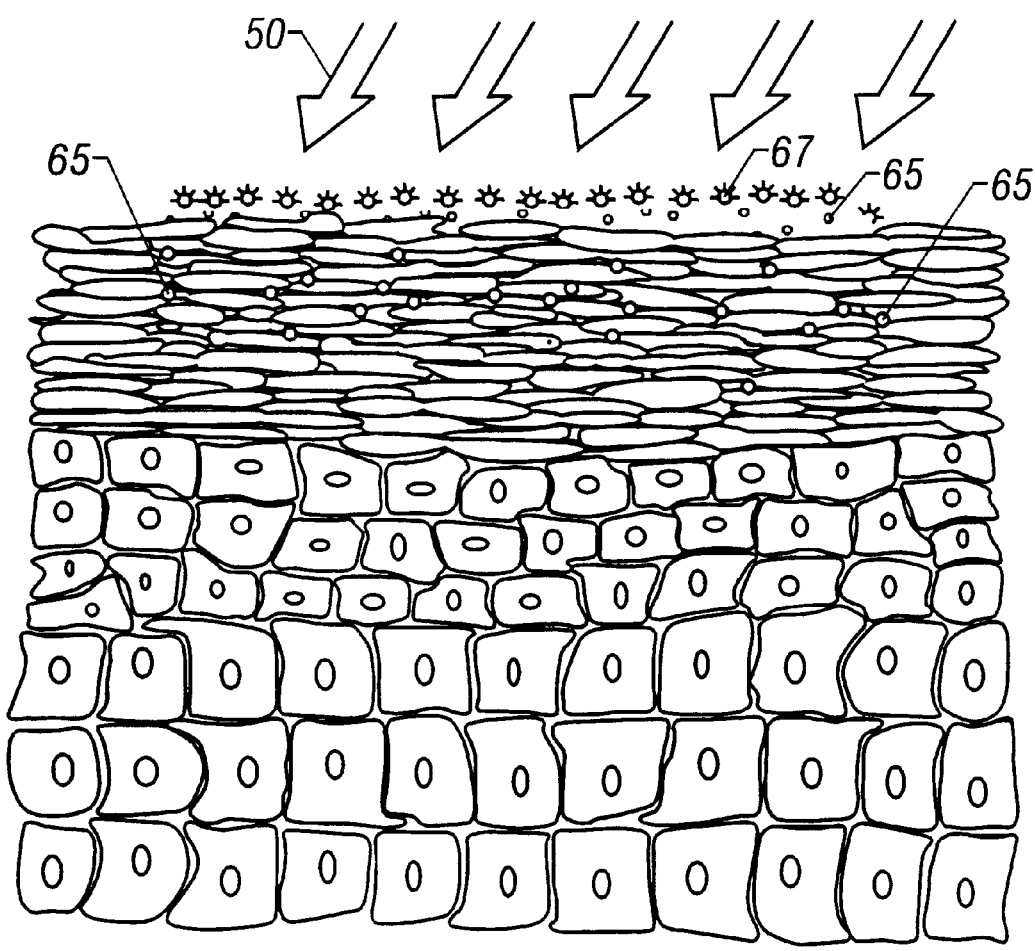
FIG. 14 is a diagram of the section of skin of FIG. 13 being illuminated.

Referring now to FIG. 14, laser beam 52 is scanned over the section of skin treated with carbon particles 65 such that each location of a selected area is subjected to pulses at a frequency of about 1 Hz. A first pulse of beam 50 is primarily absorbed by a surface layer 67 of carbon particles 65. The light energy is deposited more quickly than heat can be dissipated from particles 61. Enough energy can be absorbed by particles 65 to cause them to vaporize the smaller ones of particles 65 and/or explode the larger ones of particles 65 into smaller fragments that fly off with high energy. Lower layers of carbon particles under surface layer 67 are effectively shielded from the first pulse by surface layer 67. However, the destruction of surface layer 67 helps to force more carbon particles 65 deeper into the stratum corneum 61.

Figure 15:
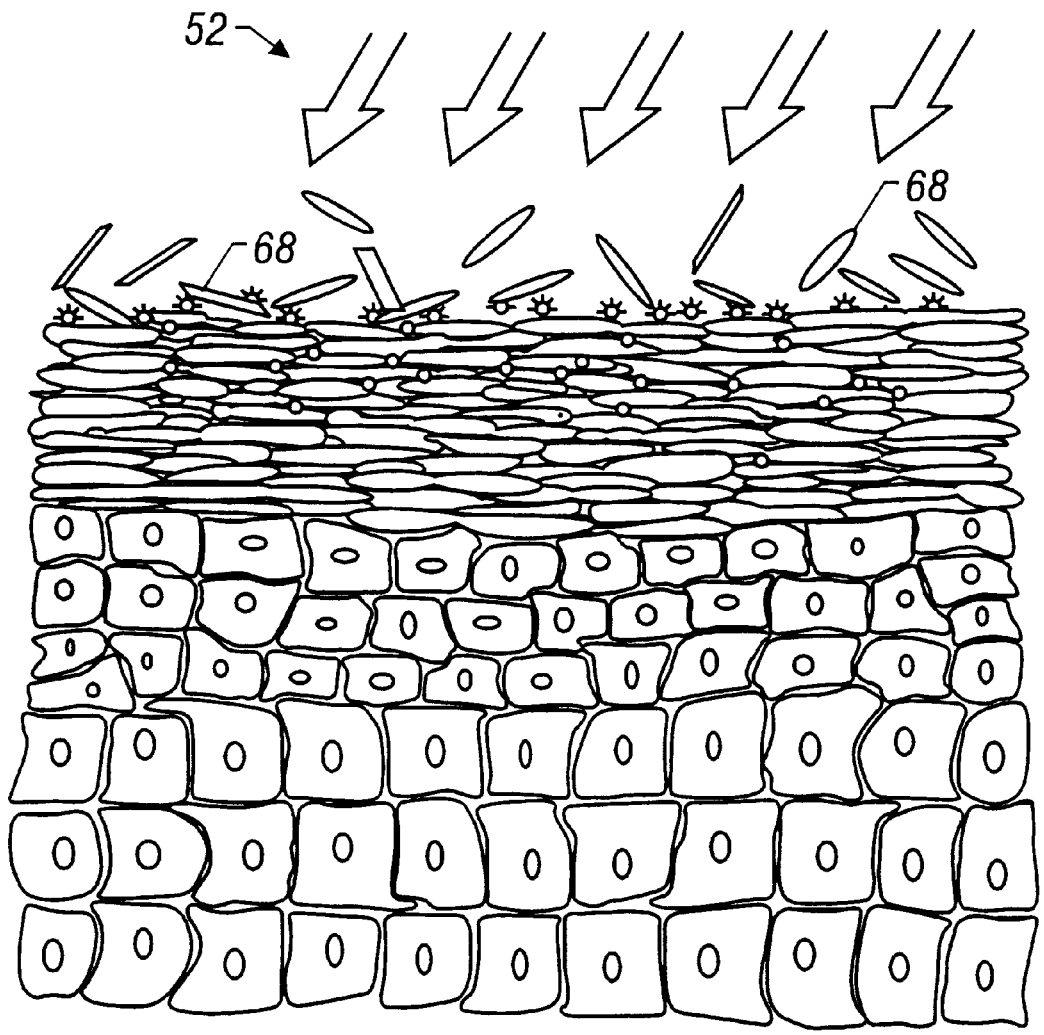
FIG. 15 is a diagram of the section of skin of FIG. 14 during further illumination.

Scanning beam 52 over the section of skin is repeated until all carbon particles 65 on the skin surface are vaporized or otherwise blown away. Eventually, beam 52 penetrates to carbon particles 65 located in spaces 64, causing these particles 65 to vaporize or explode as shown in FIG. 15. This process loosens and breaks off cells 68 from the stratum corneum 61. Scanning continues until almost all remaining carbon particles 65 are destroyed.

Figure 16:
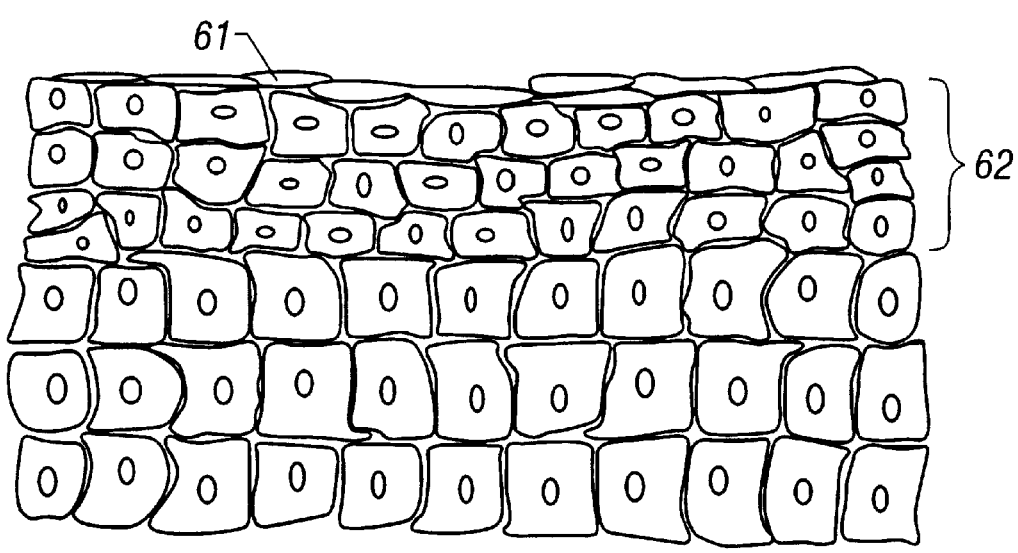
FIG. 16 is a diagram of the section of skin of FIG. 15 after most of the layers of cells of the stratum corneum have been exfoliated.

Typically, the entire process will exfoliate about I to about 6 layers of the stratum corneum. More carbon particles 65 can be applied to the same section of skin and all the steps repeated to exfoliate additional layers of cells from the stratum corneum 61. FIG. 16 illustrates a section of skin in which almost all layers of the stratum corneum 61 have been removed by the described process. The stratum lucidum 62 remains essentially intact.

Figure 17:
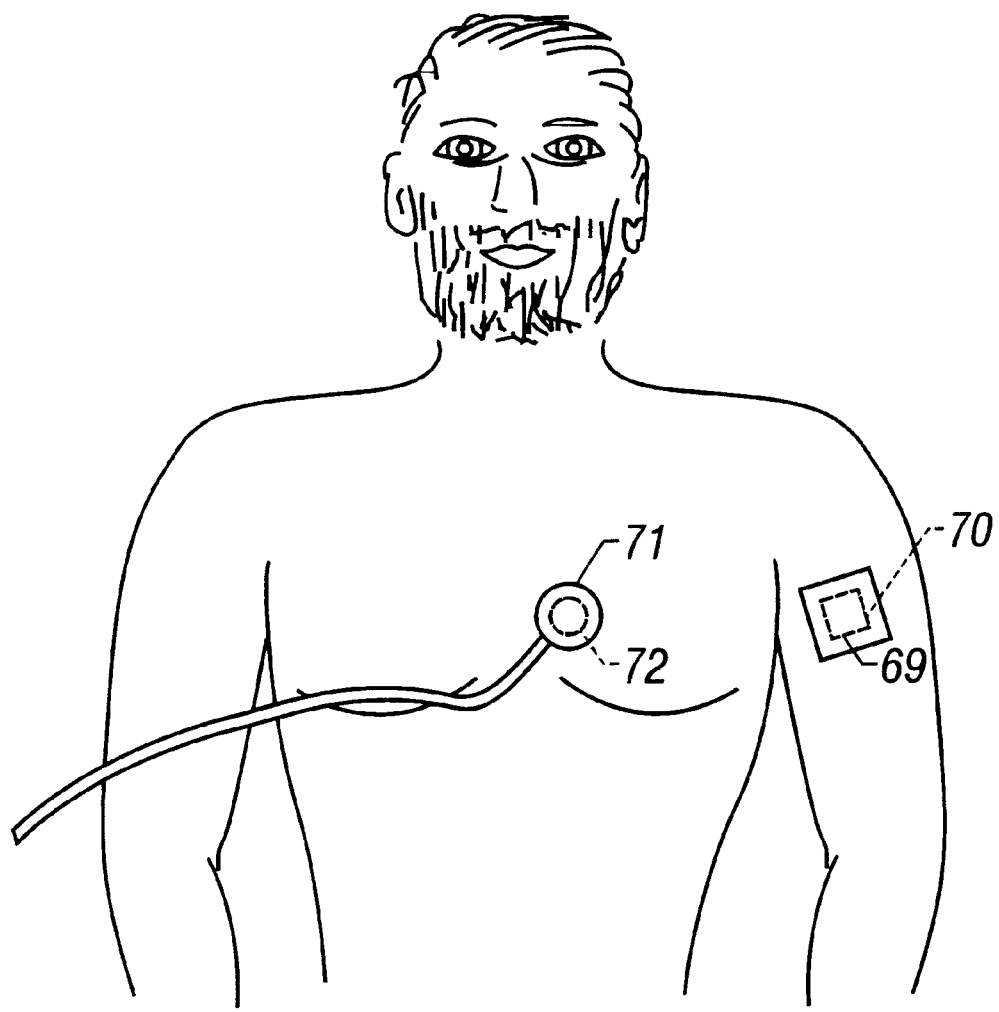
FIG. 17 is a diagram of the upper body of a person illustrating placement of a transdermal drug delivery patch and an electronic sensor over two skin areas from which the stratum corneum has been removed.

Once several layers of the stratum corneum 61 are removed from a section of skin, a drug or other agent, or an electronic sensor can be applied to that section in a well-known manner. Referring now to FIG. 17, the upper body of a male subject is illustrated. A transdermal delivery skin patch 69 is placed on the subject's upper arm over an area of skin 70 that been treated as described above to remove essentially all of the stratum corneum 61. FIG. 17 also illustrates the placement of an electronic sensor 71 in the subject's chest for sensing electric signals from the heart. Sensor 71 is positioned over a second area of skin 72 from which the stratum corneum 61 has been substantially removed. Each of patch 69 and sensor 71 can be attached to the subject's skin in any manner that is usually used in the art. In the case of patch 69, the drug or active agent that patch 69 carries is delivered through skin area 70 more effectively than it would through an untreated nearby area of the skin. In the case of sensor 71, sensor 71 is able to receive a stronger electronic signal through skin area 72 than would be possible in untreated areas of the subject's skin.

Removing some or all of the layers of the stratum corneum 61 is not painful. The described process removes only dead cells and is substantially harmless to layers of living cells in the skin located below the stratum corneum.

This aspect of the invention includes all methods of laser removal of the stratum corneum, including as well the use of chromophores other than carbon particles 65, as well as any laser based approach, without restriction, that can be used to safely remove the outer 10–20 layers of the stratum corneum. Instead of a patch, a lotion or cream can be used containing the active agent, for instance encapsulated for slow release in a slow release drug delivery formulation, such as liposome, microcapsule or other lipid-based systems.

No. 5: TIME RESOLVED CONFOCAL MICROSCOPE FOR IMAGING OBJECTS THROUGH HIGHLY LIGHT SCATTERING MEDIA

This aspect of the invention provides an instrument for noninvasive microscopic observation of objects embedded deep in a highly light scattering media, for example biologic tissues, with spatial resolution of the order of less than one micron in both axial and radial directions. The instrument combines a confocal microscope with optical ultrafast time resolution techniques. The combination of these techniques in a single system can provide a significant improvement in the signal to noise ratio of a confocal microscope.

A confocal laser scanning microscope (CLSM) is an instrument designed to construct three-dimensional images of microscopic objects in weakly scattering media. The principles of operation for confocal microscopes are known, and will not be discussed in detail. It suffices to mention that confocal microscopes scan an illumination beam from a point source over an area of a sample while an objective lens focuses the illumination beam at a fixed depth in the sample. The reflected signal is received by an optical signal detector, such as a photomultiplier tube (PMT), that has a small aperture placed in front of its receiving surface. The aperture in front of the detector cuts off out of focus light scattered from areas of the sample other than the location being scanned. If a collimated light source is used instead of a point source, a second focusing lens positioned in front of the detector aperture lens focuses the signal from the sample onto the detector receiving surface through the aperture. By recording the signal from the PMT as the illumination beam is scanned over a plane of the sample, an image of features of that plane can be constructed. By moving the focal depth with the objective lens, images of slices of the sample at different depths can be obtained.

The CLSM offers high spatial resolution and fine sectioning capabilities. Image sections can be obtained by confocal microscopy that are separated by less than one micron. Conventional confocal microscopes also provide a high image signal to background noise ratio (SNR). This results from the excellent spatial resolution that can be obtained with a confocal microscope and from the predominance of single light scattering over multiple scattering in a specimen object. The high resolution is a combined effect of sharp focusing of a probe beam into the object and high spatial resolution of an optical sensing system.

When an object is viewed through a layer of turbid media, the quality of the images is determined by the capability of an optical system to do two things. The first factor is the optical system's ability to collect a sufficient amount of signal light scattered by the object directly into the system without any further scattering in the surrounding turbid medium. The second factor is the optical system's ability to reduce the effect of light responsible for the noisy background detected by the system from the scatterers dispersed in the out of focus volume. As multiple scattering becomes more and more significant, the signal to noise characteristics of the conventional confocal microscope imaging system deteriorate because scattering snatches photons from the main stream of the focused laser beam and the signal level decreases. Simultaneously, the background of diffusely scattered light increases. The image signal becomes indistinguishable for a reasonable signal accumulation time when optical inhomogeneity of the medium is significant enough for a few scattering events to occur, on average, during light travel through the layer.

A conventional confocal microscope, though having high spatial resolution in the axial direction (depth), is ineffective for providing reasonable images below 200–300 micron deep into human tissues, e.g., skin. Photons emerge from the tissue after reflection deep in the tissue. A photon that penetrates deeply into tissue before scattering is more likely to be absorbed before it has a chance to emerge from the tissue than a photon that scatters near the surface. Thus, the expected signal from deeper depths within the tissue is much lower than that from structures closer to the surface. Up to 50% of light incident on human skin is diffusely scattered back and much of this light is due to the photons that leave the tissue after a few scattering events. In CW illumination mode, these short-travel-time-in-tissue photons are responsible for superficial glare that dominates the weak image signal coming from deeper within the tissue. In addition, the reflected signal is spread out over time. Promptly reflected photons that travel a short path length in the tissue arc reflected first and more deeply penetrating photons that travel a longer path length emerge later.

The invention significantly improves the ratio of an image signal to a background noise signal when objects hidden in highly light scattering media, such as skin tissue, are observed with a confocal microscope. As mentioned above, the invention incorporates optical ultrafast time resolution techniques with a confocal microscope. This improves signal-to-noise characteristics of the confocal microscope, and enables visualizing deeper structures in the scattering media than would be possible using only a confocal microscope. The principle concept of time resolved confocal microscopy is to employ a time gating method to prevent the photons that are promptly reflected from near the surface of a sample, which constitute the bulk of a signal reflected from tissue, from affecting formation of the image being obtained from deeper in the sample in the confocal microscope.

To image deeply embedded structures in human skin the following factors are combined:

1. Making use of the sharp focus response and low out-of-focus wings of resolution characteristic of the confocal microscope;
2. Employing light having good penetration in skin tissue for imaging, such as light in the 700–1200 nm range of wavelengths, and particularly IR light in a range of approximately 750 nm–1000 nm; and
3. Increasing the effective penetration depth of probing radiation by selecting for imaging only multiply scattered light with long transient time within the tissue by employing a time-resolving technique.

Time resolved optical imaging is a technique that includes illuminating an object with a short laser pulse and time gating the scattered light received back from the object. The range to a light scattering object is determined by the delay between the gate position in time with respect to the moment of the pulse emission. The range is one half of the round trip distance of light within the delay time. In general terms, spatial resolution of the time ranging system becomes better as the probing pulse becomes shorter and as the time gate used for detecting the reflected light from the object becomes narrower. For ultrafast pulses, for example, 100 fs pulses, the potential range resolution is of the order of 20 microns in skin tissue, which has an index of refraction of about 1.4. A delay line is employed to adjust the gate position with an accuracy of a few femtoseconds using off-the-shelf optical components and translation stages.

The signal-to-noise characteristics of the ranging system depends on how much light is reflected by the object and how much background light fits within the same time gate. As short light pulses propagate through a turbid medium their intensities are reduced by light scattering. The propagating laser beam also generates a diffuse glare in the medium, much of which contributes to the background noise signal. Without time gating, one would detect a short signal pulse reflected by the object and a much longer pulse due to the multiple scattering of light by spatially distributed inhomogeneities in the background. In highly scattering media the intensity of the signal component is low and the integral intensity of the background is high. On the other hand, the noise component is by far more extended in time as a result of multiple scattering. With a narrow time gate the level of this noise component constitutes a fairly small fraction of its integral intensity.

Several methods are known for implementing optical time gated detection. Various techniques for time-resolved transillumination imaging are reviewed in "Time Resolved Transillumnination Imaging," by R. Berg, et al., in Medical Optical Tomography: Functional Imaging and Monitoring, SPIE Proc., vol IS11, pages 397–424 (1993), the entire disclosure of which is included herein by reference. Any of the devices and methods disclosed by Berg, et al. can be incorporated, with some modification within the skill of persons in the optical imaging arts, in the time gated confocal microscope of the invention. One group of incoherent time gating methods take advantage of nonlinear optical effects in materials, such as, for example, the Kerr effect, second harmonic generation, and the like. A powerful control pulse opens the gate within an ultra short time interval to let a much weaker signal of interest to pass through and be detected. Another group of incoherent methods incorporates electronic detection with a short reference pulse synchronizing a photon counting correlator or an ultrafast streak camera.

In coherent time gating methods, ultraslhort reference pulses are made to interfere with a certain portion of the signal, which has been broadened by multiple scattering. The interference produces a heterodyne signal at a photodetector proportional to the product of electric vectors in both pulses within the time of duration of the reference pulse. To facilitate detecting the heterodyne component of the signal and to improve its noise characteristics the reference wave is phase modulated, the AC signal of the photodetector is separated with an electronic filter and its amplitude is measured to retrieve information about the signal wave intensity.

Figure 18:
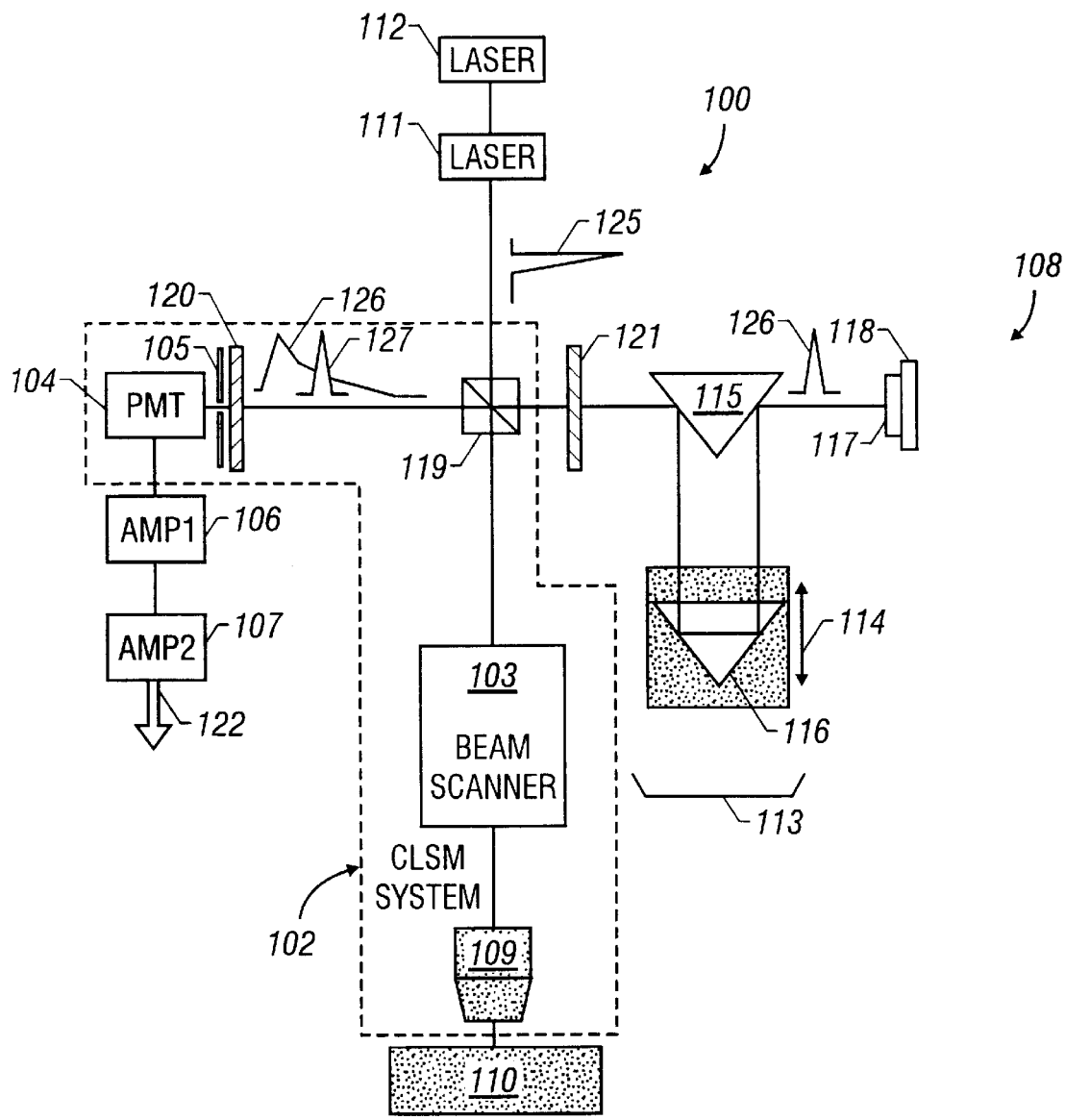
FIG. 18 is a block diagram of a time gated confocal microscope according to another aspect of the invention.

Referring now to FIG. 18, a time gated confocal microscope (TGCM) system 100 includes a modified confocal laser scanning microscope (CLSM) system 102. The essential components of a CLSM system that can be employed with the described TGCM system 100 can be a type OZ system, produced by NORAN Instruments Inc. of Middleton, Wis., and which is set to operate in the reflected light mode. CLSM system 102 includes a beam scanner 103, a photomultiplier tube (PMT) detector 104, a confocal aperture 105 positioned in front of PMT detector 104, a PMT signal preamplifier amplifier (AMP1) 106 and a second amplifier (AMP2) 107 that includes a band filter with the central frequency of the band corresponding to the oscillation frequency of a phase modulator 108, as will be described in greater detail below. An objective lens 109 focuses light from beam scanner 103 onto a specimen 110. An acousto-optic deflector in the Y direction in beam scanner 103 is replaced by a galvanometer scan mirror similar to that scanning in the X direction in the same device.

The light source for CLSM system 102 is a femtosecond laser 111. In the described embodiment, laser 111 is a Tsunami type laser that is pumped by an argon laser 112, both being the products of Spectra-Physics Lasers, Inc., of Mountain View, Calif. Laser 111 produces 80 fs pulses of light at a wavelength of 750 nm, an average power of about 500 mW, and a pulse frequency of 82 MHz.

TGCM system 100 also includes an optical delay line 113 and reference beam phase modulator 108. Delay line 113 includes a one direction manual translator 114 having a resolution of 1 $\mu$m or better, and two broadband cone reflectors 115, 116. Modulator 108 includes a broadband 100% reflecting mirror 117 attached to an oscillating piezoelectric actuator 118.

Femtosecond pulses 125 from laser 111 are fed into CSLM system 102 through one of its standard ports. A 50/50 beam splitter 119 replaces one of the standard corner reflectors between the port and the first scanning mirror (not shown). Light passing through beam splitter is scanned in X and Y directions in a plane perpendicular to the beam by beam scanner 103 and focused at a selected depth in specimen 110 by lens 109. Reflected light collected from specimen 110, which is broadened due to scattering in specimen 110, propagates through the modified optical system of the microscope, and is directed by beam splitter 119 as a signal pulse 126 onto the built-in PMT 104. A standard filter in front of the face of PMT 104 is replaced by a filter 120 adapted to pass through light of 750 nm wavelength and to reject other background wavelengths.

The other portion of light pulse 125 from laser 111 that is directed by splitter 119 to optical delay line 113 becomes a reference pulse 127. Delay line's 113 purpose is to compensate for the difference in the optical paths between the light propagating in the imaging portion of the device and the light propagating in the reference signal portion. Fine tuning with the help of translation stage 114 enables the short reference pulse 127 to interfere with a certain part of the broad signal pulse 126.

The relative timing of signal pulse 126 and reference pulse as they are directed towards PMT 104 is indicated by the diagram immediately to the right of filter 120 in FIG. 18. Reference pulse 127 strikes PMT 104 at the same angle as signal pulse 126. The two pulses 126, 127 interfere at the face of PMT 104 to give rise to a cross interference component in the PMT signal. Optical phase modulator 108 in the reference aim of TGCM system 100 introduces a periodic phase modulation into reference signal 127. This causes the PMT signal to be periodically amplitude modulated. The band filter in AMP2 107 separates out the amplitude modulated signal. The amplitude of this component is then measured and converted to a brightness signal 122 of the image pixel corresponding to a particular location of the microscope sampling volume. A reference beam attenuator 121 can be used to optimize the signal to noise ratio of the PMT signal.

It is important that the time gating of the imaging signal be synchronized with the spatial location of the microscope sampling volume. When reference pulse 127 opens the gate the reflected light must be coming exactly from the focus of the microscope to combine spatial and time gated discrimination of the images. As discussed above, when femtosecond laser pulse 125 is incident onto a highly scattering specimen 110, reflected light from specimen 110 is primarily due to photons traveling different paths in the tissue. In the case of multiple scattering in the tissue, the distribution of the travel times of the photons broadens the reflected pulse, which becomes signal pulse 126.

Figure 19:
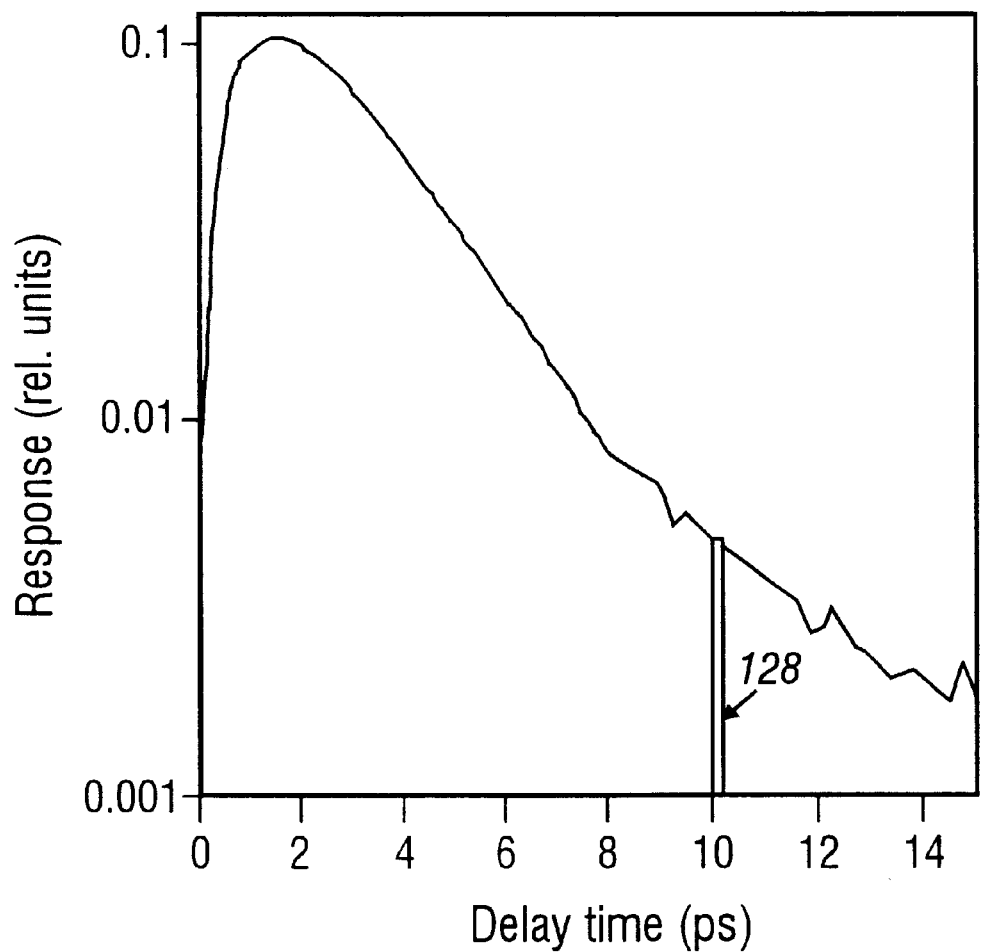
FIG. 19 is a graph that plots relative intensity of response to a signal reflected from a tissue specimen as a function of delay time.

FIG. 19 plots a calculated typical backscattered light time response of a semi-infinite light scattering phantom media having an index of refraction of about 1.4 to an ultrashort pulse illumination. Zero time is the moment of incidence of a 100 fs pulse on the phantom surface. The phantom has a scattering coefficient of 50 cm$^{-1}$, an absorption coefficient of 1 cm$^{-1}$, and an asymmetry factor (g) of 0.9. The narrow region at a delay time of about 10 ps indicated by reference number 128 represents the fraction of the backscattered light detected with a 100 fs incident pulse and a 10 ps delay of the gate.

Signal pulses 126 make a round trip to the focus of the microscope and back in a time $\tau=2*Z_f/V$, where $Z_f$ is the depth of focus from the surface of the media and V is the speed of light in the media. When the delay time is chosen to be equal to this round trip time both the confocal and the time gating system work synchronously, enabling the best spatial resolution and signal to noise performance of the system. For example, if the focus is located at a depth of 1 mm and the refraction index of the medium is 1.4, the time delay must be about 8.5 ps for the optimum performance of the microscope.

The principle benefit of the TGCM system is that it is able to image subsurface structures at depths several times deeper than previously attainable with convention confocal microscope systems, in addition, the TGCM system provides excellent resolution, even at tissue depths of about a millimeter or more.

A further advantage of the described imaging system is that it employs non-ionizing radiation, which can be harmful to the skin and underlying tissues.

Another advantage of the present system is that different types of subsurface structures can be imaged by employing different wavelengths of illuminating light.

No. 6: METHOD FOR DEPOSITING SUBSTANCES INTO THE HAIR SHAFT CANAL

This aspect of the invention provides a device and methods for depositing medications and other active substances into the hair shaft canal to create a local accumulation of the drug or active substance for slow release of a constant low dose. The invention can be employed, for example, to introduce a substance for regulating hair growth or for regulating the activity of sebaceous glands.

The principle methods presently used for hair growth regulation include hormone therapy, vasodilation with minoxidil, immunomodulation with cyclopropane, treatment with antibodies, or hair grafting. These techniques can involve a long term treatment regimen with drug administration or topical application more than once a day, or hair transplant operations.

Figure 20:
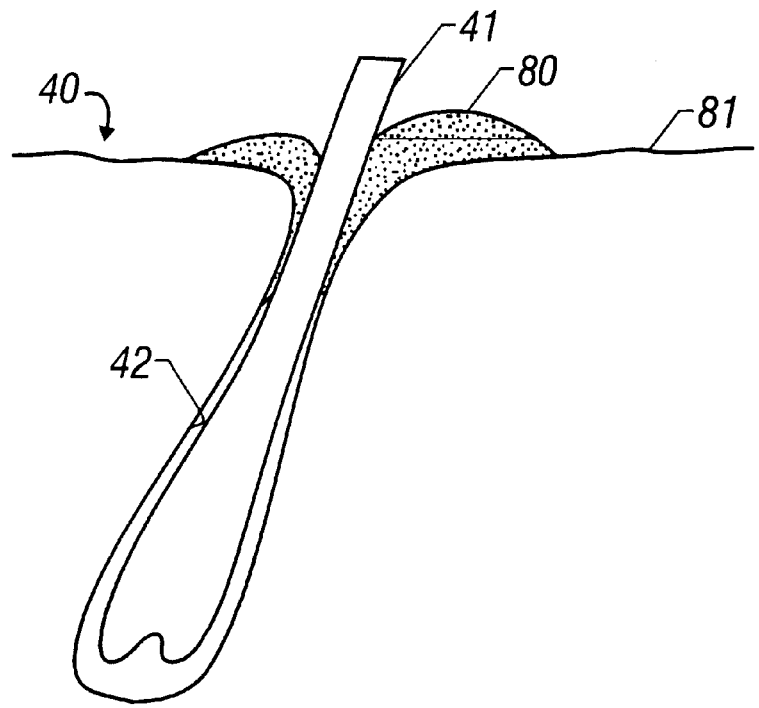
FIG. 20 is a diagram of a section of skin with one hair and illustrates a step in a process to deliver a composition containing a drug or active substance to the hair ducts according to another aspect of the invention.

Referring now to FIG. 20, a section of skin 40 includes a hair shaft 41 growing in and extending from a hair duct 42. It will be understood that other hair shafts 41 can be growing from hair ducts 42 in skin section 40. According to this aspect of the invention, substances that regulate hair growth or the activity of sebaceous glands are deposited in hair duct 42 encapsulated in microspheres formulated to have slow release properties. A substance, such as a drug, is encapsulated within or bound to the microspheres. Microspheres appropriate for use with the invention include liposomes, coacervate drops, erythrocyte shadow, latex or gelatin spheres, carbon microcrystals, and the like. A suspension 80 of the drug or substance, or a combination of drugs and/or substances, in the form of microspheres is topically applied to an area of skin to be treated, including skin section 40, the area of skin including one or more hair duct canals. Suspension 80 can be rubbed in and then the excess wiped off the skin surface 81 in order to create a concentration of the spheres around hair shafts 41 at the entrances to hair ducts 42.

Figure 21:
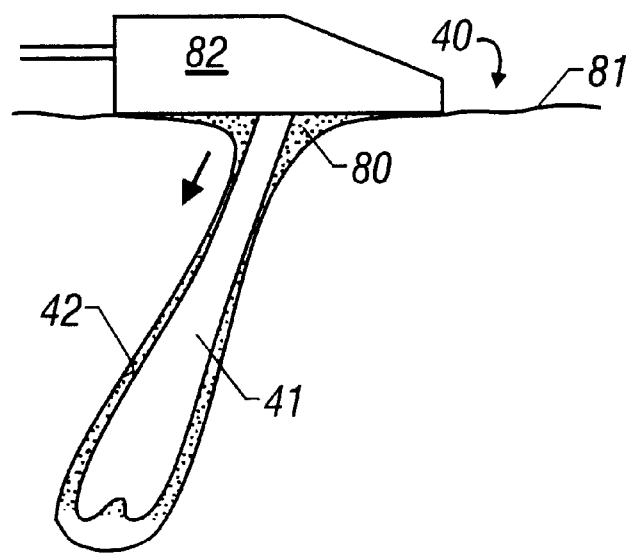
FIG. 21 is a diagram of the section of skin of FIG. 20 illustrating a step in which ultrasound is applied to urge the composition into the hair ducts.

Referring now also to FIG. 21, an ultrasonic device 82 or other mechanical oscillating device can also be applied to skin surface 81 to provide mechanical pulses that encourage the microspheres to enter into the hair canals.

The size of microspheres can be in a range of about 100 nm to about 2 $\mu$m. The stratum corneum serves as a barrier to intradermal penetration of these size microspheres through skin surface 81, and then to the hair shafts. The walls of hair shafts 42 are lined with cells that do not provide such a barrier. The drug delivery thus is very localized inside hair ducts 42. In addition, drug delivery is very effective within hair shafts 42 because of the lack of a transdermal barrier there.

The membrane of the microspheres is biodegradable, so that the encapsulated drug or active substance starts being delivered some time after suspension 80 is deposited. The drug or active substance in then released slowly as the microspheres degrade. If the size and/or type of the microspheres administered in a single application is varied, the microspheres will decay and begin to release the encapsulated or attached substance at different times. In addition the amount of drug or active substance released by different types or sizes of microspheres will also vary. As a result, the method of the invention can be tailored to bathe the papillae with the drug or active substance over an extended period of time.

Referring now to FIG. 22A, a multilayer liposome 83 has an active substance 84 encapsulated therein. FIG. 22B illustrates an erythrocyte shadow 85 with medication 86 inside. FIG. 22C shows a coacervate drop with a drug 88 inside. FIG. 22D illustrates a latex sphere with monoclonal antibodies 90. FIG. 22E depicts crystal particles 91 with drug molecules 92 bound to them.

No. 7: COOLING WINDOW FOR USE WITH LASER SKIN AND HAIR PROCESSES

Some of the processes described above apply pulses of laser light to the skin to bleach hair, to remove hair, to exfoliate layers of the stratum corneum and to image subsurface structures. It is important to keep the section of skin being illuminated with laser light cool enough so that the skin tissue is not denatured or otherwise damaged. Some locations may experience intense heating, such as the papillar regions in some hair removal processes, but the surrounding skin tissue should not be heated to a temperature over about 45° C. for any extended period of time.

Figure 23:
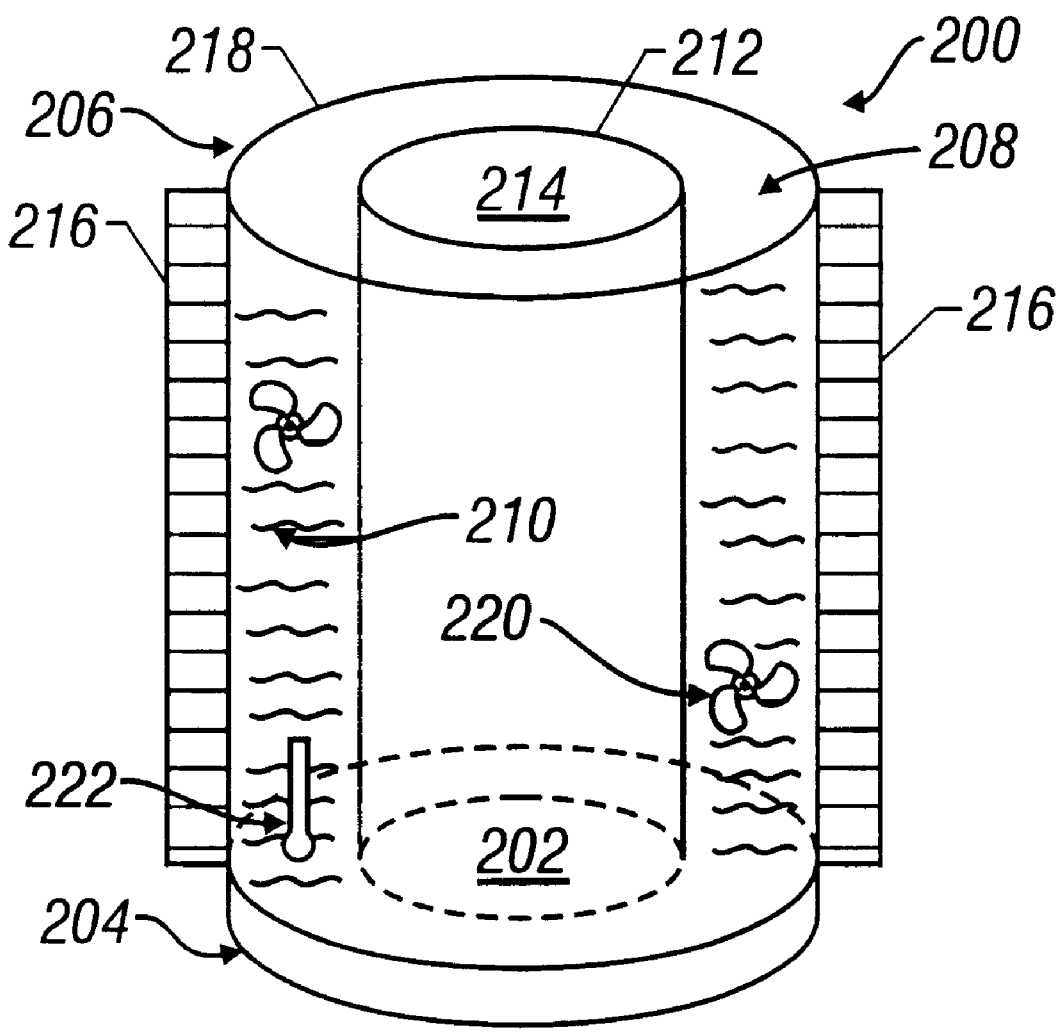
FIG. 23 is a perspective view of a cooling apparatus according to another aspect of the invention.

This aspect of the invention provides a cooling apparatus that can be used to help remove heat from the skin during illumination with laser light. Referring to FIG. 23, a cooling apparatus 200 includes a window 202 that is substantially transparent to light at the wavelength of the laser. In the described embodiment, window 202 is made of sapphire, which has good thermal properties. Window 202 is cooled by a support structure 204 that includes a heat exchanger 206. Support structure 204 preferably is made of a good thermal conductor, such as OFHC copper, and includes a hollow annular space 208 that is filled with a reservoir of cooling fluid 210, such as water. An inner wall 212 of annular space also forms an outer cylindrical wall of an open cylindrical space 214 through which laser light passes to window 202. One or more cooling elements 216 are attached to an outer wall 218 of annular space 208. Cooling elements 216 can be cooling fins, or, as in the embodiment illustrated in FIG. 23, they can be thermoelectric cooling elements. Cooling fluid 210 may circulate by convection. In the embodiment illustrated in FIG. 23, water is circulated by miniature fans 220 that are powered by a power supply (not shown). A temperature sensor 222 may be positioned in cooling fluid 210 or otherwise thermally coupled to support structure 204.

In use, cooling apparatus 200 is placed over the section of skin being illuminated such that only window 202 is in contact with the skin. A transparent thermally conductive gel (not shown) may be applied to the skin to facilitate thermal contact between the skin and window 202. Examples of thermally conductive gels include No. 5 Afterwax Skin Gel, produced by L'ELYSCE LABS, Aloe Vera with Lidocaine, available at Thrifty Payless stores, Corn Huskers lotion, produced by Warner-Lambert, and K-Y Jelly, produced by Johnson & Johnson. When laser light is directed through window 202, the section of skin in contact with window 202 is cooled by window 202.

Figure 24:
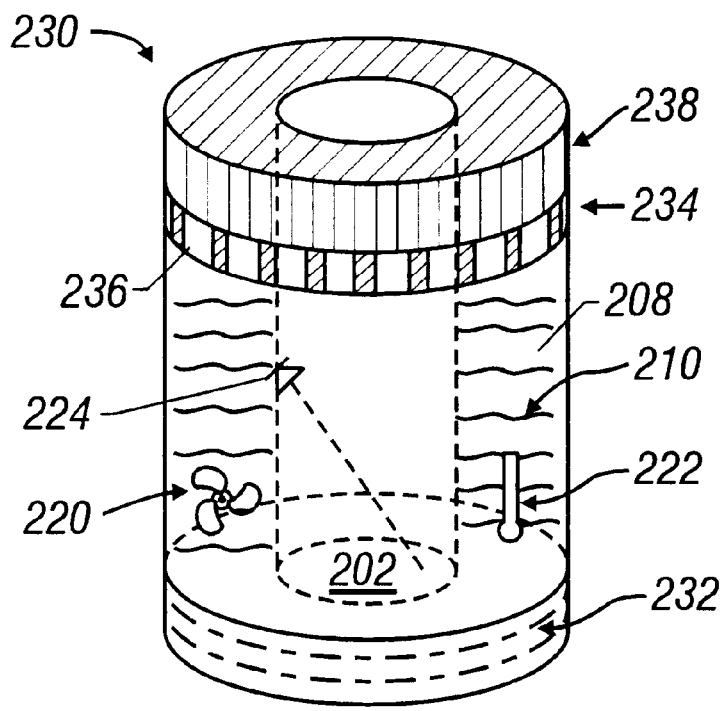
FIGS. 24–28 illustrate other embodiments of a cooling apparatus.

Another embodiment of a cooling device 230 is illustrated in FIG. 24. Cooling device 230, like cooling device 200, includes a sapphire window 202 in good thermal contact with a support structure 232, and an annular space 208 with a fluid reservoir 210. Fans 220 stir cooling fluid 210. A temperature sensor 222 senses the temperature of cooling fluid 210. A second sensor 224 senses the temperature of window 202. An end of support structure 232 opposite window 202 includes an array of circumferentially spaced thermoelectric cooling elements 234 attached thereto. Thermoelectric cooling elements 234 support and are thermally coupled to an annular ring-shaped radiator 236.

Figure 25:
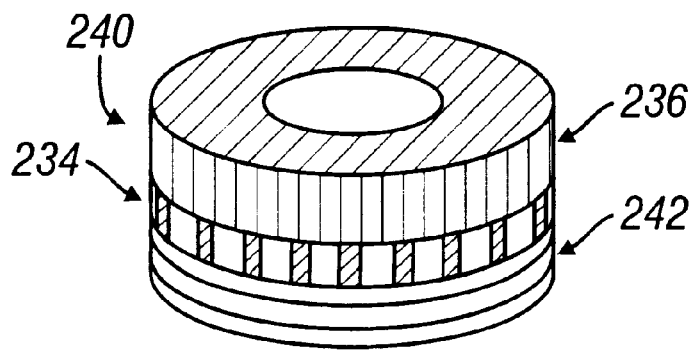

Yet another embodiment of a cooling device 240 is illustrated in FIG. 25. Cooling device 240 is substantially the same as cooling device 230, but does not include annular space 208 or a reservoir for cooling fluid 210, and therefore is much shorter than cooling devices 200 and 230. Cooling device 240 includes a support structure 242, thermoelectric cooling elements 234 and a radiator 236.

Figure 26:
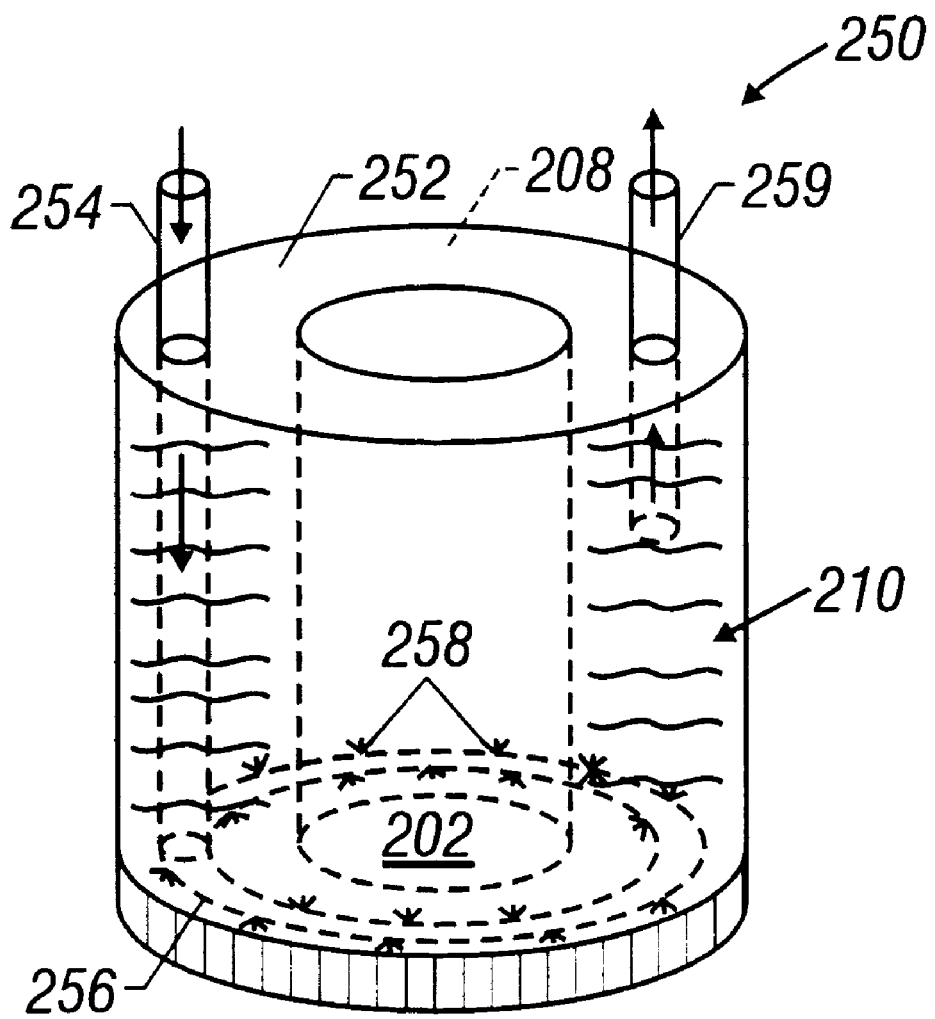

A fourth embodiment of a cooling device 250, shown in FIG. 26, includes a support structure forming an annular-shaped space 208 for chilled cooling fluid 210. Annular space 208 includes L cover 252. Chilled cooling fluid flows through an inlet tube 254 that passes through cover 252 and terminates in a ring-shaped portion 256 positioned close to window 202. Ring-shaped portion 256 of inlet tube 254 includes apertures 256 through which chilled cooling fluid 210 flows to fill annular space 208. Cooling fluid 210 flows out via an outlet tube 259 that passes through cover 252.

Figure 27:
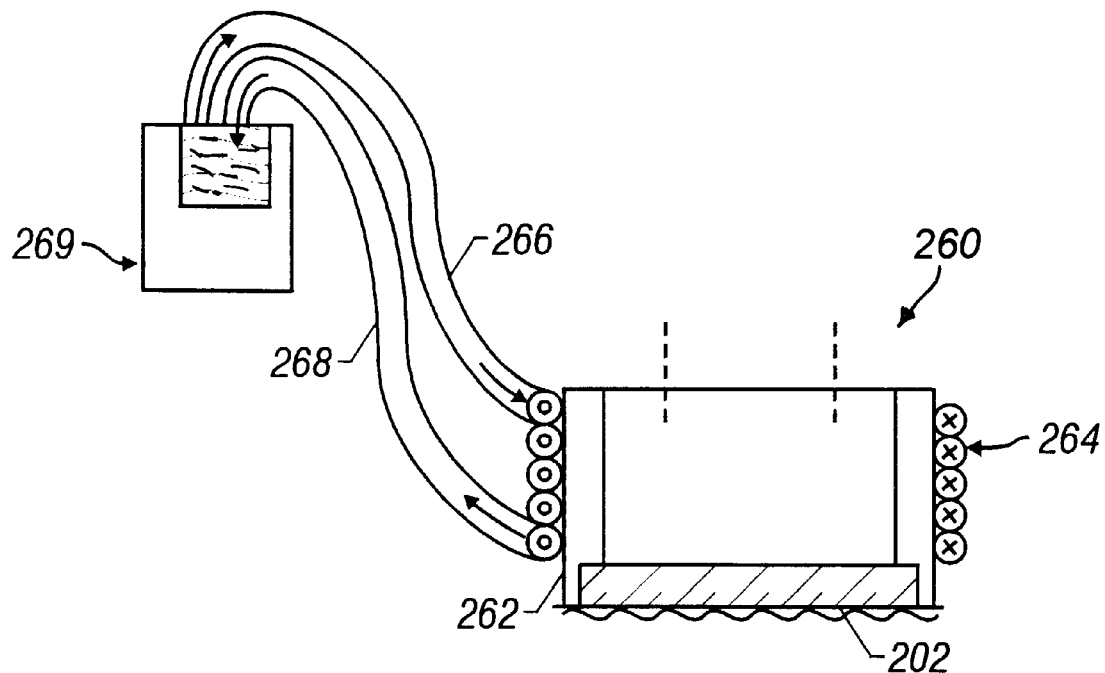

Referring now to FIG. 27, yet another embodiment of a cooling apparatus 260 includes a window 202, an annular-shaped support structure 262, but no fluid reservoir or thermoelectric cooling elements. Instead, support structure 262 is wrapped with coils of tubing 264 through which chilled water or another cooling fluid 210 circulates. Tubing 264 includes an inlet tube 266 and an outlet tube 268. Chilled cooling fluid 210 is pumped from a chilled reservoir 269.

Figure 28:
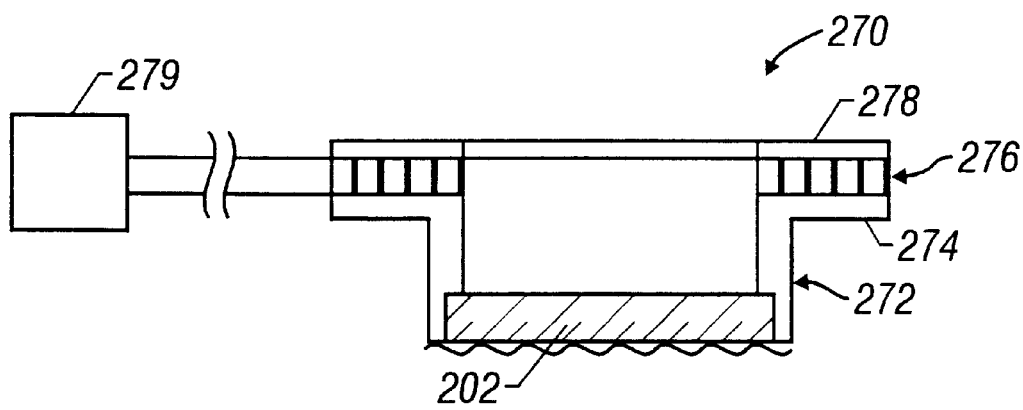

FIG. 28 shows still another embodiment of a cooling apparatus 270. Cooling apparatus 270 includes a sapphire window 202 held at the bottom end of a substantially annular-shaped support structure 272. An upper end of support structure 272 includes a first annular-shaped flange 274 that extends radially outward. Flange 274 is coupled to an array of solid state cooling devices 276, which are powered by a power supply 279. A second annular shaped flange 278 is coupled to the top ends of cooling devices 276. Support 272 and flanges 274, 278 are fabricated of a good thermal conductor, such as copper.

No. 8: SKIN TIGHTENING SYSTEM AND PROCESS WITH LASER LIGHT

As humans age, their skin becomes thinner and less elastic. Sagging skin around the face and breasts is often an objectionable part of aging. Since many individuals want to remain young looking, face lifts for men and women and breast lifts for women are popular to those who can afford the cost. The present invention, through absorption of light energy, provides a tool for greatly simplifying breast lifts and face lifts, thereby making these procedures more economical.

Figure 29:
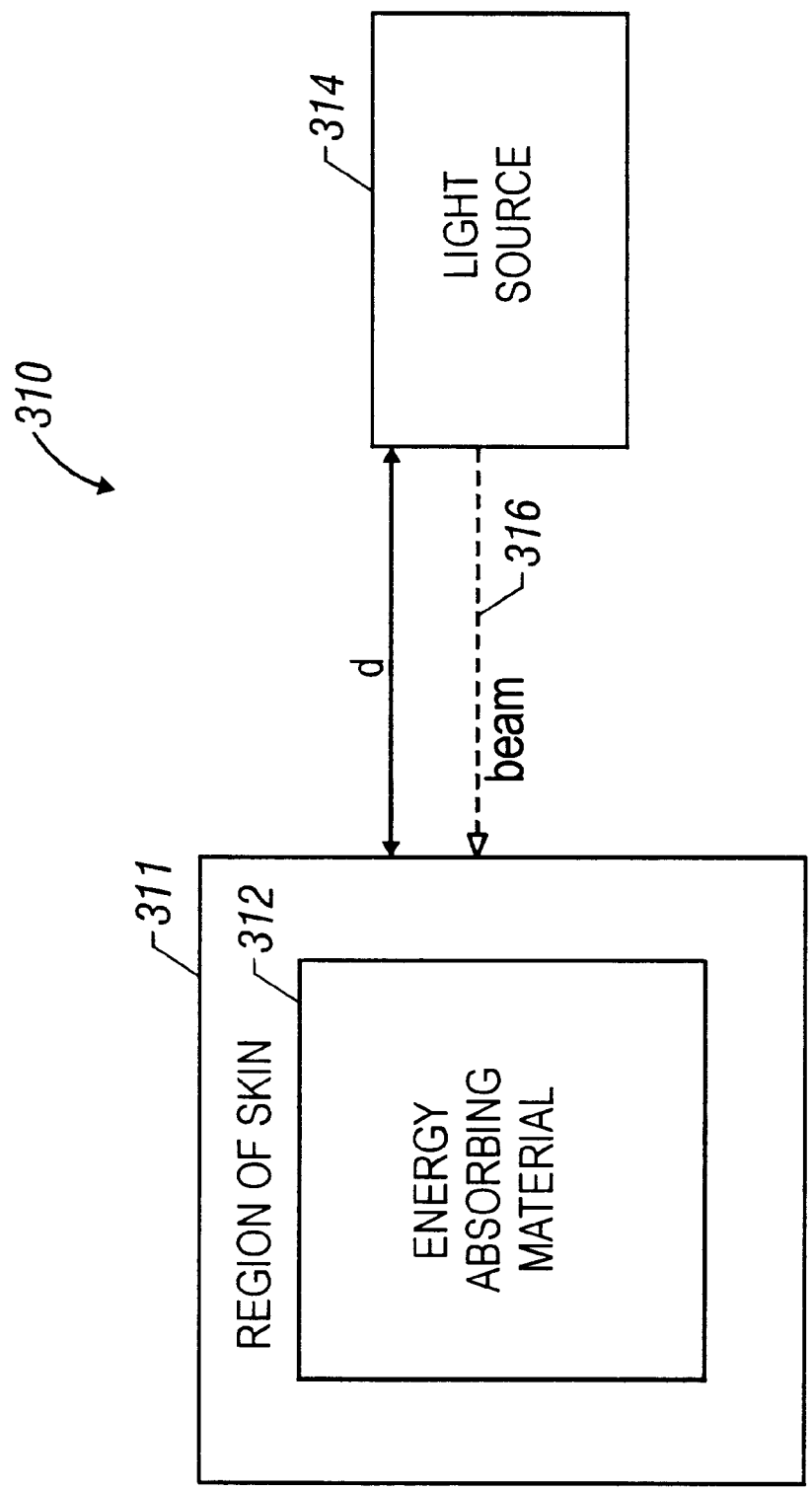
FIG. 29 is a system for practicing a skin tightening method according to the invention.

FIG. 29 shows a system 310 for increasing the tension and elasticity in a section of human skin 311, including an energy absorbing material 312 disposed in the skin at a distance "d" from an illumination source 314. An energized light beam 316, preferably a laser beam, is emitted from source 314. Beam 316 spans the distance d and imparts energy to the energy absorbing material 312, which can be graphite in a thread or a particulate form. As will be described in greater detail below, it is believed that with ajudicious choice of energy absorbing material 312 and illumination, illuminating energy absorbing material 312 causes such material to absorb energy, some of which is transferred to surrounding skin tissue. The transferred energy causes disturbances in the skin. The body's natural healing response then creates more collagen fibers in the region of the disturbances, thereby strengthening and tightening the skin.

Graphite is a good choice for the energy absorbing material because it has a three dimensional crystal structure that is strong in two directions and weak in the third direction. Accordingly, graphite thread is weak in a direction transverse to the longitudinal direction of the thread. The illumination energy source can thus break particles of graphite from near the thread's outer periphery.

A useful thread for embodiments of this invention is a thread comprised of about 30 strands of graphite fibers, each fiber having a diameter of about 10 micron. This type of thread can have a diameter of about 50 microns. A good light source 14 is a laser, for example an Nd:YAG laser. Graphite is strongly absorptive of the 1064 nanometer (nm) wavelength beam produced by the Nd:YAG laser, the absorption being more than 4,000 times greater than the absorption of this wavelength by human skin tissue. The penetration of the beam into solid graphite is in the range of 1 micron.

While not desiring to be limited to any particular theory of operation, it is believed that the invention operates in accordance with certain physical principles described now. When graphite thread is illuminated from one side with 10 nanosecond (ns), 3 J/cm$^2$ Nd:YAG pulses at a wavelength of 1064 nm, the surface atoms to a depth of about 1 micron are heated to the vaporization temperature of graphite which is 3,600° C. and a tiny but powerful explosion occurs on the surface layer. On a microscopic level, fragments of the surface of the thread disperse and travel away from the thread.

It is further believed that if the thread is embedded in dermal tissue and illuminated as described above with about 3 J/cm² 10 ns Nd:YAG pulses, the fragments will fly off through the dermal tissue and come to rest at distances from the thread of up to 500 microns, about 100 microns being the average travel distance. The fragments impact and damage skin tissue cells. The fragments dispersed from the thread arc typically very hot (e.g., temperatures in the range of about 3,000° C.). Accordingly, heat is transferred to surrounding tissue. On the average a one micron size particle ($10^{-12}$ cm³) of graphite at about 3,000° C. will carry about $10^{-8}$ J of heat energy. This is a very small quantity of energy, but there are many thousands of small micron size particles exploded off the graphite thread with each pulse and they are spread over distances ranging out to about 500 microns from the position of the thread. These hot, high energy fragments cause damage to the dermal tissue creating a long, very thin wound in the dermal tissue below the epidermis.

The skin of the face and breasts is about 2 mm thick. The epidermis is a thin (about 0.4 mm) outer layer of the skin and is composed primarily of layers (about 30) of cells which are produced by cell division at the lower levels of the epidermis and move up and into the stratum corneum over a period of about 45 days, becoming more compacted and flatter on the way. By the time the cells reach the stratum corneum, they are dead and are regularly flaked off.

The strength and flexibility of the skin is provided by the lower thicker layer of skin, the dermis, which includes blood vessels, sweat glands, sebaceous glands and hair follicles. A primary component of the dermis is a matrix of collagen fibers. These fibers are about 15 microns wide and relatively long. The collagen fibers are arranged in a three-dimensional, relatively randomly woven pattern. This pattern permits the skin to be stretched by distances of a few percent upon the application of a very small force. However, once the skin is stretched to the extent that the fibers making Lip the dermis become aligned roughly parallel to each other, further stretching force is resisted very strongly by the fibers. When the stretching force is removed the skin rebounds with the fibers resuming their three-dimensional, relatively random pattern.

A typical collagen fiber is made Up of several hundred small fibrils. These fibrils are about 0.1 micron wide that are, in turn, made up of individual molecules called tropocollagen molecules. The tropocollagen molecules arc made up of three polypeptide chains, each having a helical structure. Together, the three chains form a super-helix. Unlike the cells making up the epidermis, the collagen fibrils of the dermis are not living cells, but are produced by living cells in the dermis called fibroblasts. As we grow, the fibroblasts produce the dermal fibers as needed. When skin is damaged, fibroblast cells migrate to the site of the wound and initiate the production of new fibrils which combine to from new collagen fibers.

The dermis also includes a material called "ground substance," which fills spaces between the collagen fibers. Ground substance functions as a lubricant, allowing the collagen fibers to slide past each other. It is also thought that the ground substance functions as a pathway for diffusion of nutrients through the skin and to assist the fibroblast cells in creating new fibers.

Another component of the dermis is a network of elastic fibers which constitute about 2 to 4 percent of the total volume of the skin. These fibers are also, like the collagen fibers, produced by fibroblast cells. However, these fibers are comprised of elastin and are interwoven with the collagen fiber network and add greatly to the elastic properties of the skin.

EXAMPLE 12

Face Lift Procedure

A typical face lift tightens sagging facial skin by removing a portion of the sagging skin. The remaining skin is stretched to cover the space previously covered by the removed section so that some of the sag of the skin is eliminated. Incisions are usually made in hair-covered areas so that the resulting scar is not apparent. Current face lifting procedures have many adverse consequences including long periods of recovery after the treatments. In some cases, after the painful procedures and the long recovery times, the patient is disappointed with the results.

Figure 30B:
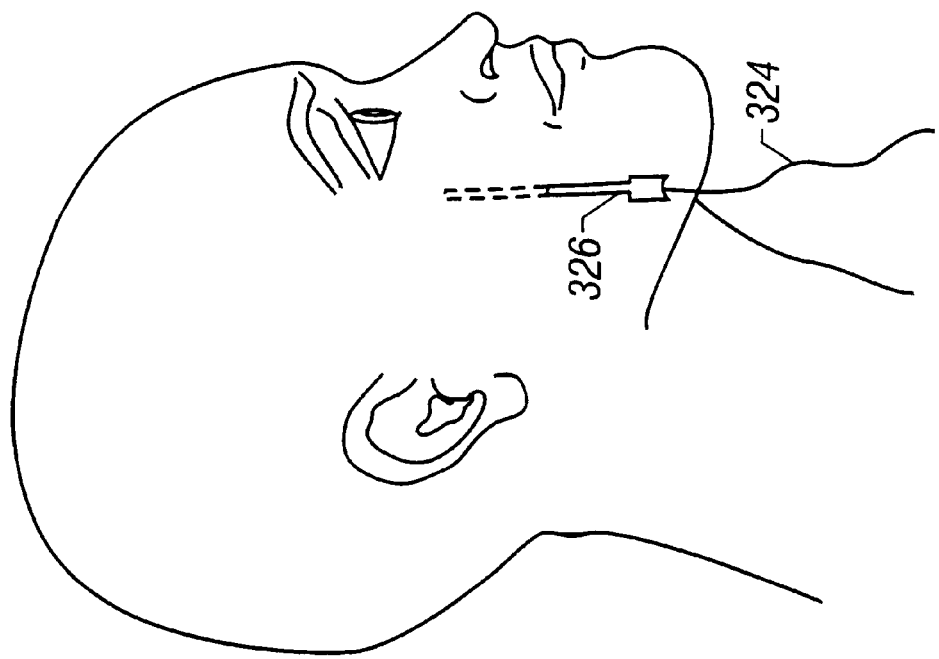
FIGS. 30A through 30D illustrate steps in a facial skin tightening process.
Figure 30A:
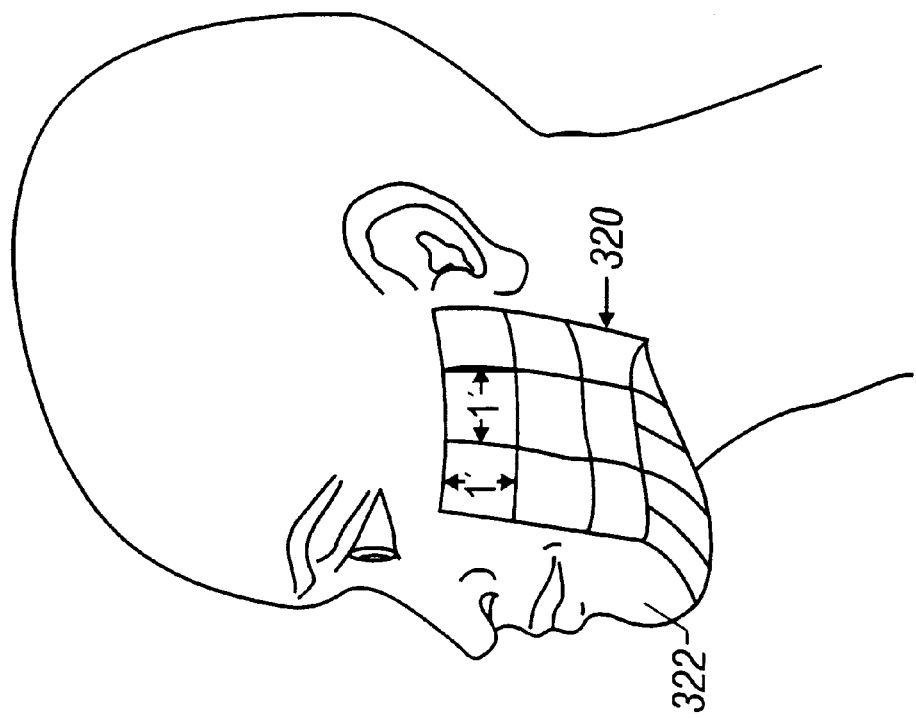
Figure 30D:
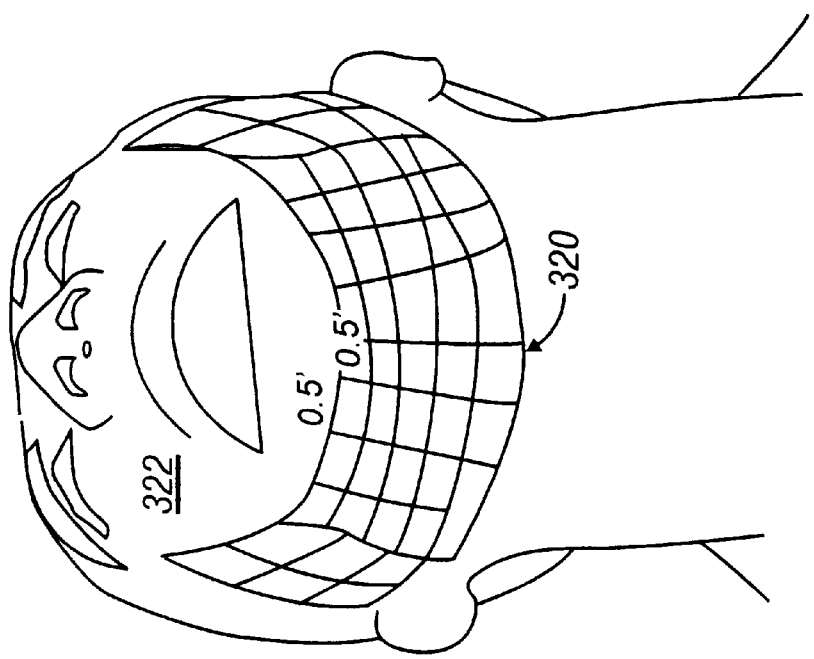
Figure 30C:
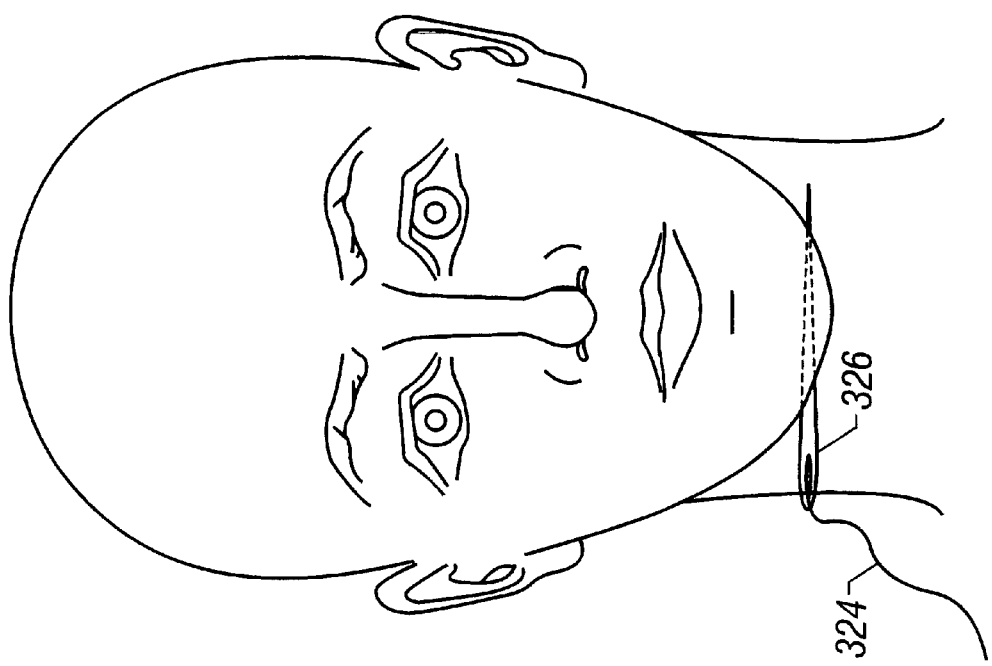
Figure 31B:
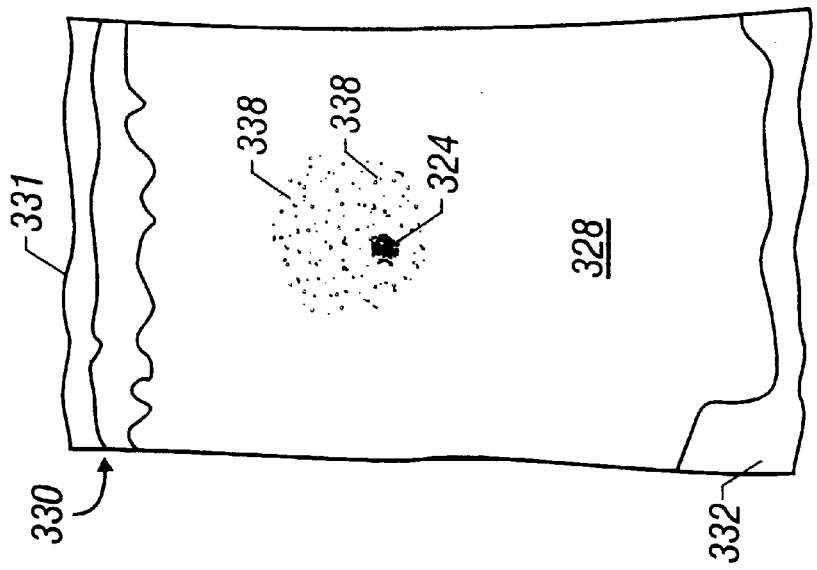
FIGS. 31A through 31F are diagrams of a section of human skin illustrating the results of illuminating a graphite thread within the dermis of the skin section.
Figure 31A:
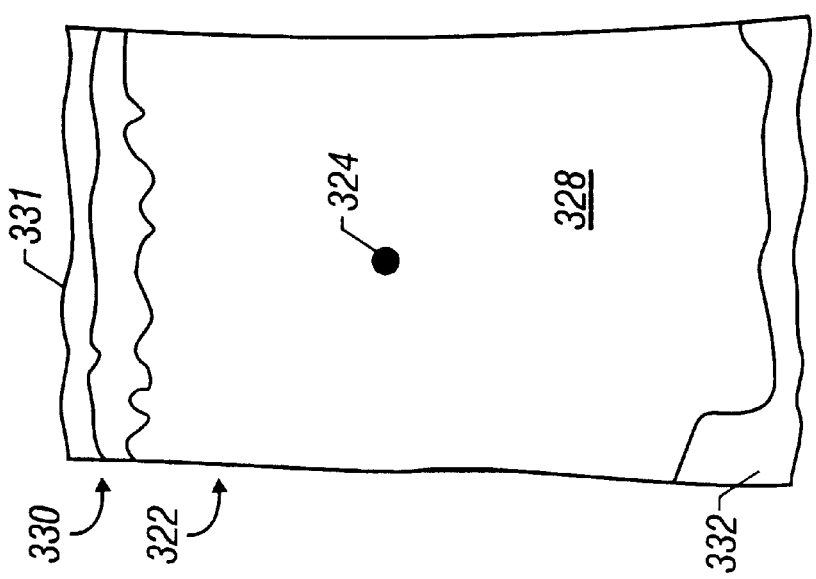

The present invention improves on surgical face lift procedures by eliminating the need to surgically remove skin tissue. Referring now to FIGS. 30A and 30D, grid lines 320 are drawn on the facial skin 322 of a patient at the beginning of the procedure. On each cheek grid lines 320 are about 1 inch apart and generally horizontal and vertical. Under the chin grid lines 320 are about ½ inch apart, six lines side to side and 7 lines front to back. A graphite thread 324 is then sewn through the dermis below grid lines 322 as shown in FIGS. 30B and 30C. Graphite thread 324 is implanted under skin 320 at a depth which is as close as possible to the middle of the dermis layer of the skin. FIG. 1B shows the position of a needle 326 used for inserting one of the vertical threads 324 in the right cheek of the patient. FIG. 1C shows needle 326 positioned for threading one of the side to side threads 324 under the chin. FIG. 31A shows a cross section of facial skin 322, which includes the dermis 328, the epidermis 330 with the stratum corneum 331 at the surface, and a layer of fat 332 below the dermis 328. Graphite thread 324, also shown in cross-section, is positioned about centrally in dermis 328.

Figure 32A:
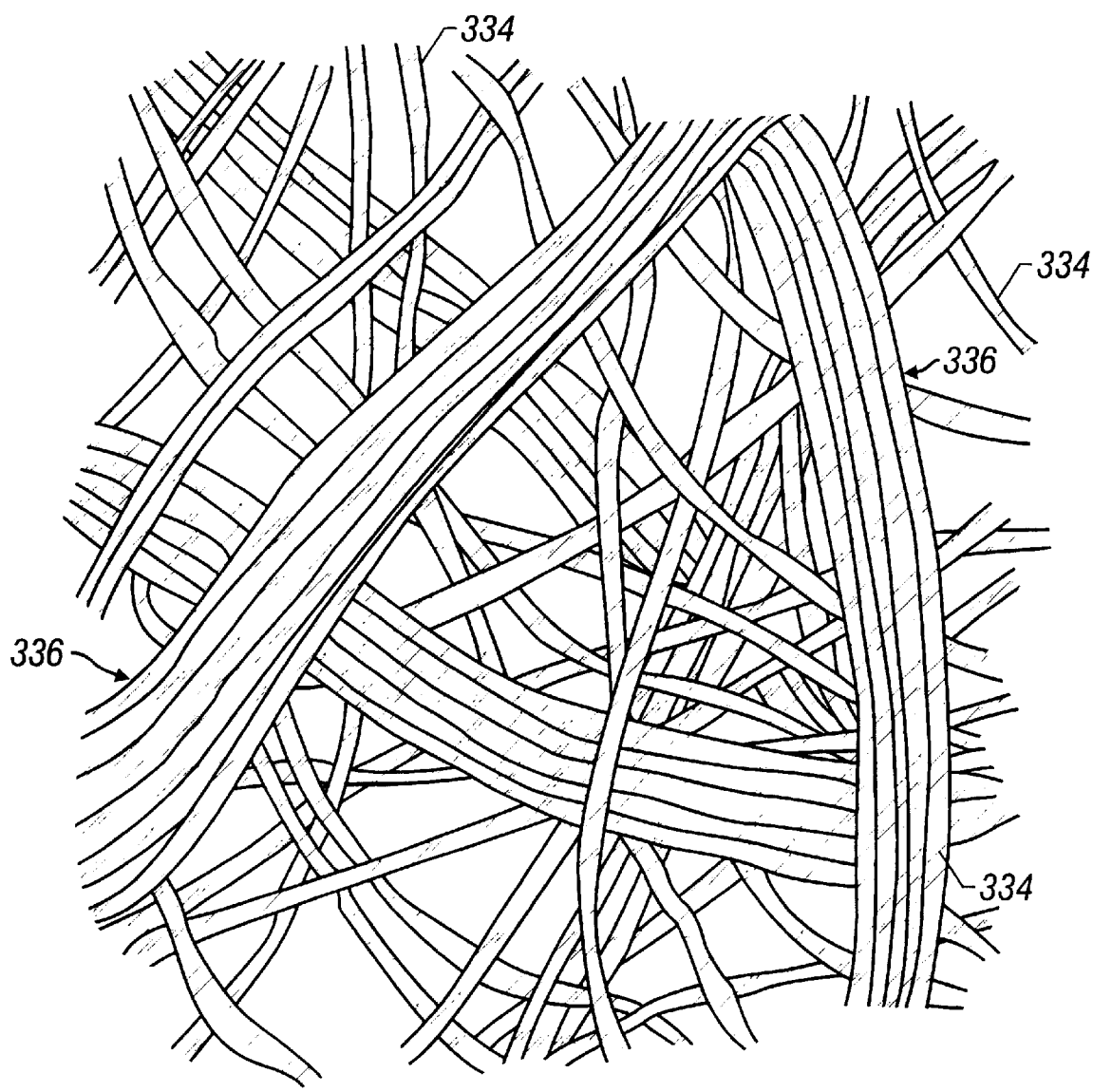
FIG. 32A is an enlarged view of collagen fibers in a dermal layer.
Figure 32B:
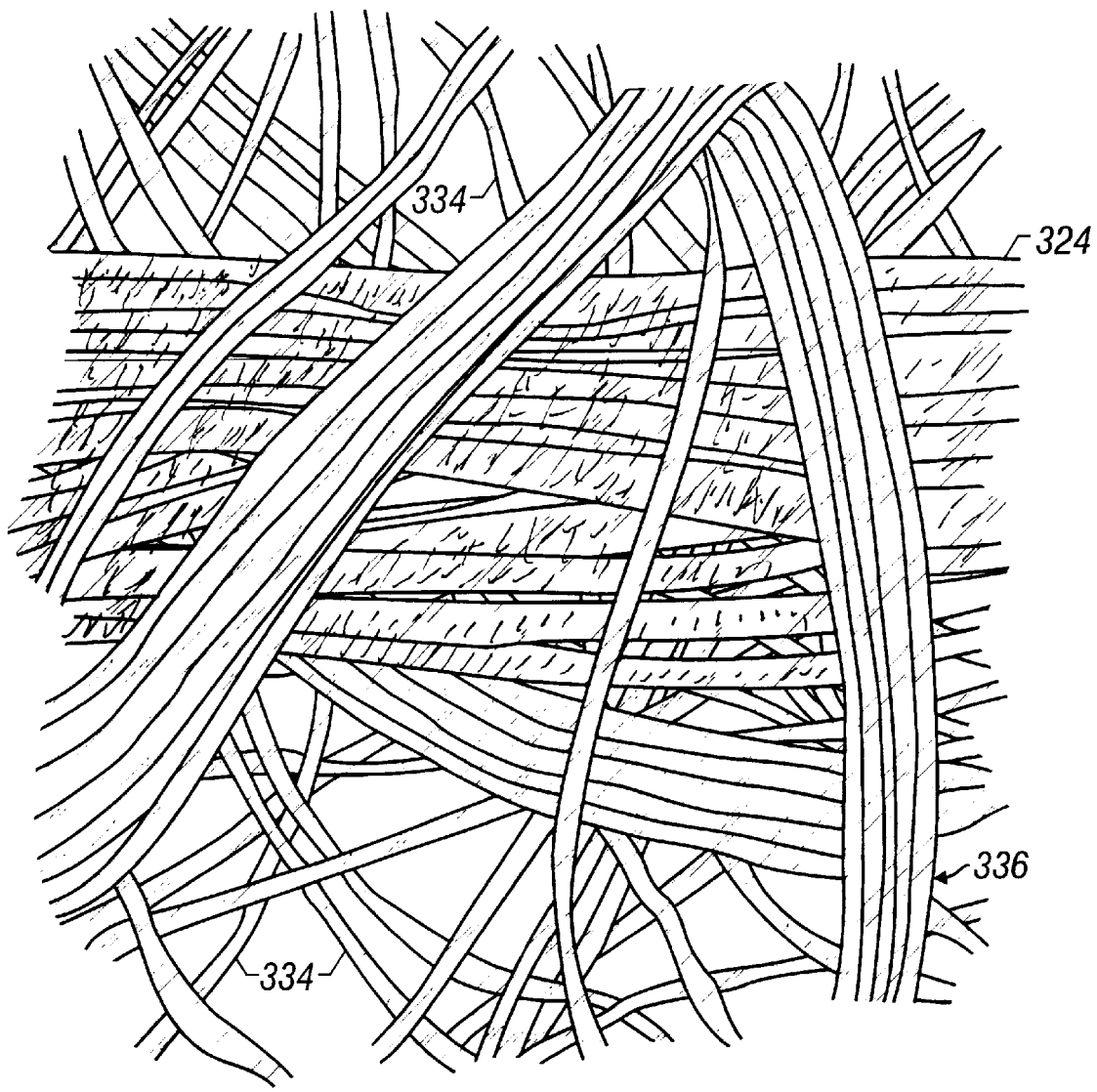
FIG. 32B is a similar view of a dermal layer with a graphite thread extending through the collagen fibers.

FIG. 32A is a representation of the collagen fibers 334 in skin tissue. Note that many of the individual fibers 334 are bundled into larger fiber bundles 336. FIG. 32B is a representation of a graphite thread 324 sewn into the dermal collagen fibers 334.

Once graphite threads 324 are in place, they can be illuminated. In the described embodiment, threads 324 arc illuminated with approximately 10 nanosecond light pulses produced by a Nd:YAG laser, the pulses having a fluence of about 3 J/cm². A pulse rate of 10 Hz can be used, and the beam can be scanned slowly along grid lines 320 so that each section of skin 11 receives about four pulses at the 10 Hz rate. A fluence of about 3 J/cm² appears to provide sufficient energy to heat the skin enough to raise its temperature a few degrees but not enough to cause any general skin damage other than in the immediate vicinity of the graphite thread.

Figure 31D:
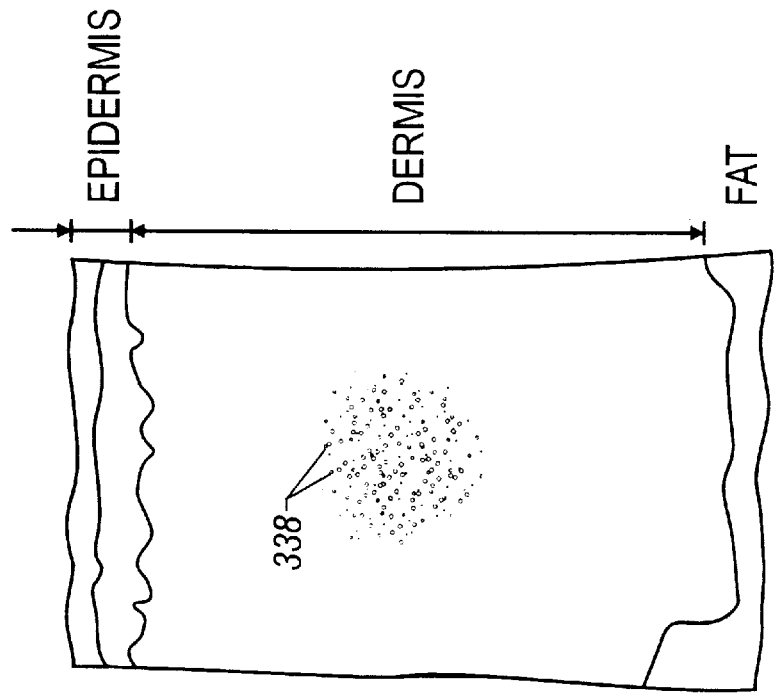
Figure 31C:
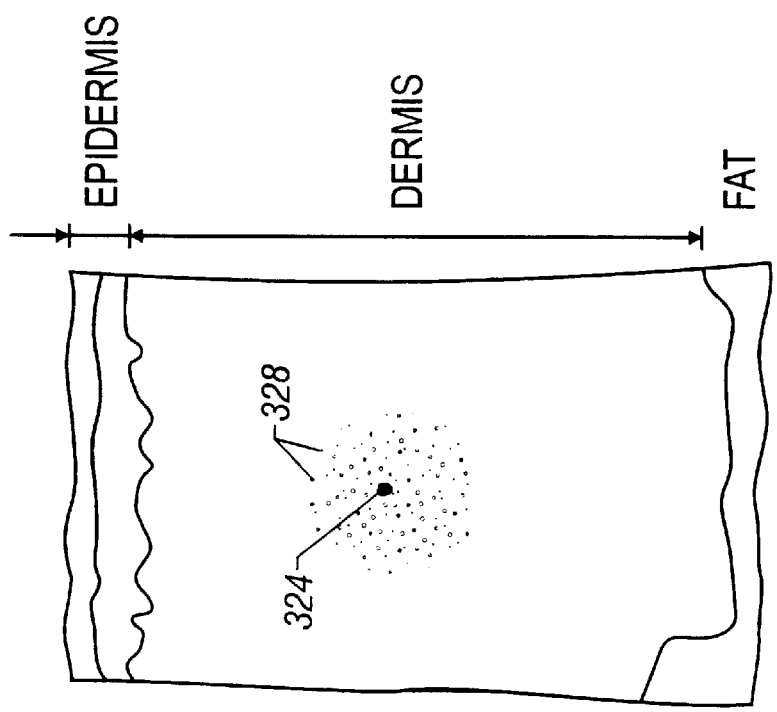
Figure 31F:
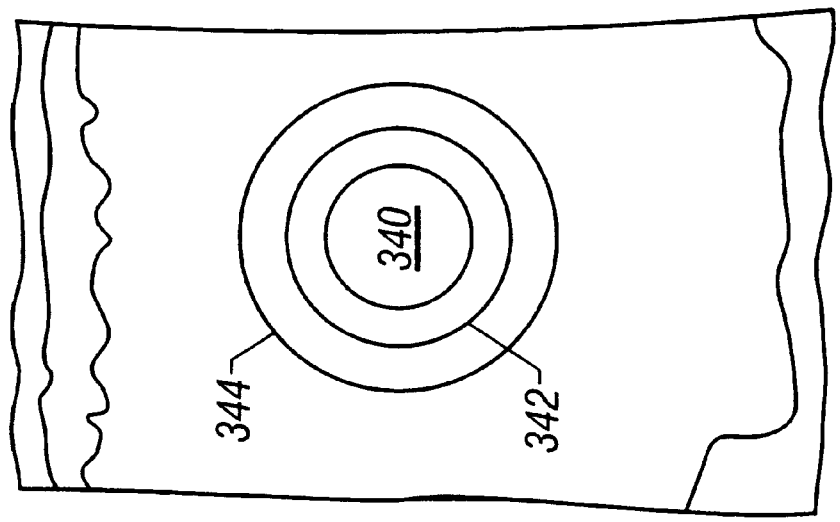
Figure 31E:
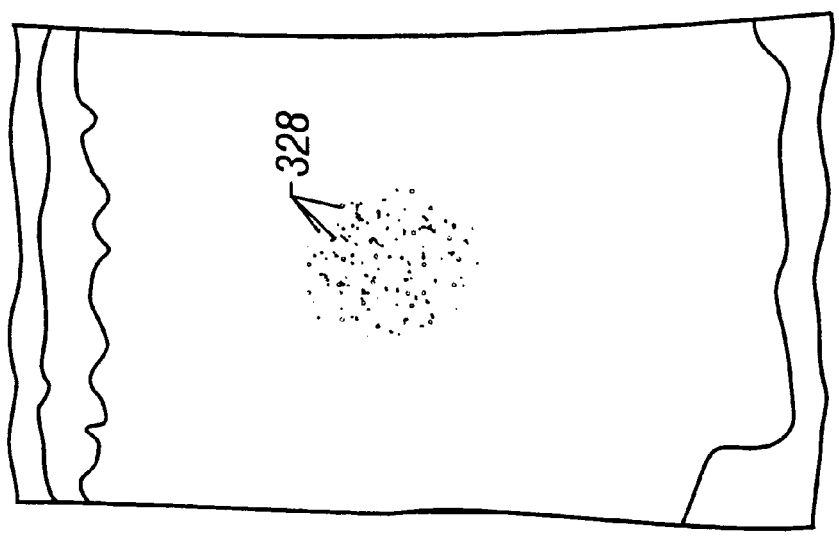
Figure 32C:
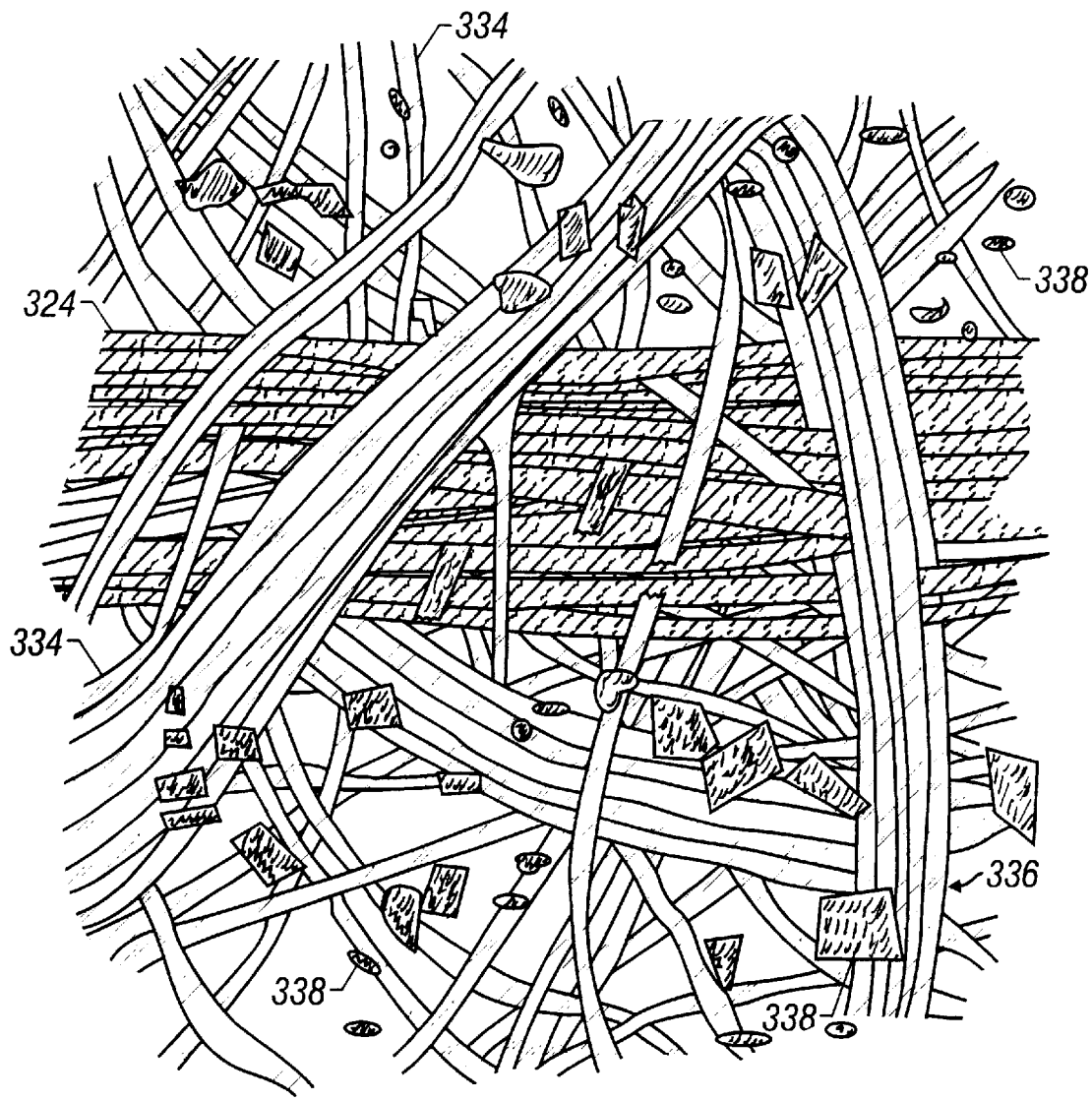
FIG. 32C shows the results of illuminating the thread with light in a skin tightening procedure according to the invention.
Figure 32D:
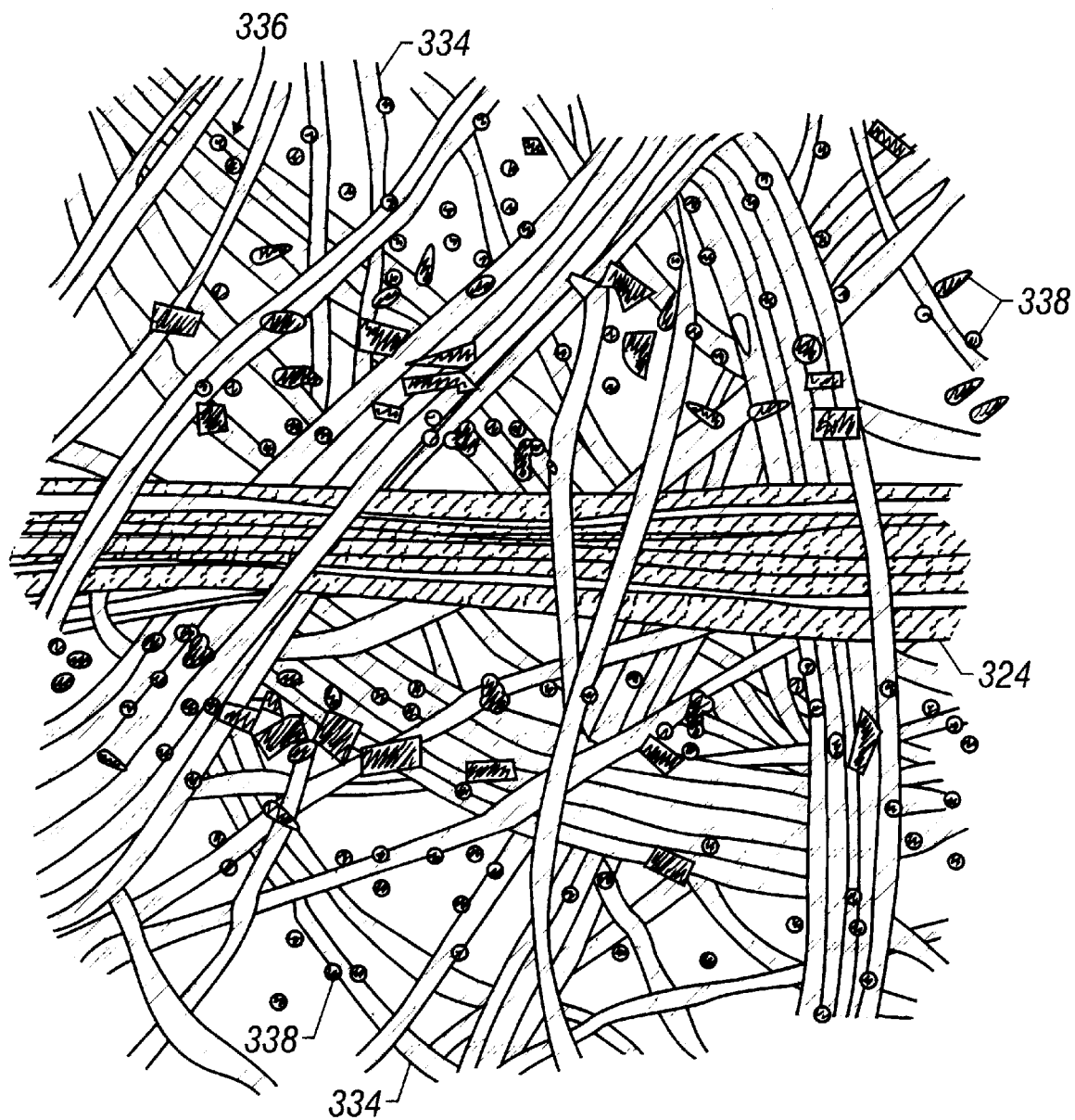
FIG. 32D shows the results of further illumination.

It is believed that absorption of the light pulses by graphite thread 324 causes tiny explosions in the thread's strand layers. FIG. 31B and FIG. 32C both show the result of one pulse. Note that graphite fragments 338 are now distributed over a volume about 100 to 500 microns from graphite thread 324. Note also in FIG. 32C some damage has been created in some nearby collagen fibers 334. FIG. 32D, and FIG. 31C show the results after more pulses. Thread 324 has been thinned substantially. FIGS. 31D and 31E show the results after yet more pulses, which break up thread 324 and break graphite particles 338 into smaller and smaller fragments. After about 20 pulses, thread 324 has been completely broken up and most of the particles have been vaporized or broken into such small particles that they are almost invisible.

The tiny explosions of graphite thread 324 and of graphite particles 338 damage the dermal tissue within about 100 microns to 500 microns of thread 324. The greatest damage is closest to thread 324. For purposes of illustration, some damage is shown in the volume represented by circle 340 in FIG. 31F, lesser damage in the volume represented by circle 342 and still lesser damage in the volume represented by circle 344.

It is further believed that the above-described process creates a very thin, long wound within the dermis. Again, not wishing to be limited by any particular scientific or medical theory, it is believed that the beneficial results of the invention can probably be explained as follows. As with a normal skin wound, healing takes place over a period of about 42 days. However, since the epidermis is not affected, the wound is largely not apparent and no surface scar is created, although there may be some slight swelling and redness. At the time of the injury, inflammatory chemicals are released, causing local blood vessels to dilate and become more permeable. Fluid, white blood cells, and blood proteins can then enter the wound site. At first, broken blood vessels are plugged with clotted blood. However, within 2 to 5 days capillary buds invade the clots, restoring vascular supply. Fibroblasts enter the region and secrete collagen. Macrophages dispose of dead cells and other debris including small pieces of damaged collagen fibers. Over the next 40 days healing continues with new connective tissue gradually forming and creating strings of new fibers along the path of the wound. The treated area should be prevented from undue stretching during the 40 day healing period. This allows new collagen fibers and associated elastin fibers to fully develop before too much stress is placed on them. The new tissue, like typical scar tissue, tends to shrink. This applies new tension to the treated skin sections. The new tension provides natural support to sagging skin with no scars and without any unnatural appearance, such as may result from surgical face lift procedures.

EXAMPLE 13
Breast Lift Procedure

Figure 33A:
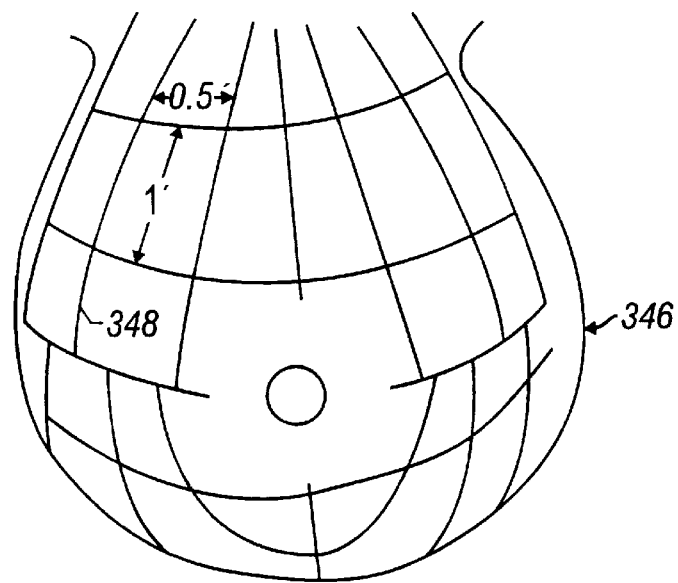
FIGS. 33A and 33B are drawings of a breast showing a grid line pattern for a breast lift procedure according to the invention.
Figure 33B:
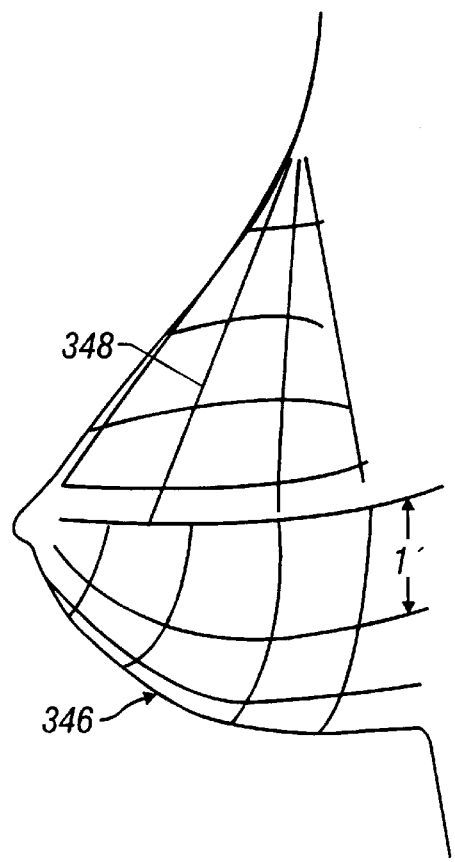

A breast lift procedure may be carried out similar to that described above with reference to a face lift procedure. Referring now to FIGS. 33A and 33B, a breast 346 is shown with grid lines 348 in a pattern under which graphite threads 324 are to be implanted in the dermis. The illumination is as described above in the facial skin tightening process. As with that process, it is believed that long thin wounds are created in the dermis which are about 1 millimeter wide. It is recommended that a woman having this procedure wear a support bra for about 40 days following the breast lift procedure to prevent the breast skin from stretching too much during the healing. As with the facelift, this is believed to allow new collagen fibers and associated elastin fibers to fully develop before too much stress is placed on the new fibers. The new tissue, like typical scar tissue, tends to shrink the treated skin sections, applying new tension to the skin that helps to lift the breasts.

EXAMPLE 14
Skin Tightening Procedure Using Particles

As an alternative to using graphite threads for a skin tightening procedure, small graphite particles can be implanted in selected patterns within the dermis by employing tattooing techniques. Any of the many well known tattoo techniques can be used to create the tattoo. Most of these well known procedures use an array of needles to punch a large number of small shallow holes in the skin into which the tattoo ink is rubbed. To be effective as a permanent tattoo, the ink has to be placed below the epidermis into the dermis.

In a skin tightening procedure, a tattoo-type solution to which I micron graphite particles have been added is used to create a pattern as shown in FIGS. 30A and 30C or in FIGS. 33A and 33B using conventional tattooing techniques. The graphite particles are deposited within the dermis in lines about 1 millimeter wide with a concentration of about 1,000 particles per millimeter of length. Illumination is the same as described above. The results are similar to using thread as described above.

A number of embodiments of the present invention have been described. Nevertheless, it will be understood that various modifications may be made without departing from the spirit and scope of the invention. Accordingly, other embodiments are within the scope of the following claims.

What is claimed is:

1. A skin treatment process for increasing the tension and elasticity in a region of human skin including dermal tissue, including the steps of:

(a) placing in the dermis an energy absorbing material having a high optical absorption of at least one frequency band of light, wherein the energy absorbing material is graphite in a thread and the thread is placed in the dermis by sewing the thread through the dermis; and (b) illuminating the region of skin with the at least one frequency band of light, a portion which penetrates the region of skin and is absorbed in the energy absorbing material thereby affecting the dermal tissue to provide increased elasticity for the skin region.

2. The process of claim 1, wherein sewing the thread includes sewing the thread to a depth that is close to the middle of the dermis.

3. The process of claim 1, wherein sewing the thread through the dermis includes sewing the thread through the dermis in a grid.

4. The process of claim 3, wherein adjacent lines of the grid are spaced apart about one half to about one inch.

5. The process of claim 1, wherein placing the thread includes first drawing a grid line on the region of human skin including dermal tissue, and then sewing the thread through the dermis below the grid lines.

6. The process of claim 1, wherein the thread is comprised of graphite fibers.

7. The process of claim 6, wherein the thread is comprised of about 20 of the graphite fibers, each of the graphite fibers having a diameter of about 10 microns, and the thread having a diameter of about 50 microns.

8. The process of claim 1, wherein illuminating includes illuminating with a laser.

9. The process of claim 8, wherein the laser is a Nd:YAG laser illuminating with light pulses having a wavelength of about 1064 nm.

10. The process of claim 9, wherein the light pulses have a duration of about 10 nanoseconds, and an energy density of about 3 J/cm$^2$.

11. A skin treatment process for increasing the tension and elasticity in a region of human skin including dermal tissue, including the steps of:

(a) placing in the dermis an energy absorbing material having a high optical absorption of at least one frequency band of light, wherein the energy absorbing material includes graphite particles in a solution and wherein the graphite particles are placed in the dermis by piercing the skin with a needle and rubbing the solution on the pierced skin; and (b) illuminating the region of skin with at least one frequency band of light, a portion which penetrates the region of skin and is absorbed in the energy absorbing material thereby affecting the dermal tissue to provide increased elasticity for the skin region.

12. The process of claim 11, wherein the light source includes a laser.

13. The process of claim 12, wherein the laser comprises a Nd:YAG laser providing light pulses having a wavelength of about 1064 nm.

14. The process of claim 13, wherein the light pulses have a duration of about 10 nanoseconds, and an energy density of about 3 J/cm$^2$.

* * * * *